US012084431B2

(12) United States Patent
Durak et al.

(10) Patent No.: US 12,084,431 B2
(45) Date of Patent: Sep. 10, 2024

(54) PHARMACEUTICAL SALTS OF PYRIMIDINE DERIVATIVES AND METHOD OF TREATING DISORDERS

(71) Applicant: ARIAD Pharmaceuticals, Inc., Cambridge, MA (US)

(72) Inventors: Landon J. Durak, Cambridge, MA (US); Marianne Langston, Cambridge, MA (US); Pradeep Kumar Sharma, Cambridge, MA (US); Thai Hiep Nguyen, Dorchester, MA (US); Shuanglian Li, Cambridge, MA (US); Xiaoguang Zhang, Cambridge, MA (US)

(73) Assignee: TAKEDA PHARMACEUTICAL COMPANY LIMITED (JP)

( * ) Notice: Subject to any disclaimer, the term of this patent is extended or adjusted under 35 U.S.C. 154(b) by 864 days.

(21) Appl. No.: 17/055,164

(22) PCT Filed: May 13, 2019

(86) PCT No.: PCT/US2019/032002
§ 371 (c)(1),
(2) Date: Nov. 13, 2020

(87) PCT Pub. No.: WO2019/222093
PCT Pub. Date: Nov. 21, 2019

(65) Prior Publication Data
US 2021/0309640 A1    Oct. 7, 2021

Related U.S. Application Data

(60) Provisional application No. 62/671,166, filed on May 14, 2018, provisional application No. 62/671,182, filed on May 14, 2018.

(51) Int. Cl.
*C07D 403/04* (2006.01)
*A61P 35/00* (2006.01)

(52) U.S. Cl.
CPC ............ *C07D 403/04* (2013.01); *A61P 35/00* (2018.01); *C07B 2200/13* (2013.01)

(58) Field of Classification Search
CPC .... C07D 403/04; A61P 35/00; C07B 2200/13
See application file for complete search history.

(56) References Cited

U.S. PATENT DOCUMENTS

| | | | |
|---|---|---|---|
| 2005/0288327 A1 | 12/2005 | Uesugi | |
| 2009/0306101 A1 | 12/2009 | Solca | |
| 2010/0298156 A1 | 11/2010 | Lee-Hoeflich | |
| 2011/0160237 A1 | 6/2011 | Ali et al. | |
| 2011/0263541 A1 | 10/2011 | Luo | |
| 2012/0094999 A1 | 4/2012 | Gray et al. | |
| 2017/0008889 A1 | 1/2017 | Lan et al. | |
| 2017/0313714 A1 | 11/2017 | Wei et al. | |

FOREIGN PATENT DOCUMENTS

| | | |
|---|---|---|
| CN | 106995437 A | 8/2017 |
| WO | 87/05781 A2 | 10/1987 |
| WO | 87/05897 A2 | 10/1987 |
| WO | 87/05898 A2 | 10/1987 |
| WO | 2000006555 A1 | 2/2000 |
| WO | 2004-101564 A1 | 11/2004 |
| WO | 2006/021002 A2 | 2/2006 |
| WO | 2007/050347 A1 | 5/2007 |
| WO | 2008/032858 A2 | 3/2008 |
| WO | 2008/099073 A1 | 8/2008 |
| WO | 2008/099074 A1 | 8/2008 |
| WO | 2008/099075 A1 | 8/2008 |
| WO | 2009/003998 A2 | 1/2009 |
| WO | 2009/056693 A1 | 5/2009 |
| WO | 2009/158571 A1 | 12/2009 |
| WO | 2010/093808 A1 | 8/2010 |
| WO | 2010/126895 A1 | 11/2010 |
| WO | 2010/132598 A1 | 11/2010 |
| WO | 2012/020215 A1 | 2/2012 |
| WO | 2012/068440 A1 | 5/2012 |
| WO | 2012/068450 A1 | 5/2012 |
| WO | 2012/158658 A1 | 11/2012 |
| WO | 2013/014448 A1 | 1/2013 |
| WO | 2013/170113 A1 | 11/2013 |
| WO | 2013/170115 A1 | 11/2013 |
| WO | 2014/160478 A1 | 10/2014 |
| WO | 2015/039612 A1 | 3/2015 |

(Continued)

OTHER PUBLICATIONS

Wang, E.C., et al., A New Route to N-Aryl 2-Alkenamides, N-Allyl N-Aryl 2-Alkenamides, and N-Aryl α, β-Unsaturated γ-Lactams from N-Aryl 3-(Phenylsulfonyl)propanamides, J. of the Chinese Chem. Soc., vol. 48, pp. 83-90 (2001). (Year: 2001).*

Wang, E.-C et al., "A New Route to N-Aryl 2-Alkenamides, N-Allyl N-Aryl 2-Alkenamides, and N-Aryl α,β-Unsaturated γ-Lactams from N-Aryl 3-(Phenylsulfonyl)propanamides" Journal of the Chinese Chemical Society, 2001, vol. 48, pp. 83-90.

Cross, Darren A.E., et al., AZD9291, an Irreversible EGFR TKI, Overcomes T790M-Mediated Resistance to EGFR Inhibitors in Lung Cancer, Cancer Discovery, vol. 4, Issue 9, pp. 1046-1061, Jun. 3, 2014.

(Continued)

*Primary Examiner* — Erich A Leeser

(74) *Attorney, Agent, or Firm* — Honigman LLP; Lucy X. Yang; Jonathan P. O'Brien

(57) ABSTRACT

The present disclosure relates to pharmaceutical salts and polymorphic forms of pyrimidine derivatives that have inhibitory activities against mutant epidermal growth factor receptor (EGFR). The present disclosure further relates to the processes for the preparation of the pyrimidine derivatives and to the pharmaceutical salts and the polymorphic forms of the pyrimidine derivatives.

30 Claims, 36 Drawing Sheets

(56) References Cited

FOREIGN PATENT DOCUMENTS

| WO | 2015/039613 | A1 | 3/2015 | | |
|---|---|---|---|---|---|
| WO | 2015/140717 | A1 | 9/2015 | | |
| WO | 2015-195228 | A1 | 12/2015 | | |
| WO | WO 2015/195228 | | * 12/2015 | ........... | C07D 403/14 |
| WO | 2016/046530 | A1 | 3/2016 | | |
| WO | 2016/173505 | A1 | 11/2016 | | |

OTHER PUBLICATIONS

Ward, Richard A. et al., Structure- and Reactivity-Based Development of Covalent Inhibitors of the Activating and Gatekeeper Mutant Forms of the Epidermal Growth Factor Receptor (EGFR), Journal of Medicinal Chemistry, American Chemical Society, vol. 56, No. 17, pp. 7025-7048, Sep. 12, 2013.

Caira, Mino R, "Crystalline Polymorphism of Organic Compounds", Topics in Current Chemistry; [Topics in Current Chemistry], Springer, Berlin, DE, vol. 198, Jan. 1998 (Jan. 1998), pp. 163-208, XP008166276, ISSN: 0340-1022.

Hilfiker, et al., "Relevance of Solid-state Properties for Pharmaceutical Products", Polymorphism in the Pharmaceutical Industry, Jan. 1, 2006 (Jan. 1, 2006), 19 pages, Wiley-VCH Verlag GmbH, Weinheim, XP002528052, ISBN: 978-3-527-31146-0.

* cited by examiner

XRPD data for the polymorphic Form-I of the anhydrous free base of Compound (A)

TG/DTA profile for the polymorphic Form-I of the anhydrous free base of Compound (A)

XRPD data for the polymorphic Form-I of the succinate salt of Compound (A)

XRPD data for the polymorphic Form-III of the succinate salt of Compound (A)

XRPD data for the polymorphic Form-I of the hydrobromide salt of Compound (A)

DSC profile for the polymorphic Form-I of the hydrobromide salt of Compound (A)

XRPD data for the polymorphic Form-I of the hydrochloride salt of Compound (A)

DSC profile for the polymorphic Form-I of the hydrochloride salt of Compound (A)

XRPD data for the polymorphic Form-I of the sulfate salt of Compound (A)

DSC profile during a 1st heating cycle for the polymorphic Form-I of the sulfate salt of Compound (A)

XRPD data for the polymorphic Form-I of the tosylate salt of Compound (A)

DSC profile for the polymorphic Form-I of the tosylate salt of Compound (A)

XRPD data for the polymorphic Form-III of the mesylate salt of Compound (A)

XRPD data for the polymorphic Form-III of the oxalate salt of Compound (A)

XRPD data for the polymorphic Form-II of the fumarate salt of Compound (A)

XRPD data for the polymorphic Form-I of the fumarate salt of Compound (A)

XRPD data for the polymorphic Form-I of the hippurate salt of Compound (A)

PHARMACEUTICAL SALTS OF PYRIMIDINE DERIVATIVES AND METHOD OF TREATING DISORDERS

CROSS REFERENCE TO RELATED APPLICATIONS

This application is a 35 U.S.C. § 371 United States National Phase Application of, and claims priority to, PCT Application No. PCT/US2019/032002, filed May 13, 2019, which claims the benefit of U.S. provisional application No. 62/671,166, filed May 14, 2018 and U.S. provisional application No. 62/671,182, filed on May 14, 2018, the entirety of which is incorporated herein by reference.

TECHNICAL FIELD

The present disclosure relates to pharmaceutical salts and polymorphic forms of pyrimidine derivatives that have inhibitory activities against mutant epidermal growth factor receptor (EGFR). The present disclosure further relates to the processes for the preparation of the pyrimidine derivatives and to the pharmaceutical salts and the polymorphic forms of the pyrimidine derivatives.

The present disclosure further relates to compositions comprising the pyrimidine derivatives or a pharmaceutically acceptable form thereof and methods or dosing regimens comprising administering the pyrimidine derivatives or a pharmaceutically acceptable salts thereof.

BACKGROUND

Lung cancer is composed of non-small-cell lung cancer (NSCLC), small-cell lung cancer (SCLC), and neuroendocrine tumors. Approximately 10% of patients with NSCLC in the US (10,000 cases/year) and 35% in East Asia are reported to have tumor-associated epidermal growth factor receptor (EGFR) mutations. New England J. Med. 2004; 350(21):2129-39.

EGFR (alternatively named ErbB1 or HER1) is part of the ErbB family of transmembrane receptor tyrosine kinases involved in signal transduction pathways that regulate proliferation and apoptosis. Inhibitors of the EGFR have emerged as effective therapies for some patients and represent an important target for therapeutic intervention in oncology. The development and clinical application of inhibitors that target EGFR provide important insights for new lung cancer therapies, as well as for the broader field of targeted cancer therapies. *Nature Review Cancer* 2007; 7, 169-181 (March 2007).

A primary concern for the manufacture of pharmaceutical compounds is the stability of an active substance. An active substance ideally has a stable crystalline morphology to ensure consistent processing parameters and pharmaceutical quality. Unstable active substances may affect the reproducibility of the manufacturing process and thus lead to final formulations which do not meet the high quality and stringent requirements imposed on formulations of pharmaceutical compositions.

There is thus a continuing need for new EGFR inhibitors, additional stable forms of EGFR inhibitors, and improved manufacturing processes for preparing EGFR inhibitors.

Further, there is a need for further development of pharmaceutical compositions and methods of treatment, including developing dosages and dosing regimens.

SUMMARY

In one embodiment, the present disclosure provides an improved process for preparing EGFR inhibitors of formula (I)

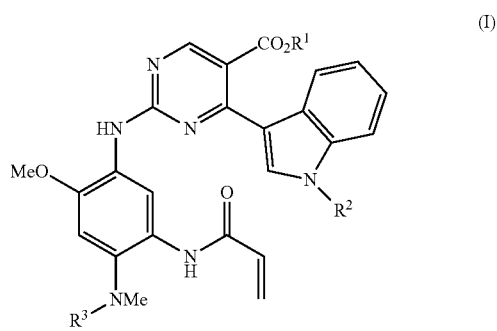

(I)

or a pharmaceutically acceptable salt thereof, wherein $R^1$ is alkyl; $R^2$ is H or alkyl; and $R^3$ is alkyl substituted with an amino or heterocycloalkyl.

In another embodiment, the present disclosure provides a process for preparing an EGFR inhibitor of Compound (A)

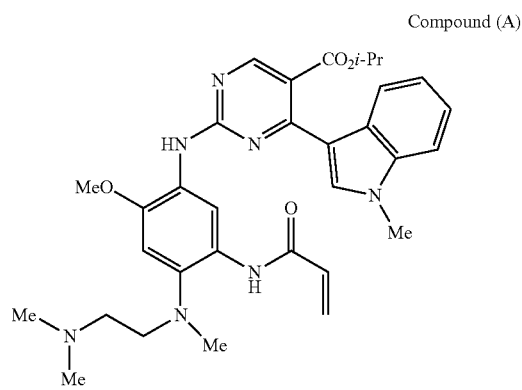

Compound (A)

or a pharmaceutically acceptable salt thereof.

In some embodiments, the present disclosure provides novel polymorphic forms of Compound (A) and processes for the preparation thereof.

In some embodiments, the present disclosure provides novel polymorphic forms of various pharmaceutically acceptable salts of Compound (A) and processes for the preparation thereof.

In some embodiments, the present disclosure provides succinate salt of Compound (A), its novel polymorphic forms, and processes for the preparation thereof.

In some embodiments, the present disclosure provides a pharmaceutical composition comprising an EGFR inhibitor described herein, a pharmaceutically acceptable salt thereof, or a polymorphic form thereof, and a pharmaceutically acceptable carrier.

In some embodiments, the present disclosure provides administering to a subject in need thereof a therapeutically effective amount of an EGFR inhibitor described herein, or a pharmaceutically acceptable salt thereof, or a polymorphic form thereof for treating cancers associated with mutant EGFR.

In some embodiments, the present disclosure provides administering a therapeutically effective amount of an EGFR inhibitor described herein, or a pharmaceutically acceptable salt thereof, or a polymorphic form thereof to a subject suffering from cancer, including, but not limited to, lung cancer including non-small cell lung cancer (NSCLC) and small cell lung cancer (SCLC), colorectal cancer, pancreatic cancer, head and neck cancers, breast cancer, ovarian cancer, uterine cancer, gastric cancer, bladder cancer, glioma cancer, or stomach cancer.

In some embodiments, the present disclosure provides using an EGFR inhibitor described herein, or a pharmaceutically acceptable salt thereof, or a polymorphic form thereof for the preparation of a medicament for treating cancer such as, but not limited to, lung cancer (including NSCLC and SCLC), colorectal cancer, pancreatic cancer, head and neck cancers, breast cancer, ovarian cancer, uterine cancer, gastric cancer, bladder cancer, glioma cancer, or stomach cancer.

In some embodiments, the EGFR inhibitor is a compound of formula (I), or a pharmaceutically acceptable salt thereof.

In some embodiments, the EGFR inhibitor is polymorphic Form-I of Compound (A).

In some embodiments, the EGFR inhibitor is Compound (A), or succinate salt of Compound (A).

In some embodiments, the EGFR inhibitor is succinate salt of Compound (A) in a substantially crystalline form.

In some embodiments, the EGFR inhibitor is polymorphic Form-I of succinate salt of Compound (A).

In some embodiments, the present disclosure relates to a method of treating a disorder associated with mutant EGFR or mutant HER2, the method comprising administering to a patient in need thereof Compound (A) or a pharmaceutically acceptable salt thereof at a dose of from about 80 mg to about 200 mg per day.

In some embodiments, Compound (A) or a pharmaceutically acceptable salt thereof is administered at a dose of from about 40 mg to about 100 mg twice daily or from about 80 mg to about 200 mg once daily.

In some embodiments, Compound (A) or a pharmaceutically acceptable salt thereof is administered at a dose of from about 60 mg to about 80 mg twice daily or from about 120 mg to about 160 mg once daily.

In some embodiments, Compound (A) or a pharmaceutically acceptable salt thereof is administered at a dose of about 120 mg or about 160 mg per day.

In some embodiments, Compound (A) or a pharmaceutically acceptable salt thereof is administered at a dose of about 60 mg or about 80 mg twice daily.

In some embodiments, Compound (A) or a pharmaceutically acceptable salt thereof is administered at a dose of about 60 mg twice daily.

In some embodiments, Compound (A) or a pharmaceutically acceptable salt thereof is administered at a dose of about 80 mg twice daily.

In some embodiments, Compound (A) or a pharmaceutically acceptable salt thereof is administered at a dose of about 120 mg once daily.

In some embodiments, Compound (A) or a pharmaceutically acceptable salt thereof is administered at a dose of about 160 mg once daily.

In some embodiments, Compound (A) or a pharmaceutically acceptable salt thereof is administered orally.

In some embodiments, Compound (A) or a pharmaceutically acceptable salt thereof is in a solid dosage form.

In some embodiments, the solid dosage form is a capsule or tablet.

In some embodiments, Compound (A) or a pharmaceutically acceptable salt thereof is administered on a 28-day cycle.

In some embodiments, Compound (A) or a pharmaceutically acceptable salt thereof is administered on a 21-day cycle.

In some embodiments, Compound (A) or a pharmaceutically acceptable salt thereof is administered one or more times per day (e.g., once daily or twice daily) for at least seven consecutive days.

In some embodiments, Compound (A) or a pharmaceutically acceptable salt thereof is administered one or more times per day (e.g., once daily or twice daily) for at least 21 or 28 consecutive days.

In some embodiments, the disorder is associated with mutant EGFR having one or more insertion mutations in the exon 20 domain.

In some embodiments, the disorder is associated with mutant EGFR having one or more deletion mutations in the exon 20 domain.

In some embodiments, the disorder is associated with mutant HER2 having one or more insertion mutations in the exon 20 domain.

In some embodiments, the disorder is associated with mutant HER2 having one or more deletion mutations in the exon 20 domain.

In some embodiments, the disorder is a cancer associated with mutant EGFR or mutant HER2.

In some embodiments, the cancer is lung cancer, colorectal cancer, pancreatic cancer, head and neck cancer, breast cancer, ovarian cancer, uterine cancer, or stomach cancer.

In some embodiments, the cancer is non-small cell lung cancer.

In some embodiments, the cancer is breast cancer.

In some embodiments, the Compound (A) is provided as a succinate salt for the treatment of disorders associated with mutant EGFR or mutant HER2.

In some embodiments, the Compound (A) is provided as polymorphic Form-I of a succinate salt for the treatment of disorders associated with mutant EGFR or mutant HER2.

In some embodiments, the treatment of disorders associated with mutant EGFR or mutant HER2 further comprises achieving a plasma concentration, $C_1$, of Compound (A) in the patient at or above about 40 ng/mL during the treatment of disorders associated with mutant EGFR or mutant HER2.

In some embodiments, the plasma concentration, $C_1$, is at or above about 50 ng/ml during the treatment of disorder associated with mutant EGFR or mutant HER2.

In some embodiments, the plasma concentration, $C_1$, is maintained for at least about four hours during the treatment of disorders associated with mutant EGFR or mutant HER2.

In some embodiments, the present disclosure relates to a pharmaceutical composition comprising from about 40 mg to about 200 mg of Compound (A) or a pharmaceutically acceptable salt thereof.

In some embodiments, the pharmaceutical composition comprises from about 20 mg to about 160 mg of Compound (A) or a pharmaceutically acceptable salt thereof.

In some embodiments, the pharmaceutical composition comprises about 20 mg, about 40 mg, about 60 mg, about 80 mg, about 120 mg, or about 160 mg of Compound (A) or a pharmaceutically acceptable salt thereof.

In some embodiments, the pharmaceutical composition comprises about 40 mg of Compound (A) or a pharmaceutically acceptable salt thereof.

In some embodiments, the pharmaceutical composition comprises one or more capsules or tablets.

In some embodiments, the pharmaceutical composition comprises one or more capsules, wherein the one or more capsules contain Compound (A) or a pharmaceutically acceptable salt thereof without any excipient.

In some embodiments, the pharmaceutical composition comprises a succinate salt of Compound (A).

In some embodiments, the pharmaceutical composition comprises polymorphic Form-I of a succinate salt of Compound (A).

DETAILED DESCRIPTION

Definitions

Figure 1:
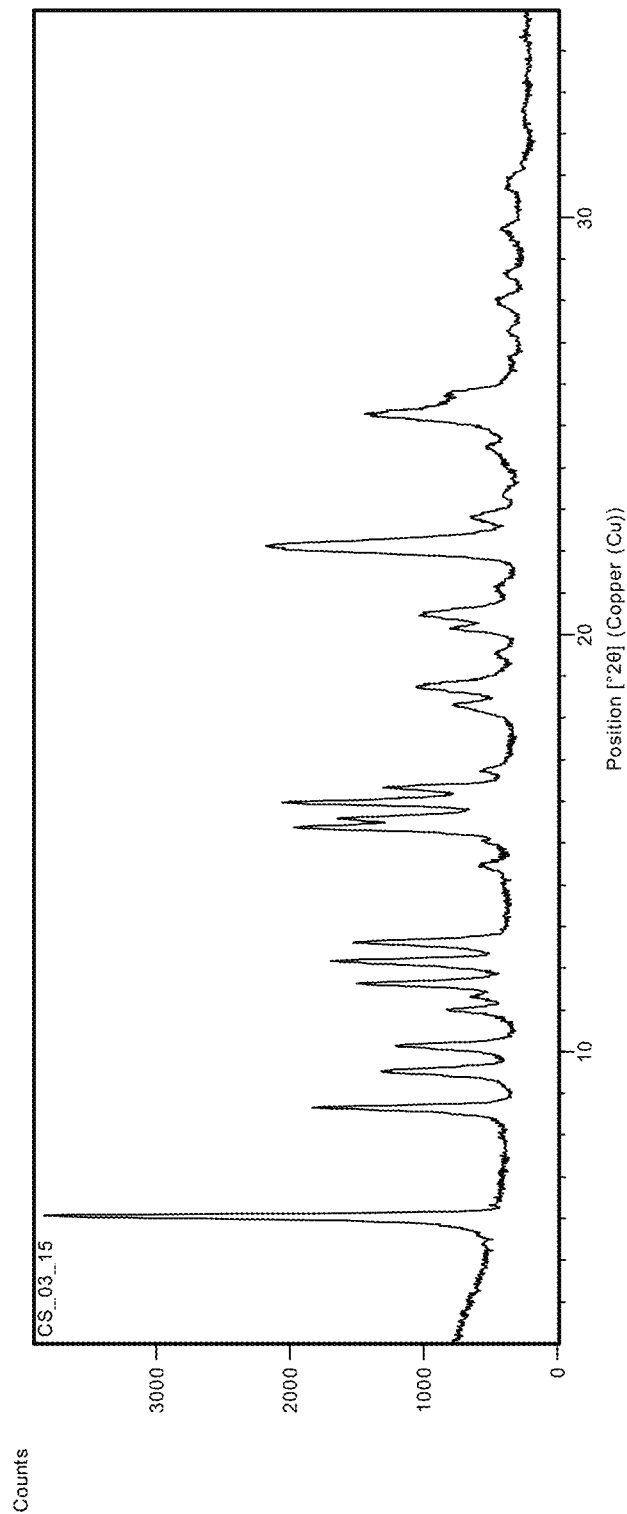
FIG. 1 is XRPD data for the polymorphic Form-I of the anhydrous free base of Compound (A).

Unless defined otherwise, all technical and scientific terms used herein have the same meaning as commonly understood by one of ordinary skill in the art to which this invention belongs. Accordingly, the following terms are intended to have the following meanings:

As used in the specification and claims, the singular form "a", "an" and "the" includes plural references unless the context clearly dictates otherwise.

As used herein, "QD" refers to once daily and "BID" refers to twice daily.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide active compounds, such as plant or animal extracts, and the like. A skilled artisan can readily recognize that there is no limit as to the structural nature of the agents of this disclosure.

As used herein, "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of that target protein or polypeptide are also specifically included within this definition. Non-limiting examples of biological activity inhibited by an antagonist include those associated with the development, growth, or spread of a tumor, or an undesired immune response as manifested in autoimmune disease.

As used herein, "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

As used herein, "cell proliferation" refers to a phenomenon by which the cell number has changed as a result of cell division. This term also encompasses cell growth by which the cell morphology has changed (e.g., increased in size) consistent with a proliferative signal.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, "co-administration," "administered in combination with," and their grammatical equivalents, as used herein, encompasses administration of two or more agents to a subject such that both agents and/or their metabolites are present in the subject at the same time. Co-administration includes simultaneous administration in separate compositions, administration at different times in separate compositions, or administration in a single fixed dose composition in which both agents are present.

As used herein, "selective inhibition" or "selectively inhibit" as applied to a biologically active agent refers to the agent's ability to selectively reduce the target signaling activity as compared to off-target signaling activity, via direct or indirect interaction with the target. For example, a compound that selectively inhibits exon 20 mutant EGFR over wild-type EGFR has an activity of at least about 2× against the mutated EGFR relative to the compound's activity against the wild-type EGFR isoform (e.g., at least about 3×, about 5×, about 10×, about 20×, about 50×, or about 100×).

As used herein, "in vivo" refers to an event that takes place in a subject's body. In vivo also includes events occurring in rodents, such as rats, mice, guinea pigs, and the like.

As used herein, "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

As used herein, a "mutant EGFR-mediated disorder" refers to a disease or condition involving an aberrant EGFR-mediated signaling pathway associated with the EGFR having one or more mutations in any of its exons and includes having one or more mutations in the exon 20 domain. In one embodiment, the mutant EGFR has one or more mutations in the exon 20 domain. In some embodiments, the mutant EGFR-mediated disorder can be associated with EGFR having one or more mutations in the exon 20 domain.

As used herein, a "mutant HER2-mediated disorder" refers to a disease or condition involving an aberrant HER2-mediated signaling pathway associated with the HER2 having one or more mutations in any of its exons and includes having one or more mutations in the exon 20 domain. In one embodiment, the mutant HER2 has one or more mutations in the exon 20 domain. In some embodiments, the mutant HER2-mediated disorder can be associated with HER2 having one or more mutations in the exon 20 domain.

As used herein, "therapeutic effect" encompasses a therapeutic benefit as described above. A "prophylactic effect" includes delaying or eliminating the appearance of a disease or condition, delaying or eliminating the onset of symptoms of a disease or condition, slowing, halting, or reversing the progression of a disease or condition, or any combination thereof.

As used herein, "effective amount" or "therapeutically effective amount" refers to that amount of a compound or pharmaceutical composition described herein that is sufficient to effect the intended application including, but not limited to, disease treatment, as illustrated below. In some embodiments, the amount that is effective for detectable killing or inhibition of the growth or spread of cancer cells; the size or number of tumors; or other measure of the level, stage, progression or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of cell migration. The specific dose will vary depending on, for example, the particular compounds chosen, the species of the subject and their age/existing health conditions or risk for health conditions, the dosing regimen to be followed, the severity of the disease, whether it is administered in combination with other agents, timing of administration, the tissue to which it is administered, and the physical delivery system in which it is carried.

The terms "treatment", "treating", "palliating", "managing" and "ameliorating" are used interchangeably herein. These terms refer to an approach for obtaining beneficial or desired results including, but not limited to, therapeutic benefit. The term "therapeutic benefit' refers to the eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For a "prophylactic benefit", the pharmaceutical compounds and/or compositions can be administered to a patient at risk of developing a particular disease, or to a patient reporting one or more of the physiological symptoms of a disease, even though a diagnosis of this disease may not have been made.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "pharmaceutically acceptable form" includes, but is not limited to, pharmaceutically acceptable salts, hydrates, solvates, isomers, prodrugs, stereoisomers, and polymorphic forms.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

In certain embodiments, the pharmaceutically acceptable salt is a succinate salt, fumarate salt, hippurate salt, oxalate salt, mesylate salt, tosylate salt, sulfate salt, hydrochloride salt, or hydrobromide salt.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The term "pharmaceutically acceptable carrier" or "pharmaceutically acceptable excipient" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; selfemulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

The term "polymorphic form" or "crystalline" refers to a solid in which the constituent atoms, molecules, or ions are packed in a regularly ordered, repeating three-dimensional pattern having a highly regular chemical structure. In particular, a crystalline compound or salt might be produced as one or more crystalline forms. For the purposes of this application, the terms "polymorphic form", "polymorph" or "crystalline form" are synonymous.

The term "solution" refers to a solvent containing a substance(s) that is at least partially dissolved; and which may contain undissolved substance(s).

The term "XRPD" refers to X-ray powder diffraction pattern. A discussion of the theory of XRPD can be found in Stout & Jensen, X-Ray Structure Determination; A Practical Guide, MacMillan Co., New York, N. Y. (1968).

The terms "room temperature" and "ambient temperature" are used interchangeably herein. These terms refer to the temperature of the surrounding environment.

The term "hydrate" refers to a solvate wherein the solvent molecule is $H_2O$ that is present in a defined stoichiometric amount, and includes, for example, hemihydrates, monohydrates, dihydrates, and trihydrates.

The term "seeding" or "seeding material" refers to the addition of a small amount of a crystalline material to a solution or mixture to initiate crystallization.

"Alkyl" refers to a straight or branched saturated hydrocarbon chain radical consisting solely of carbon and hydrogen atoms. Examples include, but are not limited to, methyl, ethyl, propyl (n-propyl, isopropyl), butyl (n-butyl, sec-butyl, isobutyl, tert-butyl), etc. Alkyl groups typically contain 1-10 carbon atoms, such as 1-6 carbon atoms, preferably 1-3 or 1-4 carbon atoms, and can be substituted or unsubstituted. Suitable substituents include, but not limited to, amino, heterocycloalkyl, hydroxy, methoxy, ethoxy, propoxy, isopropoxy, butoxy, t-butoxy, $NO_2$, CN, oxo, acyl, F, Cl, Br, etc.

"Amino" refers to a —NRR group, where each R is independently selected from 1 hydrogen and alkyl.

"Heterocycloalkyl" refers to any 5 to 6-membered non-aromatic rings, which may be saturated or unsaturated, can be substituted or unsubstituted, and which contains, in addition to carbon atom(s), at least one heteroatom, such as nitrogen, oxygen, phosphorous, or sulfur. Examples include, but are not limited to, tetrahydrofuranyl, dihydrofuranyl, pyrrolidinyl, 1-methylpyrrolidinyl, tetrahydrothiophenyl, dihydrothiophenyl, dihydropyrrolyl and pyrrolyl-2,5-dione, pyrazolinyl, piperidyl, or piperazinyl. In some embodiments, heterocycloalkyl contains, in addition to carbon atom(s), at least one nitrogen. A nitrogen containing heterocycloalkyl can be optionally oxidized or quaternized. Suitable substituents include, but not limited to, amino, alkyl, hydroxy, methoxy, ethoxy, propoxy, isopropoxy, butoxy, t-butoxy, $NO_2$, CN, oxo, acyl, F, Cl, Br, etc.

Compound (A)

Compound (A) has the following structure:

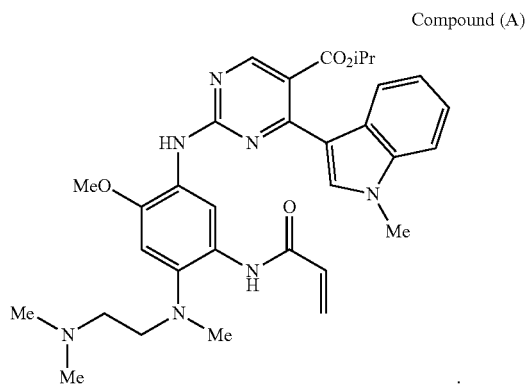

Compound (A)

The chemical name for Compound (A) is propan-2-yl 2-[5-(acryloylamino)-4-{[2-(dimethylamino)ethyl](methyl)amino}-2-methoxyanilino]-4-(1-methyl-1H-indol-3-yl)pyrimidine-5-carboxylate.

In some embodiments; Compound (A) is provided as a free base.

In some embodiments, Compound (A) is provided as polymorphic Form-I of a free base.

In some embodiments, Compound (A) is provided as a succinate salt of Compound (A).

In some embodiments, Compound (A) is provided as a polymorphic form of the succinate salt of Compound (A).

In some embodiments, Compound (A) is provided as polymorphic Form-I of the succinate salt of Compound (A).

In some embodiments, Compound (A) is provided as a pharmaceutically acceptable form, e.g., pharmaceutically acceptable salts, hydrates, solvates, isomers, or prodrugs.

Compound (A) or pharmaceutically acceptable salts, hydrates, solvates, isomers, or prodrugs, thereof may be produced according to the methods described in WO 2015/195228, which is incorporated herein by reference in its entirety.

Compound (A), as a freebase, succinate salt, or polymorphic Form-I (of the freebase or succinate salt) can be prepared according to Examples 1 and 2.

Processes for Preparing EGFR Inhibitors

In certain embodiments, the present disclosure provides a processes for preparing pyrimidine derivatives of formula (I) as outlined in Scheme I.

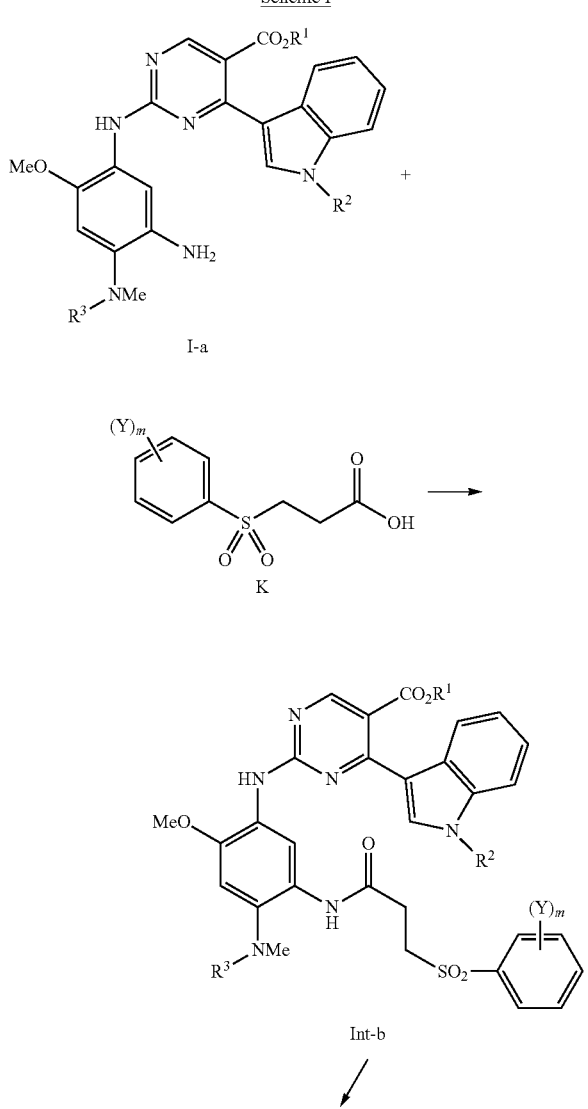

-continued

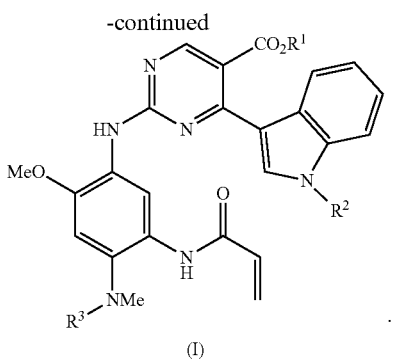

(I)

Scheme I shows a general route for the preparation of compounds of formula (I). The method comprises:
(i) preparing a mixture of a compound of formula (I-a) and a phenylsulfonyl propanoic acid of formula (K) in the presence of a solvent at a temperature from about −10° C. to about 10° C.;
(ii) adding a coupling reagent to the reaction mixture of step (i) to form a compound of formula Int-b;
(iii) optionally the product of step (ii) is washed with a suitable solvent such as ethanol and isolated by filtration; and
(iv) treating the product of step (ii) or (iii) with a base to generate a compound of formula (I).

In certain embodiments, a compound of formula (I) may be purified according to the method comprising:
(a) dissolving or suspending a compound of formula (I) in a solvent;
(b) optionally filtering the solution of step (a);
(c) heating the solution of step (a) or (b) at a temperature of between about 50° C. to 80° C.;
(d) optionally filtering the solution of step (c);
(e) cooling the product of step (d); and
(f) isolating the solids of step (e).

In certain embodiments, the solvent in step a) comprises ethyl acetate, isopropyl acetate, tetrahydrofuran, methyl tetrahydrofuran, dioxane, dichloromethane, or acetonitrile.

In certain embodiments of Scheme I, $R^1$ is alkyl; $R^2$ is H or alkyl; $R^3$ is alkyl substituted with an amino or heterocycloalkyl; Y is $CH_3$, Cl, Br, F, or $OCH_3$; and m is 0, 1, 2, 3, 4, or 5.

In certain embodiments of Scheme I, $R^1$ is methyl, ethyl, propyl, or butyl; $R^2$ is H, methyl, ethyl, propyl, or butyl; and $R^3$ is methyl, ethyl, propyl, or butyl, each of which is substituted with an amino or a heterocycloalkyl; amino is $NR^4R^5$; $R^4$ and $R^5$ are independently H or alkyl; heterocycloalkyl is pyrrolidin-2-yl or 1-methylpyrrolidin-2-yl; Y is $CH_3$, Cl, Br, F, or $OCH_3$; and m is 0, 1, 2, 3, 4, or 5.

In certain embodiments of Scheme I, $R^1$ is isopropyl; $R^2$ is H or methyl; $R^3$ is ethyl substituted with $NR^4R^5$; $R^4$ and $R^5$ are independently H or methyl; or $R^3$ is methyl substituted with pyrrolidin-2-yl or 1-methylpyrrolidin-2-yl; and m is 0.

In certain embodiments of formula (I) in Scheme I, $R^1$ is isopropyl; $R^2$ is methyl; $R^3$ is ethyl substituted with $NR^4R^5$; and $R^4$ and $R^5$ are methyl.

In certain embodiments of formula (I) in Scheme I, $R^1$ is isopropyl; $R^2$ is H; $R^3$ is ethyl substituted with $NR^4R^5$; and $R^4$ and $R^5$ are methyl.

In certain embodiments of formula (I) in Scheme I, $R^1$ is isopropyl; $R^2$ is methyl; $R^3$ is ethyl substituted with $NR^4R^5$; $R^4$ is H; and $R^5$ is methyl.

As shown in Scheme I, a compound of formula (I-a) is mixed with a phenylsulfonyl propanoic acid of formula (K). Compounds of formula (K) may be obtained from commercially available sources or prepared according to the methods known to one of ordinary skilled in the art. Suitable solvents in step (i) can be dichloromethane (DCM), tetrahydrofuran (THF), 2-methyl tetrahydrofuran (2-MeTHF), isopropyl acetate (IPAc), cyclopentyl methyl ether (CPME), and dioxane. In one embodiment, the suitable solvent is anhydrous dichloromethane. The mixture of step (i) is cooled to a temperature of below about 10° C., such as about 8° C., about 5° C., about 2° C., about 0° C., about −5° C., or about −10° C.

In step (ii), while maintaining the internal temperature below about 10° C., the mixture is treated with a base such as an amine and then a coupling reagent is added to the mixture to form a compound of formula Int-b. Bases in step (ii) comprise N,N-diisopropylethylamine (DIEA), triethylamine (TEA), 1,8-diazabicyclo(5.4.0)undec-7-ene (DBU), 1,5-diazabicyclo(4.3.0)non-5-ene (DBN), and N-methyl-2-pyrrolidinone (NMP).

Suitable coupling reagents can be propylphosphonic anhydride (T3P), thionyl chloride ($SOCl_2$), N,N'-diisopropyl carbodiimide (DIC), carbonyldiimidazole (CDI), phosgene ($COCl_2$), or 1-Ethyl-3-(3-dimethylaminopropyl)carbodiimide (EDC).

In certain embodiment, the coupling reagent is propylphosphonic anhydride.

In one embodiment, the coupling reagent is a solution comprising 50% w/w propylphosphonic anhydride and a solvent such as THF, 2-MeTHF, IPAc, CPME, or dioxane.

In step (iii), the compound of formula Int-b is treated with a base. Depending on the base used, the temperature for step (iii) can vary from about −10° C. to about 90° C.

In certain embodiments, the base in step (iii) is potassium trimethylsilanolate ($KOSi(CH_3)_3$) to provide a compound of formula (I). The reaction may be conducted at a temperature from about −5° C. to about 5° C., such as about −5° C. to about 0° C., about 0° C. to about 2° C., or about 2° C. to about 5° C., in the presence of a solvent such as tetrahydrofuran, acetonitrile (MeCN), acetone, 2-MeTHF, dimethyl sulfoxide (DMSO), dimethyl formamide (DMF), or dimethyl acetamide (DMAc).

In certain embodiments, the base in step (iii) is selected from NaOH, DBU, KOt-Bu, NaOt-Bu, LiOt-Bu, DBN, KOH, and LiOH at a temperature from about 40° C. to about 90° C., such as about 50° C. to about 60° C., about 60° C. to about 70° C., about 70° C. to about 80° C., or about 80° C. to about 90° C. in the presence of a solvent such as tetrahydrofuran, MeCN, acetone, 2-MeTHF, DMSO, DMF, DMAc.

In one embodiment, the present disclosure provides a process for preparing a pyrimidine derivative of Compound (A) as described in Scheme II.

Scheme II

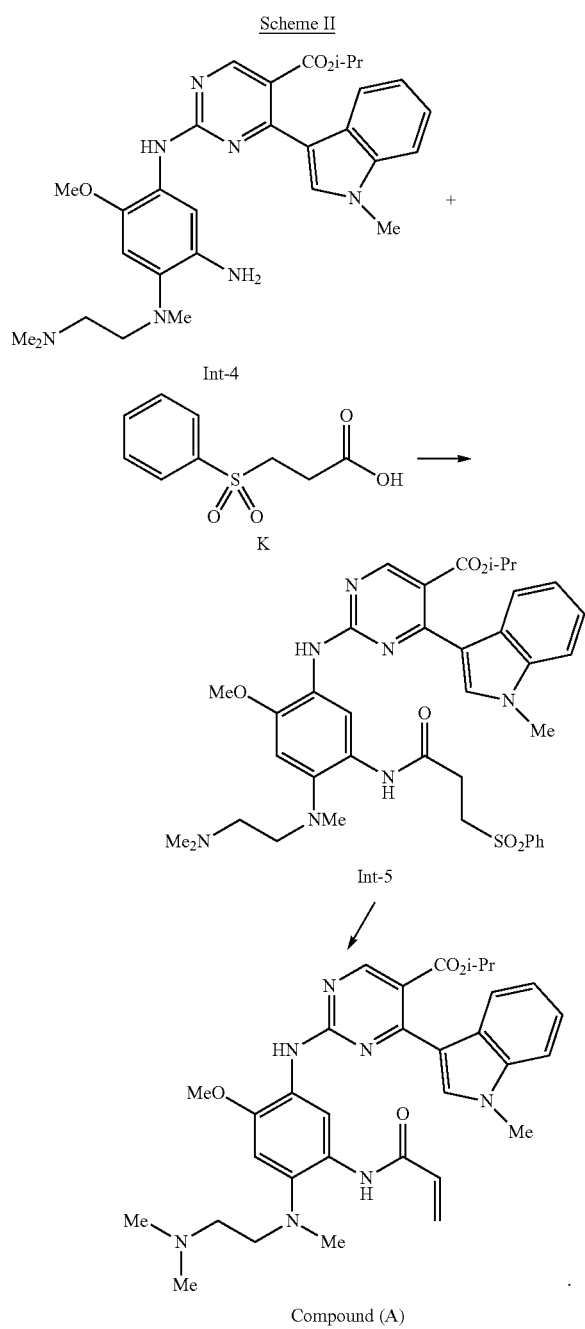

In Scheme II, compound (Int-4) is combined with a phenylsulfonyl propanoic acid of formula (K). The mixture is prepared in the presence of a solvent at a temperature from about −10° C. to about 50° C., such as about −10° C. to about −5° C., about −5° C. to about 0° C., about 0° C. to about 5° C., about 5° C. to about 10° C., about 10° C. to about 20° C., about 20° C. to about 30° C., about 30° C. to about 40° C., or about 40° C. to about 50° C.

While maintaining the temperature below about 10° C., a base such as an amine including, but not limited to, N,N-diisopropylethylamine, TEA, DBU, DBN, or NMP is added to the mixture followed by adding a coupling reagent such as propylphosphonic anhydride (T3P), $SOCl_2$, DIC, CDI, $COCl_2$ or EDC to form compound (Int-5). Compound (Int-5) is treated with a base such as $KOSi(CH_3)_3$ to provide Compound (A). The reaction may be conducted at a temperature from about −5° C. to about 5° C., such as about −5° C. to about 0° C., about 0° C. to about 2° C., or about 2° C. to about 5° C., in the presence of a solvent such as tetrahydrofuran, MeCN, acetone, 2-MeTHF, DMSO, DMF, DMAc.

In certain embodiments, Compound (A) is prepared by treating (Int-5) with a base selected from NaOH, DBU, KOt-Bu, NaOt-Bu, LiOt-Bu, DBN, KOH, and/or LiOH at a temperature from about 40° C. to about 90° C., such as about 50° C. to about 60° C., about 60° C. to about 70° C., about 70° C. to about 80° C., or about 80° C. to about 90° C. in the presence of a suitable solvent such as tetrahydrofuran, MeCN, acetone, 2-MeTHF, DMSO, DMF, DMAc.

In certain embodiments, Compound (A) may be purified according to the method comprising:
(a) dissolving or suspending a compound of formula (I) in a solvent;
(b) optionally filtering the solution of step (a);
(c) heating the solution of step (a) or (b) at a temperature of between about 50° C. to 80° C.;
(d) optionally filtering the solution of step (c);
(e) cooling the product of step (d); and
(f) isolating the solids of step (e).

In certain embodiments, the purified Compound (A) is in a substantially crystalline form.

In certain embodiments, the purified Compound (A) is crystalline polymorphic Form-I.

In certain embodiments, the solvent in step (a) is ethyl acetate.

In certain embodiments, the solvent in step (a) is isopropyl acetate.

In certain embodiments, the solvent in step (a) is tetrahydrofuran or methyl tetrahydrofuran.

In certain embodiments, the solvent in step (a) is dioxane.

In certain embodiments, the solvent in step (a) is dichloromethane.

In certain embodiments, the solvent in step (a) is acetonitrile.

In certain embodiments, the mixture solution of step (a) or (b) is heated to a temperature of between about 60° C. to 75° C.

In certain embodiments, filtering of step (d) is conducted at a temperature of between about 50° C. to 80° C.

In certain embodiments, filtering of step (d) is conducted at a temperature of between about 60° C. to 75° C.

In certain embodiments, product of step (e) is cooled to a temperature of between about 10° C. to 0° C.

In certain embodiments, the solid in step (f) is isolated by filtration, optionally washed with a suitable solvent such as EtOH and dried under vacuum to provide purified Compound (A).

The compound of formula (I) and Compound (A) are capable of inhibiting mutant EGFR proteins. They may be prepared according to methods described in WO 2015/195228, which is incorporated herein by reference in its entirety. In WO 2015/195228, the preparation of pyrimidine derivatives of formula (I) utilizes an acrylic acid. Acrylic acid has the formula $CH_2$=CHCOOH. Acrylic acid readily polymerizes in storage. As such, this method requires fractional distillation before use. Moreover, the product needs to be purified through chromatography. Thus, this purification process limits the large scale production.

The manufacturing of a pharmaceutical composition poses many challenges to chemists and chemical engineers. One of many of these challenges relates to the handling of large quantities of reagents and control of large-scale reactions, the handling of the final product poses special challenges linked to the nature of the final active product itself. The ideal processes are those that the products can be prepared in high yield and are capable of ready isolation.

The present disclosure provides a two-step process, i.e. amide formation and elimination using a commercially available sulfonylpropionic acid. Each step provides solid compound with an isolated yield of >90%. The process eliminates the chromatograph purification. The resulting product is capable of ready isolation from crystallization to afford stable crystalline forms, which ensures consistent processing parameters and pharmaceutical quality.

Pharmaceutical Salts and Preparations

Although the free base of a compound of formula (I) or Compound (A) is effective in inhibiting mutant EGFR proteins, it may be administered in the form of a pharmaceutical salt. A suitable salt provides good solubility, good stability, and non-hygroscopicity, all of which are the properties that must be considered for drug preparations. The stability of the active ingredient is critical during each step of the manufacturing process, including bulk storage, design formulations for administration, long-term storage, etc. Each of these steps may be impacted by various environmental conditions of temperature and humidity.

In certain embodiments, the present disclosure provides pharmaceutical salts of a compound of formula (I) or Compound (A). Non-limiting examples of such salts include hydrochloric salt, hydrobromic salt, sulfate, tosylate, mesylate, oxalate, fumarate, hippurate, succinate, benzenesulfonate, ethanesulfonate, glutarate, ketoglutanate, L-tartarate, citrate, malate, benzoate, adipate, propionate, acetate, phosphate, ascorbate, gluconate, lactate, and malonate.

In certain embodiments, non-limiting examples of such salt include hydrochloric salt, hydrobromic salt, sulfate, tosylate, mesylate, oxalate, fumarate, hippurate, and succinate.

In certain embodiments, the non-limiting example is succinate.

In certain embodiments, the non-limiting example is fumarate.

Pharmaceutical salts of a compound of formula (I) may be prepared according to procedures known to one of ordinary skill in the art. Alternatively, a compound of formula (I) can be first combined with an acid in the presence of a solvent. The mixture can be heated to a temperature from about 30° C. to about 100° C., such as about 25° C. to about 50° C., about 35° C. to about 55° C., about 45° C. to about 55° C., about 50° C. to about 75° C., about 50° C. to about 100° C., and about 60° C. to about 85° C. After stirring the mixture for a sufficient time, such as from about 1 hour to about 5 hours, it can then be cooled to a temperature of the surrounding environment or to a temperature below 10° C., such as about 0° C. to about the room temperature, about 0° C. to about 10° C., and about 15° C. to about the room temperature.

In certain embodiments, the solvent can be an alcohol such as methanol, ethanol, isopropyl alcohol, or butanol. In other embodiments, the solvent can be a non-alcoholic solvent, including, but not limited to, DCM, EtOAc, THF, diethyl ether, acetone, heptane, or acetonitrile. In a further embodiment, the solvent can be a mixture of two or more of any of the aforementioned solvents.

In certain embodiments, Compound (A) can be combined with hydrochloric acid, hydrobromic acid, sulfuric acid, p-toluenesulfonic acid, methanesulfonic acid, oxalic acid, fumaric acid, hippuric acid, or succinic acid to form corresponding salts.

In certain embodiments, described herein is hydrochloric salt of Compound (A).

In certain embodiments, described herein is hydrobromic salt of Compound (A).

In certain embodiments, described herein is sulfate salt of Compound (A).

In certain embodiments, described herein is tosylate salt of Compound (A).

In certain embodiments, described herein is mesylate salt of Compound (A).

In certain embodiments, described herein is oxalate salt of Compound (A).

In certain embodiments, described herein is fumarate salt of Compound (A).

In certain embodiments, described herein is hippurate salt of Compound (A).

In certain embodiments, described herein is succinate salt of Compound (A).

In certain embodiments, described herein is monosuccinate salt of Compound (A).

In certain embodiments, described herein is anhydrate monosuccinate salt of Compound (A).

Scheme III outlines a method for preparing monosuccinate salt of Compound (A).

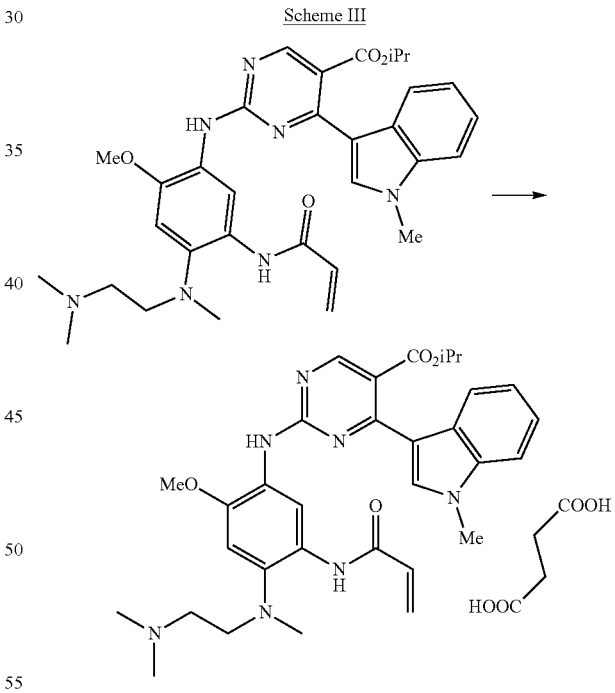

Scheme III comprises the following steps:
(a) mixing Compound (A) with succinic acid in the presence of a solvent,
(b) heating the mixture of step (a),
(c) optionally, polish filtering the mixture of step (b),
(d) optionally, adding a seeding material to the mixture of step (b) or (c),
(e) optionally thermal cycling the mixture,
(f) cooling the mixture,
(g) collecting of solids, and
(h) drying the solids.

In certain embodiments, the solvent in step (a) is acetone, acetone/water (3:1), acetonitrile, anisole, methanol, ethanol, propanol, 1-butanol, dimethylacetamide, dimethylformamide, dimethylsulfoxide, 1,4-dioxane, ethyl acetate, a mixture of methanol and water (3:1), 2-methoxyethanol, methyltetrahydrofuran, tetrahydrofuran, a mixture of tetrahydrofuran and water (3:1), a mixture of methyltetrahydrofuran and water (96:4), methyl acetate, methylethyl ketone, methyl isobutyl ketone, N-methyl-2-pyrrolidone, or a mixture thereof.

In certain embodiments, the solvent in step (a) is an alcohol, such as methanol, ethanol, propanol, or 1-butanol.

In certain embodiments, the solvent in step (a) is ethanol.

In certain embodiments, the solvent in step (a) is anisole.

In certain embodiments, the solvent in step (a) methylethyl ketone.

In certain embodiments, the solvent in step (a) is ethyl acetate.

In certain embodiments, the solvent in step (a) is tetrahydrofuran or methyl tetrahydrofuran.

In step (b), the mixture of step (a) is heated to a temperature of from about 30° C. to about 100° C.

In certain embodiments, the mixture of step (a) is heated to a temperature of from about 35° C. to about 55° C.

In certain embodiments, the mixture of step (a) is heated to a temperature of from about 45° C. to about 55° C.

In certain embodiments, the mixture of step (a) is heated to a temperature of from about 50° C. to about 75° C.

In certain embodiments, the mixture of step (b) is optionally polish filtrated to remove unwanted particulates from the bulk solution.

In certain embodiments, a small amount of seeding material is added to the mixture of step (b), or mixture of step (c) when step (c) is utilized.

The resulting mixture is then optionally placed under the "thermal cycling" condition for a period of time.

The term "thermal cycling" refers to the alternate heating and cooling of the mixture at a predetermined rate, such as 1° C. per minute, 2° C. per minute, 3° C. per minute, 5° C. per minute, 10° C. per minute, etc.

In certain embodiments, thermal cycling is at the rate of from about 0.1 to about 0.5° C. per minute.

In certain embodiments, thermal cycling is at the rate of from about 0.1 to about 0.3° C. per minute.

In certain embodiments, thermal cycling is at the rate of from about 0.2 to about 0.3° C. per minute.

In certain embodiments, thermal cycling is at the rate of from about 0.2 to about 0.4° C. per minute.

In certain embodiments, thermal cycling is at the rate of from about 0.3 to about 0.5° C. per minute.

After thermal cycling the mixture for a period of time, such as from about 1 hour to about 5 hours, the mixture is cooled to a temperature of the surrounding environment or to a temperature below 10° C. and the solid succinate salt is collected by filtration.

In certain embodiments, the succinate salt of Compound (A) may be prepared according to the method comprising:
(i) mixing Compound (A) with succinic acid in the presence of a solvent;
(ii) heating the mixture of step (i) at a temperature of from ambient temperature to about 80° C., or about 70° C., or to about 40° C.,
(iii) optionally, polish filtering the mixture of step,
(iv) optionally, adding a small amount of a crystalline succinate salt as a seeding material to the mixture,
(v) optionally thermal cycling the mixture at a temperature of between 40° C.-80° C., or between 40° C.-80° C., or between ambient and 40° C.,
(vi) cooling the reaction mixture of step (v) to or below the ambient temperature; and
(vii) collecting solids to provide succinate salt of Compound (A).

In certain embodiments, the succinate salt of Compound (A) is prepared according to Scheme III is in a substantially crystalline form characterized as polymorphic Form-I.

In certain embodiments, the solvent of step (i) is acetone, acetone/water (3:1), acetonitrile, anisole, methanol, ethanol, propanol, 1-butanol, dimethylacetamide, dimethylformamide, dimethylsulfoxide, 1,4-dioxane, ethyl acetate, methanol and water (3:1), 2-methoxyethanol, tetrahydrofuran, tetrahydrofuran and water (3:1), methyltetrahydrofuran, methyltetrahydrofuran and water (96:4), methyl acetate, methylethyl ketone, methyl isobutyl ketone, N-methyl-2-pyrrolidone, or a mixture thereof.

In certain embodiments, the solvent is ethanol.

In certain embodiments, the solvent is methyltetrahydrofuran.

In certain embodiments, the solvent is anisole.

In certain embodiments, the solvent is methylethyl ketone.

Polymorphic Forms and the Preparations

In certain embodiments, the present disclosure provides free base Compound (A) in a substantially crystalline form.

In certain embodiments, the present disclosure provides the hydrochloric salt, hydrobromic salt, sulfate salt, tosylate salt, mesylate salt, oxalate salt, fumarate salt, hippurate salt and succinate salts of Compound (A) in a substantially crystalline form.

In certain embodiments, the present disclosure provides the succinate salt of Compound (A) in a substantially crystalline form.

In certain embodiments, the present disclosure provides the fumarate salt of Compound (A) in a substantially crystalline form.

The term "substantially crystalline form" refers to at least a particular percentage by weight of Compound (A) or its salts are crystalline. Particular weight percentages include at least about 50%, 60%, 70%, 75%, 80%, 85%, 87%, 88%, 89%, 90%, 91%, 92%, 93%, 94%, 95%, 96%, 97%, 98%, 99%, 99.5% and 99.9%.

When a crystalline form of a compound is identified using one or more XRPD peaks given as angles 2θ, each of the 2θ values is understood to mean the given value±0.2 degrees, unless otherwise expressed, for example as the given value±0.3.

When a crystalline form of a compound is identified using one or more temperatures from a DSC profile (e.g., onset of endothermic transition, melt, etc.), each of the temperature values is understood to mean the given value±2° C., unless otherwise expressed.

In certain embodiments, the present disclosure provides polymorphic Form-I of free base Compound (A).

In some embodiments, polymorphic Form-I of free base Compound (A) has an X-ray powder diffraction pattern having characteristic peaks expressed in degrees two-theta at approximately 6.1±0.20, 15.4±0.20, 16.0±0.20, and 22.1±0.20 degrees.

In some embodiments, polymorphic Form-I of free base Compound (A) has an X-ray powder diffraction pattern having characteristic peaks expressed in degrees two-theta at approximately 6.1±0.20, 8.7±0.20, 12.2±0.20, 12.6±0.20, 15.4±0.20, 15.6±0.20, 16.0±0.20, 22.1±0.20, and 25.3±0.20, degrees.

In some embodiments, polymorphic Form-I of free base Compound (A) has an X-ray powder diffraction pattern having characteristic peaks expressed in degrees two-theta at approximately 6.1±0.20, 8.7±0.20, 9.5±0.20, 10.1±0.20, 11.6±0.20, 12.2±0.20, 12.6±0.20, 15.4±0.20, 15.6±0.20, 16.0±0.20, 16.3±0.20, 18.7±0.20, 20.5±0.20, 22.1±0.20, and 25.3±0.20, degrees.

In certain embodiments, the present disclosure provides polymorphic Form-I of free base Compound (A) having XRPD as shown in FIG. 1.

In some embodiments, polymorphic Form-I of free base Compound (A) can be prepared by dissolving the free base in a suitable solvent, including but not limiting to, dichloromethane. The resulting solution is then filtered and evaporated to dryness to give polymorphic Form-I of free base Compound (A).

In certain embodiments, the present disclosure provides polymorphic Form-I of the succinate salt of Compound (A).

In some embodiments, polymorphic Form-I of the succinate salt of Compound (A) has an X-ray powder diffraction pattern having characteristic peaks expressed in degrees two-theta at approximately 8.3±0.20, 9.9±0.20, 11.7±0.20, and 22.5±0.20 degrees.

In some embodiments, polymorphic Form-I of the succinate salt of Compound (A) has an X-ray powder diffraction pattern having characteristic peaks expressed in degrees two-theta at approximately 8.3±0.20, 9.9±0.20, 11.7±0.20, 14.3±0.20, 15.3±0.20, 18.6±0.20, 19.4±0.20, 21.9±0.20, 22.5±0.20, and 25.2±0.20 degrees.

In some embodiments, polymorphic Form-I of the succinate salt of Compound (A) has an X-ray powder diffraction pattern having characteristic peaks expressed in degrees two-theta at approximately 8.3±0.20, 9.9±0.20, 11.4±0.20, 11.7±0.20, 14.3±0.20, 15.3±0.20, 18.6±0.20, 19.4±0.20, 19.9±0.20, 21.9±0.20, 22.5±0.20, 22.8±0.20, 23.8±0.20, 25.2±0.20, and 25.6±0.20 degrees.

Figure 4:
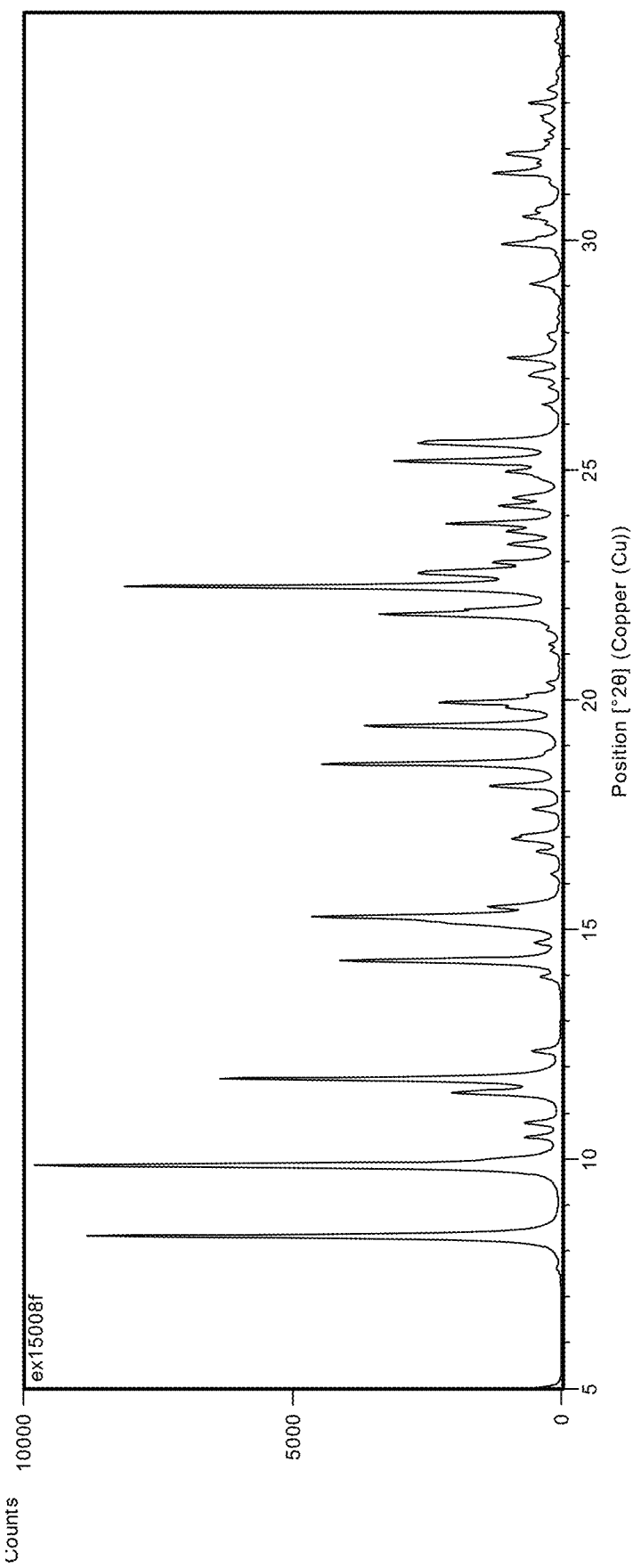
FIG. 4 is XRPD data for the polymorphic Form-I of the succinate salt of Compound (A).

In some embodiments, polymorphic Form-I of the succinate salt of Compound (A) has an X-ray powder diffraction pattern having characteristic peaks expressed in degrees two-theta as shown in FIG. 4.

In some embodiments, polymorphic Form-I of the succinate salt of Compound (A) can be prepared according to the following method:
1) mixing succinate salt of Compound (A) with a solvent or solvent mixture,
2) heating or thermal cycling the mixture,
3) optionally, adding a small amount of the polymorphic Form-I of the succinate salt of Compound (A) as seeding material,
4) stirring the mixture solution,
5) cooling the mixture, and
6) collecting the crystalline.

In certain embodiments, the solvent in step (1) is acetone, acetone/water (3:1), acetonitrile, anisole, methanol, ethanol, propanol, 1-butanol, dimethylacetamide, dimethylformamide, dimethylsulfoxide, 1,4-dioxane, ethyl acetate, methanol and water (3:1), 2-methoxyethanol, tetrahydrofuran, tetrahydrofuran and water (3:1), methyltetrahydrofuran, methyltetrahydrofuran and water (96:4), methyl acetate, methylethyl ketone, methylethyl ketone, methyl isobutyl ketone, N-methyl-2-pyrrolidone, or a mixture thereof.

In certain embodiments, the solvent is ethanol.
In certain embodiments, the solvent is ethyl acetate.
In certain embodiments, the solvent is acetone.
In certain embodiments, the solvent is acetonitrile.
In certain embodiments, the solvent is tetrahydrofuran or methyl tetrahydrofuran.

In certain embodiments, the mixture is heated to a temperature from about 30° C. to about 100° C., such as about 35° C. to about 55° C., about 45° C. to about 55° C., or about 50° C. to about 75° C.

Alternatively, the mixture is placed under a thermal cycling condition at a rate about 1° C. per minute, or 2° C. per minute, or 3° C. per minute between a temperature from about 30° C. to about 100° C., such as about 50° C. to about 75° C. After a sufficient amount of time, such as from about 1 hour to about 5 hours, the reaction mixture is cooled to a temperature of the surrounding environment or to a temperature below 10° C. and the crystalline succinate salt is collected by filtration.

In certain embodiments, thermal cycling is at the rate of from about 0.1 to about 0.5° C. per minute, from about 0.1 to about 0.3° C. per minute, from about 0.2 to about 0.3° C. per minute, from about 0.2 to about 0.4° C. per minute, or from about 0.3 to about 0.5° C. per minute.

In some embodiments, the amount of polymorphic Form-I of the succinate salt of Compound (A) as a seeding material in the process is about from 0.1% to about 5% by weight of the non-crystalline solid. In some embodiments, the amount of polymorphic Form I as seeding material is from about 0.5% to about 1% by weight of the non-crystalline solid. In some embodiments, the amount of polymorphic Form I as seeding material is about from 1% to about 3% by weight of the non-crystalline solid. In some embodiments, the amount of crystalline Pattern B as seeding material is about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of the non-crystalline solid.

In some embodiments, step (6) for collecting the crystalline may be achieved by filtration, optionally followed by drying under reduced pressure.

In some embodiments, the sufficient amount of time for the process is from 1 hour to 24 hours. In other embodiments, the sufficient amount of time is about 4, 6, 8, 10, 12, 14, or 16 hours.

Pharmaceutical Compositions

In certain embodiments, Compound (A), or a pharmaceutically acceptable salt thereof, including the succinate salt, or the polymorphic forms can be formulated as pharmaceutical compositions for administration in solid or liquid form, including those adapted for the following: oral administration, for example, tablets, capsules, boluses, powders, granules, or pastes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

In some embodiments, pharmaceutical compositions comprises Compound (A), or a pharmaceutically acceptable salt thereof, including the succinate salt, or the polymorphic forms, and optionally one or more pharmaceutically acceptable excipients, carriers, including inert solid diluents and fillers, diluents, including sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic).

In some embodiments, the compositions comprise Compound (A) together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

In some embodiments, the compositions comprise Compound (A) filled in a capsule without any excipients. For example, Compound (A), or the succinate salt of Compound (A), or the polymorphic Form-I of the succinate salt of Compound (A) may be filled directly into hard gelatin capsules, with no excipients.

In come embodiments, the compositions may be formulated as a drug-in-capsule without excipients.

In certain embodiments, the drug-in-capsule composition comprises the succinate salt of Compound (A) that is equivalent to 20 mg of the freebase of Compound (A).

In certain embodiments, the drug-in-capsule composition comprises the polymorphic Form-I of the succinate salt of Compound (A) that is equivalent to 20 mg of the freebase of Compound (A).

In certain embodiments, the drug-in-capsule composition comprises the succinate salt of Compound (A) that is equivalent to 40 mg of the freebase of Compound (A).

In certain embodiments, the drug-in-capsule composition comprises the polymorphic Form-I of the succinate salt of Compound (A) that is equivalent to 40 mg of the freebase of Compound (A).

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon Compound (A) can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association Compound (A) and/or the chemotherapeutic with the carrier and, optionally, one or more accessory ingredients. In general, the formulations are prepared by uniformly and intimately bringing into association Compound (A) with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Dosage Forms

Compound (A), or a pharmaceutically acceptable salt thereof, including the succinate salt, or the polymorphic forms, can be delivered in the form of pharmaceutically acceptable compositions which comprise a therapeutically effective amount of Compound (A) and optionally one or more additional therapeutic agents such as a chemotherapeutic, optionally formulated together with one or more pharmaceutically acceptable excipients. In some embodiments, only Compound (A) without an additional therapeutic agent maybe included in the dosage form. In some instances, Compound (A) and the additional therapeutic agent are administered in separate pharmaceutical compositions and may (e.g., because of different physical and/or chemical characteristics) be administered by different routes (e.g., one therapeutic can be administered orally, while the other can be administered intravenously). In other instances, Compound (A) and the additional therapeutic agent may be administered separately, but via the same route (e.g., both orally or both intravenously). In still other instances, Compound (A) and the additional therapeutic agent can be administered in the same pharmaceutical composition (e.g., a fixed dose combination).

The selected dosage level will depend upon a variety of factors including, for example, the severity of the condition, the route of administration, the time of administration, the duration of the treatment, administration of other drugs, compounds and/or materials used in combination with Compound (A), the age, sex, weight, condition, general health and prior medical history of the patient being treated, and like factors well known in the medical arts.

Dose escalation studies for Compound (A) or a pharmaceutically acceptable salt thereof, including the succinate salt, are described in the Examples below. These studies were used to determine suitable doses of Compound (A) or a pharmaceutically acceptable salt thereof, including the succinate salt. As described below, disease stabilization for subjects treated with Compound (A) in a form of the succinate salt was reported in the 40 mg (freebase) QD cohort. In some embodiments, a dosage of the succinate salt of the Compound (A) is equivalent to about 40 mg, 80 mg, 120 mg, or 160 mg per day of the freebase of Compound (A). Patients were also given up to 180 mg per day and achieved a response at this dosage. Accordingly, in certain embodiments, a dosage of Compound (A), which is administered in the form of succinate salt of Compound (A), is less than about 200 mg per day. In one embodiment, the dose range is from about 40 mg to about 200 mg per day of Compound (A). In some embodiments, the dose range is from about 80 mg to about 160 mg per day of Compound (A). In some embodiments, the dose range is from about 120 mg to about 160 mg per day of Compound (A). Specific doses within these ranges include on a per day basis, 40 mg, 60 mg, 80 mg, 100 mg, 120 mg, 140 mg, 160 mg, 180 mg and 200 mg of Compound (A). In some embodiments, the dosage used herein, is administered in the form of succinate salt of the Compound (A) or in the form of polymorphic Form-I of the succinate salt of the Compound (A).

As used herein, the dose amounts (e.g., milligrams (mg)) of Compound (A) or a pharmaceutically acceptable form thereof in dosing regimens refer to the weight amount of Compound (A) as a free base. Similarly, the weight amounts of Compound (A) or a pharmaceutically acceptable form thereof in pharmaceutical compositions described herein refer to the weight amount of Compound (A) as a free base. The corresponding weight amount for a pharmaceutically acceptable form (e.g., a salt, hydrate, etc.) of Compound (A) in dosing regimens or pharmaceutical compositions may be calculated accordingly.

Actual dose levels of the active ingredients in the pharmaceutical compositions described herein can be varied so as to obtain an amount of the active ingredient that is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, Compound (A) can be administered daily, every other day, three times a week, twice a week, weekly, bi-weekly, or another intermittent schedule. The dosing schedule can include a "drug holiday," i.e., the drug can be administered for two weeks on, one week off, or three weeks on, one week on, or four weeks on, one week off, etc., or continuously, without a drug holiday. In some embodiments, Compound (A) is administered daily on a 28-day cycle. In other embodiments, Compound (A) is administered daily on a 21-day cycle. In some embodiments, Compound (A) is administered daily (e.g., once daily or twice daily) for at least three consecutive days, e.g., at least five consecutive days, at least seven consecutive days, at least 14 consecutive days, at least 21 consecutive days, or at least 28 consecutive days. Compound (A) may be administered orally, rectally, parenterally, intravenously, intraperitoneally, topically, transdermally, intramuscularly, subcutaneously, intracisternally, intravaginally, intranasally, sublingually, buccally, or by any other route.

In some embodiments, Compound (A) may be administered in multiple doses. Dosing may be about once, twice, three times, four times, five times, six times, or more than six times per day. In a preferred embodiment, dosing is once per day or twice per day. For example, the dosage of Compound (A) may be 60 mg twice daily, 80 mg twice daily, 120 mg once daily or 160 mg once daily. Dosing can be about once a month, about once every two weeks, about once a week, or about once every other day. In some embodiments, Compound (A) and another agent are administered together about once per day to about 6 times per day. For example, Compound (A) can be administered one or more times per day on a weekly basis (e.g., every Monday) indefinitely or for a period of weeks, e.g., 4-10 weeks. Alternatively, it can be administered daily for a period of days (e.g., 2-10 days) followed by a period of days (e.g., 1-30 days) without administration of the compound, with that cycle repeated indefinitely or for a given number of repetitions, e.g., 4-10 cycles. As an example, Compound (A) can be administered daily for 5 days, then discontinued for 9 days, then administered daily for another 5 day period, then discontinued for 9 days, and so on, repeating the cycle indefinitely, or for a total of 4-10 times. In some embodiments, the administration of Compound (A) and an agent continues for less than about 7 days. In yet some embodiments, the administration continues for more than about 6, about 10, about 14, about 28 days, about two months, about six months, or about one year. In some cases, continuous dosing can be achieved and maintained as long as necessary.

Administration of the pharmaceutical compositions as disclosed herein can continue as long as necessary. In some embodiments, Compound (A) can be administered for more than about 1, about 2, about 3, about 4, about 5, about 6, about 7, about 14, about 21, or about 28 days. In some embodiments, an agent as disclosed herein can be administered for less than about 28, about 21, about 14, about 7, about 6, about 5, about 4, about 3, about 2, or about 1 day. In some embodiments, Compound (A) can be administered chronically on an ongoing basis, e.g., for the treatment of chronic effects.

In some embodiments, the method further comprises achieving a plasma concentration, $C_1$, of Compound (A) in the patient. In some embodiments, $C_1$ is at or above about 20 ng/mL, e.g., at or above 30 ng/mL, at or above about 40 ng/ml, or at or above about 50 ng/mL. In some embodiments, the plasma concentration is maintained at or above a concentration, $C_1$, for at least about 4 hours, e.g., at least about 6 hours, at least about 8 hours, at least about 12 hours, at least about 18 hours, or at least about 24 hours. In some embodiments, plasma concentration does not rise above a plasma concentration, $C_2$, of Compound (A) in the patient. In some embodiments, $C_2$ is at or below about 100 ng/ml, e.g., at or below about 80 ng/mL, or at or below about 60 ng/mL. In some embodiments, plasma concentration of Compound (A) may be between about 20-100 ng/mL, about 20-80 ng/mL, about 20-60 ng/ml, about 40-100 ng/mL, about 40-80 ng/mL, about 40-60 ng/mL, about 50-100 ng/mL, about 50-80 ng/mL, or about 50-60 ng/mL and may be maintained within a range for at least about 4 hours, at least about 6 hours, at least about 8 hours, at least about 12 hours, at least about 18 hours, or at least about 24 hours. Example 4 and FIGS. 2A and B illustrate a study of the pharmacokinetics of Compound (A) provided as polymorphic Form-I of the succinate salt of Compound (A).

Since Compound (A) may be administered in combination with other treatments (such as additional chemotherapeutics, radiation or surgery), the doses of each agent or therapy can be lower than the corresponding dose for single-agent therapy.

When Compound (A) is administered in a pharmaceutical composition that comprises one or more agents, and one or more of the agents has a shorter half-life than Compound (A), unit dose forms of the agent(s) and Compound (A) can be adjusted accordingly.

Compound (A) can be administered as one or more unit dosages, e.g., in a capsule or tablet, to achieve the desired dosage. For example, a unit dosage of Compound (A) may be 5 mg, 20 mg, or 40 mg. As an example, for a 160 mg daily dose, a patient may be administered eight 20 mg capsules or four 40 mg capsules. A pharmaceutical composition comprising Compound (A) may be a single unit dosage or multiple unit dosages. For example, a pharmaceutical composition comprising 160 mg of Compound (A) may be a single unit dosage (e.g., capsule) comprising 160 mg of Compound (A) or may be multiple unit dosages (e.g., capsules) that in aggregate comprise 160 mg of Compound (A) (e.g., four 40 mg capsules).

In certain embodiments, Compound (A), its salts including the succinate salt, and the polymorphic forms thereof may be may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intra-hepatic, intralesional and intracranial injection or infusion techniques. In certain embodiments, the compositions are administered orally. In certain embodiments, the compositions are administered intravenously, or subcutaneously.

Therapeutic Methods.

Compound (A), or a pharmaceutically acceptable salt thereof, including the succinate salt, or the polymorphic forms, is capable of inhibiting mutant EGFR and/or HER2 proteins. For example, Compound (A) or a pharmaceutically acceptable salt thereof may inhibit mutant EGFR proteins, e.g., EGFR having one or more mutations in the exon 20 domain. In some embodiments, Compound (A) or a pharmaceutically acceptable salt thereof selectively inhibits mutant EGFR, such as EGFR having one or more exon 20 mutations, over wild-type EGFR.

In some embodiments, Compound (A) or a pharmaceutically acceptable salt thereof selectively inhibits mutant EGFR, such as EGFR having an exon 20 point mutation together with an exon 19 or exon 21 mutation. Compound (A) or a pharmaceutically acceptable salt thereof may therefore be effective in ameliorating diseases and disorders associated with mutant EGFR activity. In another example, Compound (A) or a pharmaceutically acceptable salt thereof may inhibit mutant HER2 proteins, e.g., HER2 having one or more mutations in the exon 20 domain.

In some embodiments, other EGFR inhibitors or a pharmaceutically acceptable salt thereof may selectively inhibit mutant EGFR, such as EGFR having an exon 20 point mutation together with an exon 19 or exon 21 mutation.

In some embodiments, the EGFR inhibitor may be selected from isopropyl 2-((5-acrylamido-4-((2-(dimethylamino)ethyl)(methyl)amino)-2-methoxyphenyl)amino)-4-(1H-indol-3-yl)pyrimidine-5-carboxylate (Compound B) and isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate (Compound C), or a pharmaceutically acceptable salt thereof for treating diseases and disorders associated with mutant EGFR or mutant HER2. Compounds (B) and (C) or pharmaceutically acceptable salts thereof may be produced according to the methods described in WO 2015/195228, which is incorporated herein by reference in its entirety.

In some embodiments, Compound (A) or a pharmaceutically acceptable salt thereof selectively inhibits mutant HER2, such as HER2 having one or more exon 20 mutations, over wild-type EGFR. Compound (A) or a pharmaceutically acceptable salt thereof may therefore be effective in ameliorating diseases and disorders associated with mutant HER2 activity.

Compositions are described herein comprising Compound (A) or a pharmaceutically acceptable salt thereof. In some embodiments, the composition comprises one or more pharmaceutically acceptable excipients.

In some embodiments, the composition comprises Compound (A) or a pharmaceutically acceptable salt thereof filled in a capsule with no excipients.

Some embodiments provide a method for treating a disease or disorder described herein, the method comprising administering a therapeutically effective amount of Compound (A) or a pharmaceutically acceptable salt thereof or pharmaceutical composition comprising Compound (A) or a pharmaceutically acceptable salt thereof to a subject.

Some embodiments provide a method for treating an exon 20 mutant EGFR mediated disorder in a subject, the method comprising administering a therapeutically effective amount of Compound (A) or a pharmaceutically acceptable salt thereof or pharmaceutical composition comprising Compound (A) or a pharmaceutically acceptable salt thereof to a subject.

Some embodiments provide a method for treating an exon 20 mutant HER2 mediated disorder in a subject, the method comprising administering a therapeutically effective amount of Compound (A) or a pharmaceutically acceptable salt thereof or pharmaceutical composition comprising Compound (A) or a pharmaceutically acceptable salt thereof to a subject.

Some embodiments provide a use of Compound (A) or a pharmaceutically acceptable salt thereof or pharmaceutical composition comprising Compound (A) or a pharmaceutically acceptable salt thereof for the treatment of a disease or disorder described herein in a subject.

In some embodiments, the disease or disorder is associate with an exon 20 mutant EGFR.

In some embodiments, the disease or disorder is associate with an exon 20 mutant HER2 disorder in a subject.

Some embodiments provide a use of Compound (A) or a pharmaceutically acceptable salt thereof or pharmaceutical composition comprising Compound (A) or a pharmaceutically acceptable salt thereof in the manufacture of a medicament for the treatment of a disease or disorder described herein in a subject.

In some embodiments, the disease or disorder is cancer, i.e., a cancer is associated with mutant EGFR or mutant HER2. In some embodiments, the cancer is associated with mutant EGFR having one or more mutations in the exon 20 domain. For example, the cancer is associated with mutant EGFR having one or more insertion mutations in the exon 20 domain; or the cancer is associated with mutant EGFR having one or more deletion mutations in the exon 20 domain; or the cancer is associated with mutant EGFR having one or more point mutations. In some embodiments, the cancer is associated with mutant HER2. In some embodiments, the cancer is associated with mutant HER2 having one or more mutations in the exon 20 domain. For example, the cancer is associated with mutant HER2 having one or more deletion mutations in the exon 20 domain; or the cancer is associated with mutant HER2 having one or more point mutations.

In some embodiments, the cancer is selected from non-small cell lung cancer, colorectal cancer, pancreatic cancer, head and neck cancer, breast cancer, ovarian cancer, uterine cancer and stomach cancer. For example, the cancer is non-small cell lung cancer; or the cancer is breast cancer. In certain embodiments, the cancer is non-small cell lung cancer.

In some embodiments, provided herein is a pharmaceutical composition comprising from about 20 mg to about 200 mg (e.g., about 20, 40, 60, 80, 120, 160 or 180 mg) of Compound (A) or a pharmaceutically acceptable salt thereof. In one specific embodiment, the pharmaceutical composition is about 40 mg of Compound (A) or a pharmaceutically acceptable salt thereof.

In some embodiments, the pharmaceutical dosage is administered as one or more capsules or tablets.

A specific embodiment is a pharmaceutical dosage regimen comprising 60 mg, 80 mg, 120 mg, or 160 mg of Compound (A) or a pharmaceutically acceptable salt thereof. In some embodiments, the dosage is about 120 mg. In some embodiments, the dosage is about 160 mg.

In some embodiments, the pharmaceutical dosage regimen is a solid dosage form for oral administration, e.g., a capsule or tablet (including one or more capsules or tablets). In some embodiments, the pharmaceutical dosage is administered once daily; alternatively, the pharmaceutical dosage may be administered twice daily.

In some embodiments, Compound (A) or a pharmaceutically acceptable salt thereof is in a liquid dosage form.

One specific embodiment is a method of treating non-small cell lung cancer associated with mutant EGFR having one or more insertions in the exon 20 domain, the method comprising administering to a patient in need thereof Compound (A) or a pharmaceutically acceptable salt thereof at a dose of 60 mg twice daily.

Another specific embodiment is a method of treating non-small cell lung cancer associated with mutant EGFR having one or more insertions in the exon 20 domain, the method comprising administering to a patient in need thereof Compound (A) or a pharmaceutically acceptable salt thereof at a dose of 80 mg twice daily.

Another specific embodiment is a method of treating non-small cell lung cancer associated with mutant EGFR having one or more insertions in the exon 20 domain, the method comprising administering to a patient in need thereof Compound (A) or a pharmaceutically acceptable salt thereof at a dose of 120 mg once daily.

Another specific embodiment is a method of treating non-small cell lung cancer associated with mutant EGFR having one or more insertions in the exon 20 domain, the method comprising administering to a patient in need thereof Compound (A) or a pharmaceutically acceptable salt thereof at a dose of 160 mg once daily.

In certain embodiments, Compound (A), its salts including the succinate salt, and the polymorphic forms thereof may be used for treating diseases associated with mutant EGFR.

In certain embodiments, the succinate salt of Compound (A) or the polymorphic Form-I of the succinate salt of Compound (A) may be used for treating diseases associated with mutant EGFR.

In certain embodiments, the succinate salt of Compound (A) or the polymorphic Form-I of the succinate salt of Compound (A) may be administered orally.

In certain embodiments, the succinate salt of Compound (A) or the polymorphic Form-I of the succinate salt of Compound (A) may be formulated as a drug-in-capsule with no excipients and administered orally.

In certain embodiments, the succinate salt of Compound (A) may by administered orally at a dose equivalent to 160 mg freebase once daily or at a dose equivalent to 80 mg freebase twice daily, wherein the drug-in-capsule comprises 40 mg of the succinate salt of Compound (A).

In certain embodiments, the polymorphic Form-I of the succinate salt of Compound (A) may by administered orally at a dose equivalent to 160 mg once freebase daily or at a dose equivalent to 80 mg freebase twice daily.

In certain embodiments, the disease associated with mutant EGFR is cancer, including, but not limited to, lung cancer (including NSCLC and SCLC), colorectal cancer, pancreatic cancer, head and neck cancers, breast cancer, ovarian cancer, uterine cancer, gastric cancer, bladder cancer, glioma cancer, or stomach cancer. In certain embodiments, the mutant EGFR cancer is non-small cell lung cancer.

In some embodiments, methods are provided for inhibiting the mutant EGFR activity by contacting a cell, tissue, or organ that expresses the mutant EGFR with Compound (A). In some embodiments, methods are provided for inhibiting the mutant EGFR activity in a subject (including mammals such as humans) by administering into the subject an effective amount of Compound (A) to inhibit or reduce the activity of the mutant EGFR in the subject. In some embodiments, the kinase activity can be inhibited (e.g., reduced) by more than about 25%, about 30%, about 40%, about 50%, about 60%, about 70%, about 80%, or about 90% when contacted with Compound (A) as compared to the kinase activity without such contact. In some embodiments, the kinase can be exon 20 mutant EGFR. For instance, the mutant EGFR can be exon 20 mutant EGFR.

In another embodiment, Compound (A) shows inhibitory activity towards the exon 20 mutant EGFR Val769_Asp770insAlaSerVal and/or the Asp770_Asn771insAsnProGly insertion mutations. In some embodiments, Compound (A) shows inhibitory activity towards one or more of the exon 20 mutant EGFR Asp770_Asn771insSVD, the His773_Val774insNPH, and the Ala763_Tyr764insFQEA insertion mutations. Provided herein, methods of treatment for a mutant EGFR-mediated disorder include subjects who have an exon 20 insertion mutation as listed in Table 1.

TABLE 1

| EGFR amino acid | Insertion Mutation |
|---|---|
| 767 | Ala767_Ser768insThrLeuAla |
| 768 | Ser768_Val769insValAlaSer; Ser768_Val769insAlaTrpThr |
| 769 | Val769_Asp770insAlaSerVal; Val769_Asp770insGlyVal; Val769_Asp770insCysVal; Val769_Asp770insAspAsnVal; Val769_Asp770insGlySerVal; Val769_Asp770insGlyValVal; Val769_Asp770insMetAlaSerValAsp |
| 770 | Asp770_Asn771insSerValAsp; Asp770_Asn771insAsnProGly; Asp770_Asn771insAlaProTrp; Asp770_Asn771insAsp; Asp770_Asn771insAspGly; Asp770_Asn771insGly; Asp770_Asn771insGlyLeu; Asp770_Asn771insAsn; Asp770_Asn771insAsnProHis; Asp770_Asn771insSerValPro; Asp770_Asn771insSerValGln; Asp770_Asn771insMetAlaThrPro; delAsp770insGlyTyr; |
| 771 | Asn771_Pro772insHis; Asn771_Pro772insAsn; delAsn771insGlyTyr; delAsn771insGlyPhe |
| 772 | Pro772_His773insProArg; Pro772_His773insTyrAsnPro; Pro772_His773insX; Pro772_His773insAspProHis; Pro772_His773insAspAsnPro; Pro772_His773insGlnVal; Pro772_His773insThrProHis; Pro772_His773insAsn; Pro772_His773insVal |
| 773 | His773_Val774insAsnProHis; His773_Val774insHis; His773_Val774insProHis; His773_Val774insGlyAsnProHis; His773_Val774insGly; His773_Val774insGlyHis |
| 774 | Val774_Cys775insHisVal |

In other embodiments, the exon 20 insertion mutation can be selected from Val769_Asp770insAlaSerVal and/or the Asp770_Asn771 insAsnProGly. In other embodiments, the exon 20 insertion mutation can be selected from Asp770_Asn771insSVD, His773_Val774insNPH, and Ala763_Tyr764insFQEA.

In some embodiments, methods are disclosed for inhibiting mutant HER2 activity (e.g., selectively modulating) by contacting the HER2 with an effective amount of Compound (A), or a pharmaceutically acceptable form (e.g., pharmaceutically acceptable salts, hydrates, solvates, isomers, prodrugs, and isotopically labeled derivatives) thereof, or a pharmaceutical composition as provided herein, to inhibit the HER2 activity. In some embodiments, the mutant HER2 has one or more exon 20 mutations. In some embodiments, methods are provided for inhibiting kinase activity by contacting the kinase with a solution containing an effective amount of the compound to inhibit the HER2. In some embodiments, methods are provided for inhibiting the HER2 kinase activity by contacting a cell, tissue, or organ that express the kinase with Compound (A). In some embodiments, methods of inhibiting kinase activity in a subject by administering into the subject an effective amount of Compound (A). In some embodiments, the kinase activity can be inhibited (e.g., reduced) by more than about 25%, about 30%, about 40%, about 50%, about 60%, about 70%, about 80%, or about 90% when contacted with Compound (A) as compared to the kinase activity without such contact. In some embodiments, the kinase can be exon 20 mutant HER2. In some embodiments, provided herein are methods of inhibiting mutant HER2 activity in a subject (including mammals such as humans) by contacting said subject with an amount of Compound (A) sufficient to inhibit or reduce the activity of the mutant HER2 in said subject. For instance, the mutant HER2 can be exon 20 mutant HER2.

In some embodiments, the exon 20 mutant HER2 has insertion mutations in its exon 20 domain that have been documented for at least residues 770-831 of HER2. (Arcila et al. Clin Cancer Res 2012; 18:4910-4918; Shigematsu et. al. Cancer Res 2005; 65:1642-46). In one embodiment, Compound (A) shows inhibitory activity towards one or more of the HER2 exon 20 insertion mutants shown in Table 2.

TABLE 2

| HER2 amino acid | Point and Insertion Mutations |
| --- | --- |
| 775 | Ala775_Gly776insTyrValMetAla |
| 776 | Gly776 > ValCys |
| 780 | Pro780_Tyr781insGlySerPro |
| 776 and 777 | Gly776Cys and Val777_Gly778insCysGly |

In another embodiment, Compound (A) shows inhibitory activity towards the Ala775_Gly776insTyrValMetAla exon 20 mutant HER2 insertion mutations. The disclosed methods of treatment for a mutant HER2-mediated disorder are applicable to those subjects, among others, who have exon 20 insertion mutation Ala775_Gly776insTyrValMetAla or another exon 20 insertion mutation listed in Table 2.

In some embodiments, Compound (A) shows inhibitory activity against the wild type receptor tyrosine kinases that include EGFR/ERBB1, HER2/ERBB2/NEU, HER3/ERBB3, and HER4/ERBB4.

In one embodiment, provided herein is a method of treating a mutant EGFR-mediated disorder in a subject, the method comprising administering a therapeutically effective amount of Compound (A) or a pharmaceutical composition as provided herein. In some embodiments, provided herein is a method of ameliorating a mutant EGFR-mediated disorder in a subject, the method comprising administering a therapeutically effective amount of Compound (A) or a pharmaceutical composition as provided herein. In some embodiments, provided herein is a method for inhibiting mutant EGFR, the method comprising contacting a cell expressing mutant EGFR in vitro or in vivo with an effective amount of Compound (A) or composition provided herein. In all these embodiments, the mutant can be, for example, an exon 20 insertion mutant. In some embodiments the mutant can be an exon 20 point mutation, optionally accompanied by another mutation such as exon 19 D and/or exon 21 L.

In some embodiments, provided herein are methods of treating a mutant EGFR-mediated disorder, such as where the mutation is an exon 20 insertion, that is resistant to another anti-cancer agent(s) (e.g., erlotinib, gefitinib, neratinib, afatinib, dacomitinib), the method involving administering a therapeutic effective amount of Compound (A) to a subject in need thereof.

Without being limited by a particular theory, EGFR having one or more exon 20 insertion mutations has been associated with lung cancer (e.g., non-small cell lung cancer NSCLC, SCLC, lung adenocarcinoma), colorectal cancer, pancreatic cancer, and head and neck cancers. Exon 20 insertion mutations are most prevalent in NSCLC: 15% of western Europeans, 30% East Asians, and 50% of non-smokers. (Yasuda 2012). In head and neck cancers, current therapies targeting mutant EGFR include cetuximab, a chimeric mouse-human IgG1antibody. (Chong et al. Nature Med. 2013; 19(11):1389-1400). Exon 20 mutant EGFR colorectal cancer has been treated using cetuximab and panitumumab, a fully humanized IgG2 antibody. Id. Exon 20 mutant EGFR pancreatic cancer has been treated with erlotinib. Id. EGFR having the T790M point mutation, optionally accompanied by exon 19 D and/or exon 21 L mutations, have been associated with NSCLC where the cancer has developed resistance to one or more other TKI's such as erlotinib and gefitinib.

Without being limited by a particular theory, HER2 having one or more exon 20 insertion mutations has been associated with lung cancer (e.g., NSCLC), breast cancer, ovarian cancer, uterine cancer, and stomach cancer. (Santin et al. Int J Gynaecol Obstet 2008; 102:128-31). Current therapies include Herceptin and pertuzamab. HER2 mutations are present in about 2-4% of NSCLC: 80-84% of those patients have the YVMA exon 20 insertion mutation. (Arcila 2012).

In some embodiments, provided herein are methods of using Compound (A), or a pharmaceutically acceptable form (e.g., pharmaceutically acceptable salts, hydrates, solvates, isomers, prodrugs, and isotopically labeled derivatives) thereof, or pharmaceutical compositions as provided herein to treat disease conditions, including, but not limited to, diseases associated with one or more types of mutant EGFR or mutant HER2. In some embodiments, the disclosure relates to a method of treating a hyperproliferative disorder in a subject that comprises administering to said subject a therapeutically effective amount of Compound (A), or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, the disclosure relates to a method of treating cancer in a subject that comprises administering to said subject a therapeutically effective amount of Compound (A), or a pharmaceutically acceptable form (e.g., pharmaceutically acceptable salts, hydrates, solvates, isomers, prodrugs, and isotopically labeled derivatives) thereof, or a pharmaceutical composition as provided herein.

Compound (A) and pharmaceutical compositions are disclosed herein for the manufacture of a medicament for treating a mutant EGFR or mutant HER2 disorder in a subject in need thereof. Also provided are Compound (A) and pharmaceutical compositions for the treatment of a mutant EGFR-mediated disorder or mutant HER2-mediated disorder in a subject in need thereof. In some embodiments, the mutant can be an exon 20 insertion mutation. In some embodiments, the mutant can be an exon 20 point mutation, optionally accompanied by another mutation such as exon 19 D and/or exon 21 L.

Patients that may be treated with Compound (A), or a pharmaceutically acceptable form (e.g., pharmaceutically acceptable salts, hydrates, solvates, isomers, prodrugs, and isotopically labeled derivatives) thereof, or pharmaceutical compositions as provided herein, according to the methods as provided herein include, but are not limited to, patients that have been diagnosed as having lung cancer (NSCLC and SCLC), colorectal cancer, pancreatic cancer and head and neck cancers. In other embodiments, a patient may be diagnosed with lung cancer, breast cancer, ovarian cancer, uterine cancer, and stomach cancer. In other embodiments, a patient may be diagnosed with gastric, bladder, glioma, and stomach cancer.

In some embodiments, patients treated with Compound (A) are (1) NSCLC patients with EGFR exon 20 activating insertions and no active, measurable CNS metastases, excluding patients who previously responded to an EGFR TKI; (2) NSCLC patients with HER2 exon 20 activating insertions or point mutations and no active, measurable CNS metastases; (3) NSCLC patients with EGFR exon 20 activating insertions or HER2 exon 20 activating insertions or point mutations and active, measurable CNS metastases; (4) NSCLC patients with other targets against which Compound (A) is active (examples include EGFR exon 19 deletions or exon 21 substitutions [with or without T790M mutations] and other uncommon EGFR activating mutations), with or without active, measurable CNS metastases; (5) Patients with solid tumors other than NSCLC with targets against which Compound (A) is active (examples include EGFR/HER2 activating mutations), with or without active, measurable CNS metastases; and/or (6) NSCLC patients with EGFR exon 20 activating insertions, with or without active, measurable CNS metastases, including patients who previously responded to an EGFR TKI. In some embodiments, patients treated with Compound (A) are NSCLC patients with EGFR exon 20 activating insertions.

In some embodiments, a symptom associated with a disease or disorder provided herein can be reduced by at least about 10%, at least about 20%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease can be statistically significant, for example, as assessed using an appropriate parametric or non-parametric statistical comparison.

In some embodiments, treatment of a mutant EGFR-mediated disorder or a mutant HER2-mediated disorder involves administering (as a monotherapy or in combination with one or more other anti-cancer agents, one or more agents for ameliorating side effects, radiation, etc) a therapeutically effective amount of Compound (A) to a human or animal in need of it in order to inhibit, slow or reverse the growth, development or spread of cancer, including solid tumors or other forms of cancer such as leukemias, in the subject. Such administration constitutes a method for the treatment or prophylaxis of diseases mediated by one or more kinases inhibited by Compound (A) or a pharmaceutically acceptable form thereof. In one embodiment, the mutant can be an exon 20 insertion mutation.

Combination Treatments

In some embodiments, provided herein are methods for combination therapies in which an agent known to modulate other pathways, or other components of the same pathway, or even overlapping sets of target enzymes are used in combination with Compound (A), or a pharmaceutically acceptable form (e.g., pharmaceutically acceptable salts, hydrates, solvates, isomers, prodrugs, and isotopically labeled derivatives) thereof. In one embodiment, such therapy includes, but is not limited to, the combination of Compound (A) with chemotherapeutic agents, therapeutic antibodies, and radiation treatment, to provide a synergistic or additive therapeutic effect.

When administered as a combination, the therapeutic agents can be formulated as separate compositions that are administered at the same time or sequentially at different times, or the therapeutic agents can be given as a single composition. The phrase "combination therapy", in referring to the use of Compound (A) together with another pharmaceutical agent, means the co-administration of each agent in a substantially simultaneous manner as well as the administration of each agent in a sequential manner, in either case, in a regimen that will provide beneficial effects of the drug combination. Co-administration includes, inter alia, the simultaneous delivery, e.g., in a single tablet, capsule, injection or other dosage form having a fixed ratio of these active agents, as well as the simultaneous delivery in multiple, separate dosage forms for each agent respectively. Thus, the administration of Compound (A) can be in conjunction with additional therapies known to those skilled in the art in the prevention or treatment of cancer, such as radiation therapy or cytostatic agents, cytotoxic agents, other anti-cancer agents and other drugs to ameliorate symptoms of the cancer or side effects of any of the drugs.

If formulated as a fixed dose, such combination products employ Compound (A) within suitable dosage ranges. Compound (A) can also be administered sequentially with other anticancer or cytotoxic agents when a combination formulation is inappropriate. As defined herein, combination therapy is not limited in the sequence of administration; Compound (A) can be administered prior to, simultaneously with, or after administration of the other anticancer or cytotoxic agent.

In some embodiments, pharmaceutical compositions disclosed herein can include Compound (A) or a pharmaceutically acceptable salt thereof; an additional agent selected from a kinase inhibitory agent (small molecule, polypeptide, antibody, etc.), an immunosuppressant, an anticancer agent, an anti-viral agent, anti-inflammatory agent, antifungal agent, antibiotic, or an anti-vascular hyperproliferation compound; and any pharmaceutically acceptable carrier, adjuvant or vehicle.

Alternate pharmaceutical compositions disclosed herein include Compound (A) or a pharmaceutically acceptable salt thereof; and a pharmaceutically acceptable carrier, adjuvant or vehicle. Such compositions can optionally comprise one or more additional therapeutic agents, including, for example, kinase inhibitory agents (small molecule, polypeptide, antibody, etc.), immunosuppressants, anti-cancer agents, anti-viral agents, anti-inflammatory agents, antifungal agents, antibiotics, or anti-vascular hyperproliferation compounds.

In one embodiment, Compound (A) or a pharmaceutically acceptable form (e.g., pharmaceutically acceptable salts, hydrates, solvates, isomers, prodrugs, and isotopically labeled derivatives) thereof, or pharmaceutical compositions as provided herein, can present synergistic or additive efficacy when administered in combination with agents that inhibit other kinase(s) production or activity. Such combination can reduce undesired side effect of the compounds and compositions described herein, if such effect occurs.

In some embodiments, treatment can be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF)), hyperthermia, cryotherapy, agents to attenuate any adverse effects (e.g., antiemetics), and other cancer chemotherapeutic drugs. The other agent(s) can be administered using a formulation, route of administration and dosing schedule the same or different from that used with Compound (A).

For treatment of mutant EGFR-mediated diseases and mutant HER2-mediated diseases Compound (A), or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with commonly prescribed drugs including, but not limited to, anti-cancer drugs (e.g., anti-proliferative agents, anti-angiogenic agents and other chemotherapeutic agents).

Compound (A), or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with an amount of one or more substances selected from anti-angiogenesis agents, signal transduction inhibitors, and anti-proliferative agents, glycolysis inhibitors, or autophagy inhibitors.

Compound (A) can be used in combination with the agents provided herein or other suitable agents, depending on the condition being treated. Hence, in some embodiments, Compound (A) will be co-administered with other agents as described above. When used in combination therapy, Compound (A) can be administered with the second agent simultaneously or separately. This administration in combination can include simultaneous administration of the two agents in the same dosage form, simultaneous administration in separate dosage forms, and separate administration. That is, Compound (A) and any of the agents described above can be formulated together in the same dosage form and administered simultaneously. Alternatively, Compound (A) and any of the agents described above can be simultaneously administered, wherein both the agents are present in separate formulations. In another alternative, Compound (A) can be administered just followed by and any of the agents described above, or vice versa. In the separate administration protocol, Compound (A) and any of the agents described above can be administered a few minutes apart, or a few hours apart, or a few days apart.

Administration of Compound (A) can be effected by any method that enables delivery of Compound (A) to the site of action. An effective amount of Compound (A) can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When Compound (A) is administered in a pharmaceutical composition that comprises one or more agents, and the agent has a shorter half-life than Compound (A), unit dose forms of the agent and Compound (A) can be adjusted accordingly.

EXAMPLES

The following abbreviations have the definitions set forth below:

| | | | |
|---|---|---|---|
| $AlCl_3$: | aluminum chloride | IPOAc: | isopropyl acetate |
| 2-BuOH: | 2-butanol (sec-butyl alcohol) | IT: | internal temperature |
| | | KOTMS: | potassium trimethylsilanolate |
| DCE: | 1,2-dichloroethane | | |
| DCM: | dichloromethane | MeCN: | acetonitrile |
| DIEA: | diisopropylethylamine | MeOH: | methanol |
| DMF: | N,N-dimethylformamide | MeTHF: | methyltetrahydrofuran |
| DMSO: | dimethylsulfoxide | 2-MeTHF: | 2-methyltetrahydrofuran |
| EtOAc: | ethyl acetate | NMR: | nuclear magnetic resonance |
| EtOH: | ethanol | | |
| h: | hour(s) | PTSA: | p-toluenesulfonic acid monohydrate |
| IPA: | iso-propanol | | |
| i-Pr or iPr: | isopropyl | RT: | room temperature |
| THF: | tetrahydrofuran | T3P: | propylphosphonic anhydride |

$^1$H Nuclear Magnetic Resonance Spectroscopy ($^1$H NMR)

$^1$H NMR experiments were performed on a Bruker AVA500 or PRO500 spectrometer ($^1$H frequency: 500 MHz). Samples were prepared in $CDCl_3$ or $d_6$-DMSO from glass ampoules. Each sample was prepared to ca. 10 mM concentration.

X-Ray Powder Diffraction (XRPD)

Samples were scanned between 3 and 35° 2θ. Material was gently compressed into a well mounted on Kapton film. The sample was then loaded into a PANalytical X'Pert Pro diffractometer running in transmission mode and analyzed using the following experimental conditions:

| Raw Data Origin | XRD measurement |
|---|---|
| Start Position [°2Th.] | 3.0066 |
| End Position [°2Th.] | 34.9866 |
| Step Size [°2Th.] | 0.0130 |
| Scan Step Time [s] | 67.9377 |
| Scan Type | Continuous |
| PSD Mode | Scanning |
| PSD Length [°2θ] | 3.35 |
| Offset [°2θ] | 0.0000 |
| Divergence Slit Type | Fixed |
| Divergence Slit Size [°] | 1.0000 |
| Specimen Length [mm] | 10.00 |
| Measurement Temperature [° C.] | 25.00 |
| Anode Material | Cu |
| K-Alpha1 [Å] | 1.54060 |
| K-Alpha2 [Å] | 1.54443 |
| K-A2/K-A1 Ratio | 0.50000 |
| Generator Settings | 40 mA, 40 kV |
| Goniometer Radius [mm]: | 240.00 |
| Dist. Focus-Diverg. Slit [mm] | 91.00 |
| Incident Beam Monochromator | No |
| Spinning | No |

Thermogravimetric/Differential Thermal Analysis (TG/DTA)

Approximately 5 mg of material was weighed into an open aluminum pan and loaded into a simultaneous thermogravimetric/differential thermal analyzer (TG/DTA) and equilibrated at room temperature. The sample was then heated at a rate of 10° C./min from 25° C. to 300° C. during which time the change in sample weight was recorded along with any differential thermal events (DTA). Nitrogen was used as the purge gas at a flow rate of 300 cm$^3$/min.

In cases with labile solvates, wet material was added to an aluminum pan and allowed to dry under a flow of nitrogen at 300 cm$^3$/min until a constant weight was observed.

Differential Scanning Calorimetry (DSC)

Approximately 5 mg of material was weighed into an aluminum DSC pan and sealed non-hermetically with a pierced aluminum lid. The sample pan was then loaded into a Seiko DSC6200 (equipped with a cooler). The sample and reference were heated to up to 220° C. (unless specified) at a heating rate of 10° C./min and the resulting heat flow response monitored. The sample was subsequently cooled to 20° C. at a cooling rate of 10° C./min and any thermal events recorded. A second heating run was then conducted using the same parameters as the first heating run.

In cases with labile solvates, wet material was added to an aluminum DSC pan and dried under a flow of nitrogen until the material appeared visibly dry.

Example 1 Procedure for the Preparation of isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate (Compound (A))

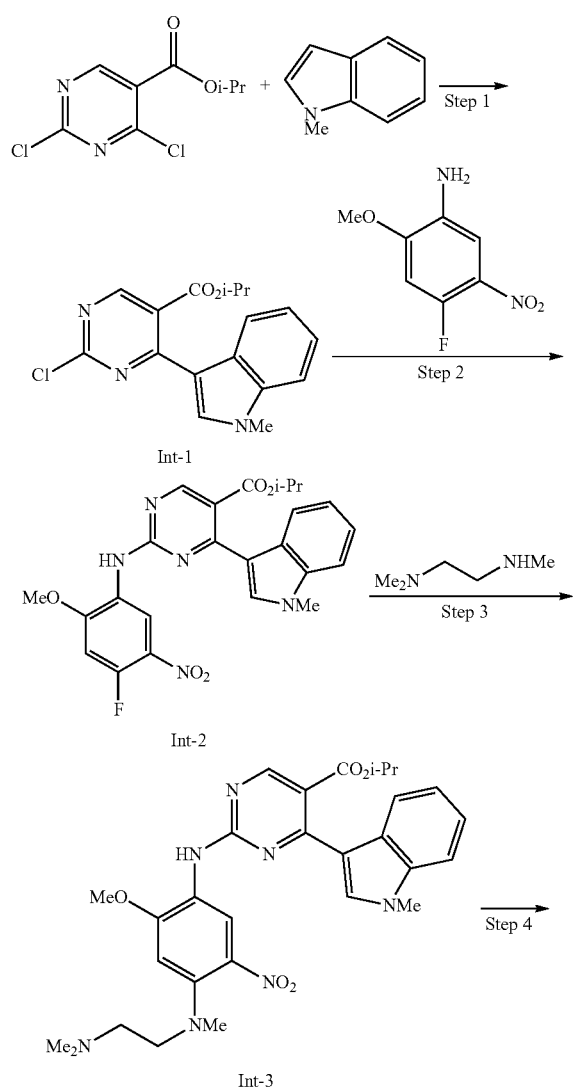

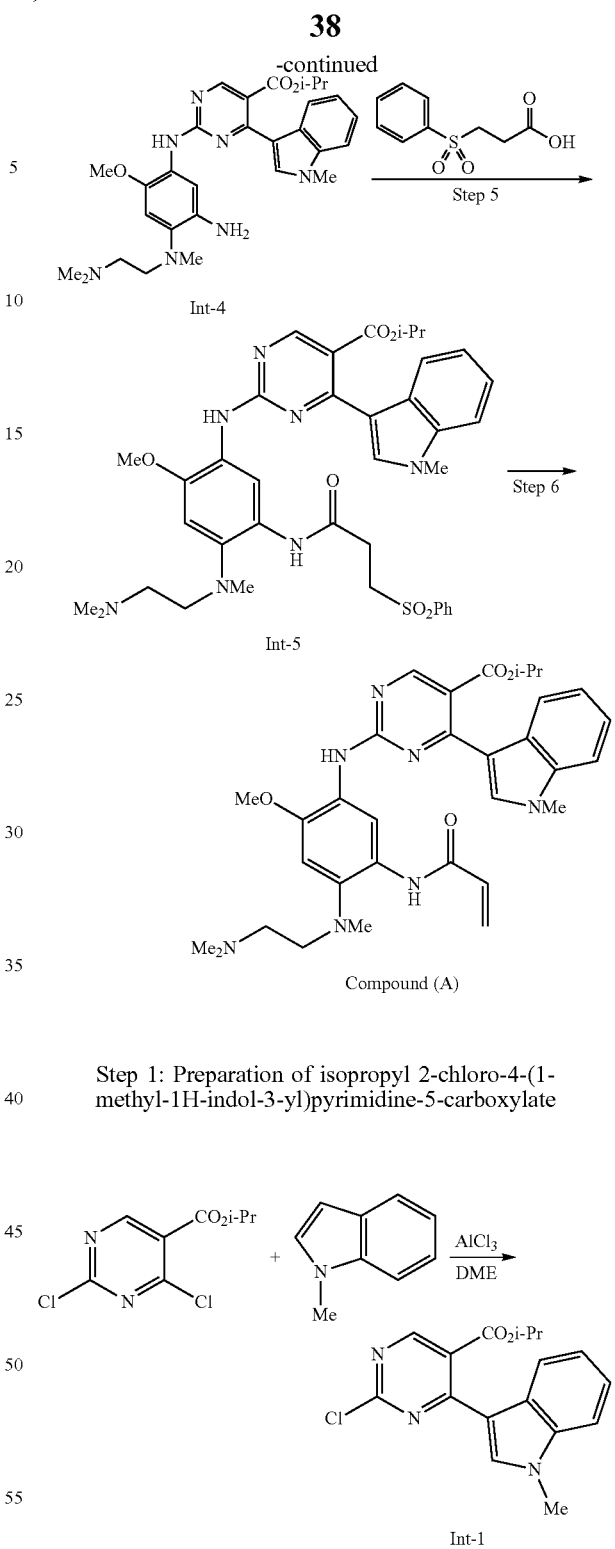

Step 1: Preparation of isopropyl 2-chloro-4-(1-methyl-1H-indol-3-yl)pyrimidine-5-carboxylate To a 2 L Radley reactor equipped with a mechanical stirrer, a thermometer, and a refluxing condenser was charged isopropyl 2,4-dichloropyrimidine-5-carboxylate (100 g, 42.5 mmol, 1.00 eq.) and 1,2-dimethoxyethane (DME, 1.2 L, 12 vol) at RT. The mixture was cooled to 3° C., and granular $AlCl_3$ (65.5 g, 49:1 mmol, 1.15 eq.) was added in 2 portions (IT 3-12° C., jacket set 0° C.). The white slurry was stirred 15-25° C. for 60 minutes. 1-Methylindole (59 g, 44.9 mmol, 1.06 eq.) was added in one portion (IT20-21° C.). DME (100 mL) was used to aid 1-Methylindole transfer. The reaction mixture was aged for at 35° C. for 24 h. Samples (1 mL) were removed at 5 h and 24 h for HPLC analysis (TM1195).

At 5 h the reaction had 70% conversion, while after 24 h the desired conversion was attained (≤98%).

The reaction mixture was cooled to 0° C. to 5° C. and stirred for 1 h. The solids were collected via filtration and washed with DME (100 mL). The solids (AlCl$^3$ complex) were charged back to reactor followed by 2-MeTHF (1 L, 10 vol), and water (400 mL, 4 vol). The mixture was stirred for 10 minutes. The stirring was stopped to allow the layers to separate. The organic phase was washed with water (200 mL, 2 vol). The combined aqueous phase was re-extracted with 2-MeTHF (100 mL, 1 vol).

During workup a small amount of product title compound started to crystallize. Temperature during workup should be at about 25-40° C.

The combined organic phase was concentrated under mild vacuum to 300-350 mL (IT 40-61° C.). Heptane (550 mL) was charged while maintaining the internal temperature between 50° C. and 60° C. The resulting slurry was cooled at 25° C. over 15 minutes, aged for 1 h (19-25° C.) and the resulting solids isolated by filtration.

The product was dried at 50° C. under vacuum for 3 days to yield 108.1 g (77% yield) of the title compound, in 100% purity (AUC) as a yellow solid.

$^1$H NMR (400 MHZ, DMSO-d$_6$) δ ppm 1.24 (d, J=6.53 Hz, 6H) 3.92 (s, 3H) 5.19 (spt, J=6.27 Hz, 1H) 7.25-7.35 (m, 2H) 7.59 (d, J=8.03 Hz, 1H) 8.07 (s, 1H) 8.16 (d, J=7.53 Hz, 1H) 8.82 (s, 1H).

Step 2: Preparation of isopropyl 2-((4-fluoro-2-methoxy-5-nitrophenyl)amino)-4-(1-methyl-1H-indol-3-yl)pyrimidine-5-carboxylate

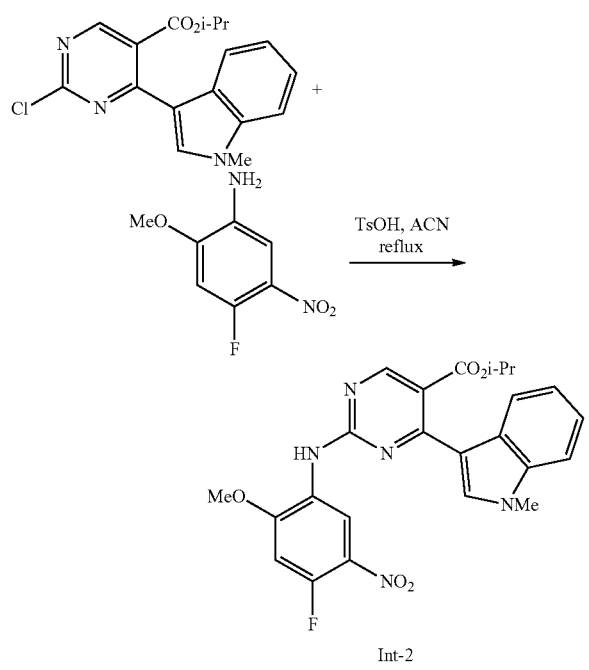

A mixture of the product of step 1 (85.0 g, 258 mmol, 1.0 eq.), 4-fluoro-2-methoxy-5nitroaniline (57.0 g, 306 mmol, 1.2 eq.) and PTSA monohydrate (13.3 g, 70.0 mmol, 0.27 eq.) in acetonitrile (1.4 L, 16.5 v) was heated to 76-81° C. under nitrogen in a 2 L Radley reactor. IPC at 19 h indicated that the reaction was complete.

The reaction mixture was cooled to 25° C. and water (80 mL) was charged in one portion (IT during charge dropped from 25° C. to 19° C.). The reaction mixture was aged for 1 h at 21° C. and then the resulting solids were isolated by filtration. The product was washed with EtOAc (2×150 mL) and dried in high vacuum at 50° C. to 60° C. for 44 h to give 121.5 g of the title compound (98% yield), HPLC purity 100% a/a; NMR indicated that PTSA was purged.

$^1$H NMR (400 MHz, DMSO-d$_6$) δ ppm 1.21 (d, J=6.02 Hz, 6H) 3.91 (s, 3H) 4.02 (s, 3H) 5.09 (spt, J=6.27 Hz, 1H) 7.10 (t, J=7.53 Hz, 1H) 7.26 (t, J=7.58 Hz, 1H) 7.42 (d, J=13.05 Hz, 1H) 7.55 (d, J=8.53 Hz, 1H) 7.90 (br d, J=7.53 Hz, 1H) 7.98 (s, 1H) 8.75 (s, 1H) 8.88 (d, J=8.03 Hz, 1H) 9.03 (s, 1H).

Step 3: Preparation of isopropyl 2-((4-((2-(dimethylamino)ethyl(methyl)amino)-2-methoxy-5-nitrophenyl)amino)-4-(1-methyl-1H-indol-3-yl)pyrimidine-5-carboxylate

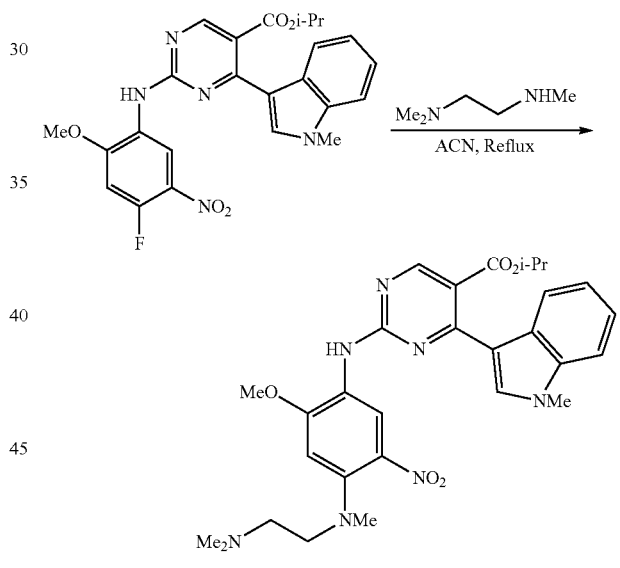

A 50 L flask was charged 1.500 kg of the product of step 2 (3.1 moles, 1.0 equiv.), 639.0 g N,N,N-trimethylethylenediamine (6.3 mol, 2 equiv.), and 21 L MeCN. The resulting slurry was mixed for 7 hours at reflux. The reaction was cooled overnight. Water (16.5 L) was added before the solids were isolated. After isolation of the solids, a wash of 2.25 L MeCN in 2.25 L water was conducted to provide the title compound. The solids were dried, under vacuum, at 75° C. HPLC purity a/a % of the dry solid was 99.3%.

$^1$H NMR (400 MHZ, DMSO-d$_6$) δ ppm 1.22 (d, J=6.02 Hz, 6H) 2.09-2.13 (m, 1H) 2.19 (s, 6H) 2.49-2.52 (m, 1H) 2.89 (s, 3H) 3.29-3.35 (m, 2H) 3.89 (s, 3H) 3.94 (s, 3H) 5.10 (spt, J=6.19 Hz, 1H) 6.86 (s, 1H) 7.07 (br t, J=7.53 Hz, 1H) 7.24 (t, J=7.28 Hz, 1H) 7.53 (d, J=8.53 Hz, 1H) 7.86-8.02 (m, 2H) 8.36 (s, 1H) 8.69 (s, 1H) 8.85 (s, 1H).

Step 4: Preparation of isopropyl 2-((5-amino-4-((2-(dimethylamino)ethyl)(methyl)-amino)-2-methoxy-phenyl)amino)-4-(1-methyl-1H-indol-3-yl)pyrimidine-5-carboxylate

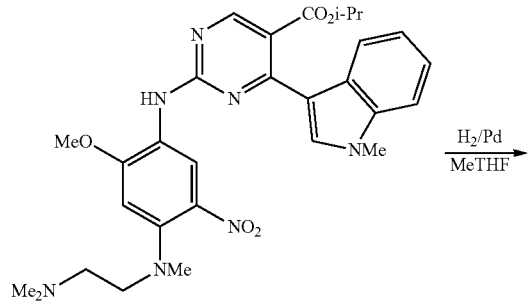

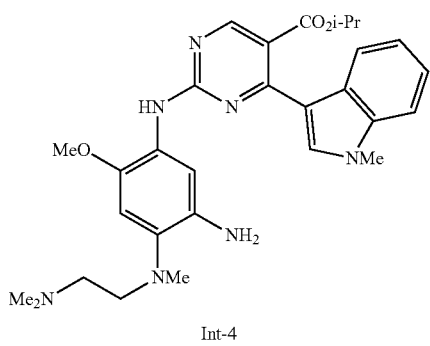

Int-4

To a mixture of the product of step 3 (1.501 kg, 2.67 mol, 1.00 eq.) and 10% Pd/C (64% wet, 125.0 g, 0.011 eq.) was added 2-MeTHF (17.7 L) in a 20 L pressure reactor. The mixture was hydrogenated at 6-10 psi H$_2$ and at 40° C. until IPC indicated complete conversion (11 h, the reaction product 99.0%). The reaction mixture was filtered (Celite), and the pad rinsed with MeTHF (2.5 L total). The filtrate was stored under N$_2$ in a refrigerator until crystallization.

Approximately 74% of 2-MeTHF was evaporated under reduced pressure while maintaining IT 23-34° C. residual volume in the reactor was approximately 4.8 L). To the mixture was added n-heptane (6 L) over 15 min via dropping funnel. The resulting slurry was aged at room temperature overnight. The next day the solids on the walls were scraped to incorporate them into the slurry and the solids were isolated by filtration. The isolated solids were washed with n-heptane containing 5% MeTHF (2×750 mL), and dried (75° C., 30 inch Hg) to yield 1287 g (91% yield) of the title compound as a yellow solid. HPLC purity: 99.7% pure.

$^1$H NMR (400 MHZ, DMSO-d$_6$) δ ppm 1.20 (d, J=6.02 Hz, 6H) 2.21 (s, 6H) 2.37-2.44 (m, 2H) 2.68 (s, 3H) 2.93 (t, J=6.78 Hz, 2H) 3.74 (s, 3H) 3.90 (s, 3H) 4.60 (s, 2H) 5.08 (spt, J=6.19 Hz, 1H) 6.80 (s, 1H) 7.08-7.15 (m, 1H) 7.19-7.26 (m, 2H) 7.52 (d, J=8.03 Hz, 1H) 7.94-8.01 (m, 2H) 8.56 (s, 1H) 8.66 (s, 1H).

Step 5: Preparation of isopropyl 2-((4-((2-(dimethylamino)ethyl)(methyl)amino)-2-methoxy-5-(3-(phenylsulfonyl)propanamido)phenyl)amino)-4-(1-methyl-1H-indol-3-yl)pyrimidine-5-carboxylate

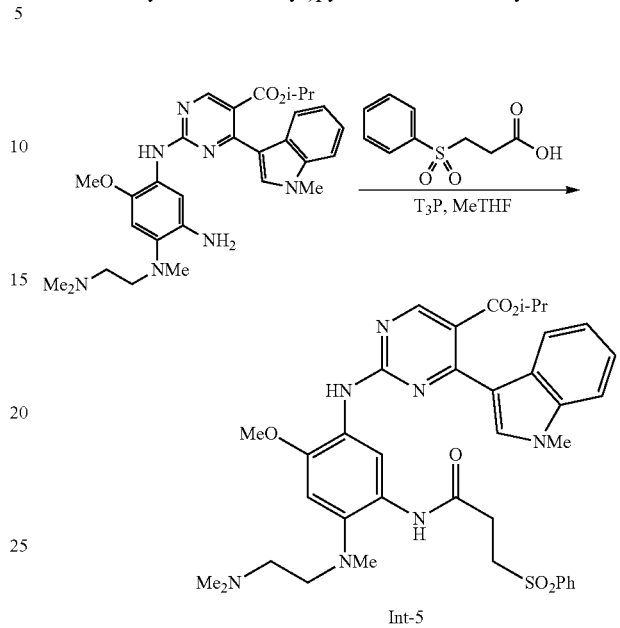

Int-5

A mixture of the product of step 4 (1.284 kg, 2.415 mol, 1.0 eq.) and 3-(phenylsulfonyl)propionic acid (0.5528 kg, 2.580 mol, 1.07 eq.) in anhydrous DCM (8.5 L) was cooled to 2° C., and treated with DIEA (0.310 kg, 2.399 mol, 1.0 eq.). To the reaction mixture was charged over 40 min, 50% w/w T$_3$P in MeTHF (1.756 kg, 2.759 mol, 1.14 eq.) while maintaining the internal temperature between 0° C. and 8° C. The mixture was stirred at 0° C. to 5° C. for 15 minutes and then warmed over 30 min to 15° C. then held at 15° C. to 30° C. for 60 min.

The reaction was quenched with water (179 mL). The reaction mixture was stirred at ambient temperature for 30 min then DIEA (439 g) was charged in one portion. The resulting mixture was aged for 15 min, and then treated with 5% aqueous K$_2$CO$_3$ (7.3 L) at 22-25° C. The organic layer was separated and the aqueous layer back extracted with DCM (6.142 L). The combined organic extract was washed with brine (2×5.5 L).

The organic extract was concentrated to 6.5 L, diluted with EtOH, 200 Proof (14.3 kg), and the mixture concentrated under vacuum (23-25 inch Hg/IT40-60° C.) to a residual volume of 12.8 L.

The residual slurry was treated with EtOH, 200 Proof (28.8 Kg), and heated to 69° C. to obtain a thin slurry. The reaction mixture was cooled to 15° C. over 2 h, and stored overnight at 15° C. under nitrogen.

The next day, the mixture was cooled to 5° C., and aged for 30 minutes. The resulting solid was isolated by filtration, washed with EtOH (2×2.16 kg) and dried to give 1.769 kg (100% yield) of the title compound. HPLC purity 99.85%.

$^1$H NMR (400 MHZ, DMSO-d$_6$) δ ppm 1.08-1.19 (m, 8H) 2.15 (s, 6H) 2.32 (t, J=5.77 Hz, 2H) 2.66-2.76 (m, 5H) 2.88 (br t, J=5.52 Hz, 2H) 3.48 (qd, J=7.03, 5.02 Hz, 1H) 3.60-3.69 (m, 2H) 3.83 (s, 3H) 3.89 (s, 3H) 4.40 (t, J=5.02 Hz, 1H) 5.04 (quin, J=6.27 Hz, 1H) 7.01-7.09 (m, 2H) 7.22

(t, J=7.53 Hz, 1H) 7.52 (d, J=8.53 Hz, 1H) 7.67-7.82 (m, 4H) 7.97 (s, 1H) 7.98-8.00 (m, 1H) 8.14 (s, 1H) 8.61-8.70 (m, 3H) 10.09 (s, 1H).

Step 6: Preparation of isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (Compound (A))

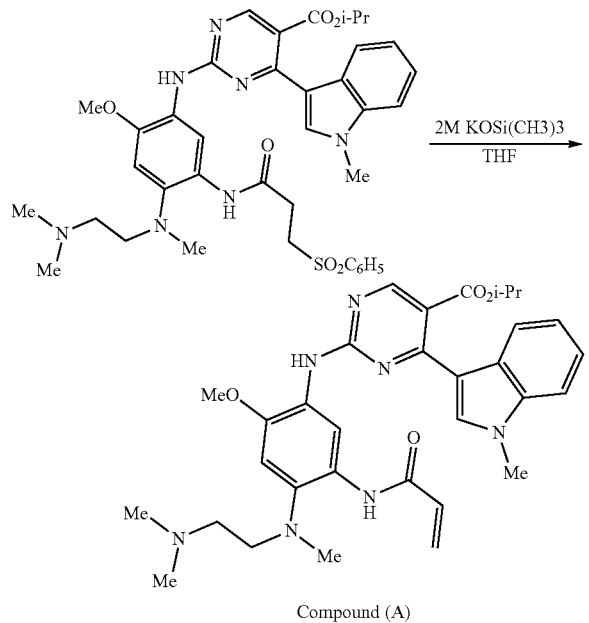

Compound (A)

The product of step 5 (1.600 kg, 2.198 mol, 1.0 equiv.) was dissolved in anhydrous THF (19.5 kg) and was treated at −1° C. to 1° C. with 2M KOSi(CH$_3$)$_3$ in THF (2.72 L, 5.44 mol, 2.47 equiv.). KOSi(CH$_3$)$_3$ was added over 5 minutes, reactor jacket set at −5° C. to 10° C. 2 M KOSi(CH$_3$)$_3$ solution was prepared by dissolving 871 g of KOSi(CH$_3$)$_3$ technical grade (90%) in 3.056 L of anhydrous THF.

The reaction mixture was aged for 60 minutes. Potable water (22 L) was charged to the reaction mixture over 110 minutes, while maintaining temperature at 2-7° C. The resulting suspension was aged at 3-7° C. for 60 minutes; the product was isolated by filtration (the filtration rate during crude product isolation was (1.25 L/min), washed with potable water (2×1.6 L) and air dried overnight and then in high vacuum for 12 h at 45° C. to give 1.186 kg of crude title compound (92% yield).

$^1$H NMR (500 MHZ, DMSO-d$_6$) δ ppm 1.05 (t, J=7.09 Hz, 2H) 1.11 (d, J=6.36 Hz, 6H) 2.11 (s, 6H) 2.28 (br t, J=5.38 Hz, 3H) 2.55-2.67 (m, 3H) 2.69 (s, 3H) 2.83 (br t, J=5.38 Hz, 3H) 3.31 (s, 3H) 3.36-3.51 (m, 2H) 3.54-3.70 (m, 3H) 3.75-3.82 (m, 3H) 4.33 (t, J=5.14 Hz, 1H) 4.99 (dt, J=12.35, 6.30 Hz, 2H) 5.75 (s, 1H) 6.95-7.07 (m, 2H) 7.17 (br t, J=7.58 Hz, 2H) 7.48 (d, J=8.31 Hz, 2H) 7.62-7.71 (m, 3H) 7.71-7.83 (m, 2H) 7.93 (d, J=7.83 Hz, 3H) 8.09 (s, 2H) 8.53-8.67 (m, 3H) 10.03 (s, 2H).

Step 7: Preparation of Polymorphic Form-I of isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (Free Base Compound (A))

Method 1: The crude product of step 6 (1.130 kg) was recrystallized by dissolving it in EtOAc (30.1 kg) at 75° C., polish filtered (1.2 μm in-line filter), followed by concentration of the filtrate to 14 L of residue (IT during concentration is 58-70° C.). The residual slurry was cooled to 0° C. over 70 minutes and then aged at 0-2° C. for 30 minutes. Upon isolation the product was dried to a constant weight to give 1.007 kg (89% recovery) of the title compound as polymorphic Form-I. Purity (HPLC, a/a %, 99.80%).

Alternatively, polymorphic Form-I of free base Compound (A) is prepared or purified with the following steps.

Free base Compound (A) was slurried in DCM. The suspension was filtered and 32 g of solid free base was isolated. The mother liquor was concentrated to give a suspension which was filtered to give a second batch of free base Compound (A) (25 g). The mother liquor was then purified by column chromatography using 5% methanol in DCM. Pure column fractions of free base Compound (A) were combined and concentrated to give a third batch of free base Compound (A) (28 g).

The three batches of free base Compound (A) were combined and dissolved in DCM. The mixture was filtered and evaporated to dryness to give polymorphic Form-I of free base Compound (A) as a light yellow solid (82 g).

$^1$H NMR (500 MHZ, CHLOROFORM-d) δ ppm 1.05 (br d, J=5.75 Hz, 6H) 1.28 (s, 1H) 2.20 (s, 1H) 2.28 (s, 8H) 2.73 (s, 3H) 2.90 (br s, 2H) 3.90 (s, 3H) 3.97 (s, 3H) 5.02 (dt, J=12.45, 6.23 Hz, 1H) 5.71-5.76 (m, 1H) 6.36 (br dd, J=16.63, 10.09 Hz, 1H) 6.50 (dd, J=16.95, 1.81 Hz, 1H) 6.82 (s, 1H) 7.13-7.18 (m, 1H) 7.23 (t, J=7.62 Hz, 1H) 7.29 (s, 1H) 7.35 (d, J=8.20 Hz, 1H) 7.59 (br s, 1H) 7.92 (s, 1H) 8.91 (s, 1H) 9.81 (s, 1H) 10.17 (br s, 1H)

The XRPD data for polymorphic Form-I of the free base Compound (A) is shown in FIG. 1 and in Table 3 below.

TABLE 3

| Peak No. | Position [°2θ] | d-spacing [Å] | Rel. Intensity [%] |
|---|---|---|---|
| 1 | 6.1 | 14.6 | 100.0 |
| 2 | 8.7 | 10.2 | 43.2 |
| 3 | 9.5 | 9.3 | 28.5 |
| 4 | 10.1 | 8.7 | 25.8 |
| 5 | 11.0 | 8.0 | 14.0 |
| 6 | 11.3 | 7.8 | 9.2 |
| 7 | 11.6 | 7.6 | 34.2 |
| 8 | 12.2 | 7.3 | 40.0 |
| 9 | 12.6 | 7.0 | 34.7 |
| 10 | 14.5 | 6.1 | 6.5 |
| 11 | 15.0 | 5.9 | 6.4 |
| 12 | 15.4 | 5.8 | 47.1 |
| 13 | 15.6 | 5.7 | 38.4 |
| 14 | 16.0 | 5.5 | 50.0 |
| 15 | 16.3 | 5.4 | 28.2 |
| 16 | 16.7 | 5.3 | 6.3 |
| 17 | 18.3 | 4.8 | 12.6 |
| 18 | 18.7 | 4.7 | 21.2 |
| 19 | 20.1 | 4.4 | 13.4 |
| 20 | 20.5 | 4.3 | 20.2 |
| 21 | 22.1 | 4.0 | 54.1 |
| 22 | 22.8 | 3.9 | 9.5 |
| 23 | 24.5 | 3.6 | 6.4 |
| 24 | 25.3 | 3.5 | 32.6 |
| 25 | 25.7 | 3.5 | 15.5 |
| 26 | 28.0 | 3.2 | 5.2 |
| 27 | 29.7 | 3.0 | 5.1 |

Figure 2:
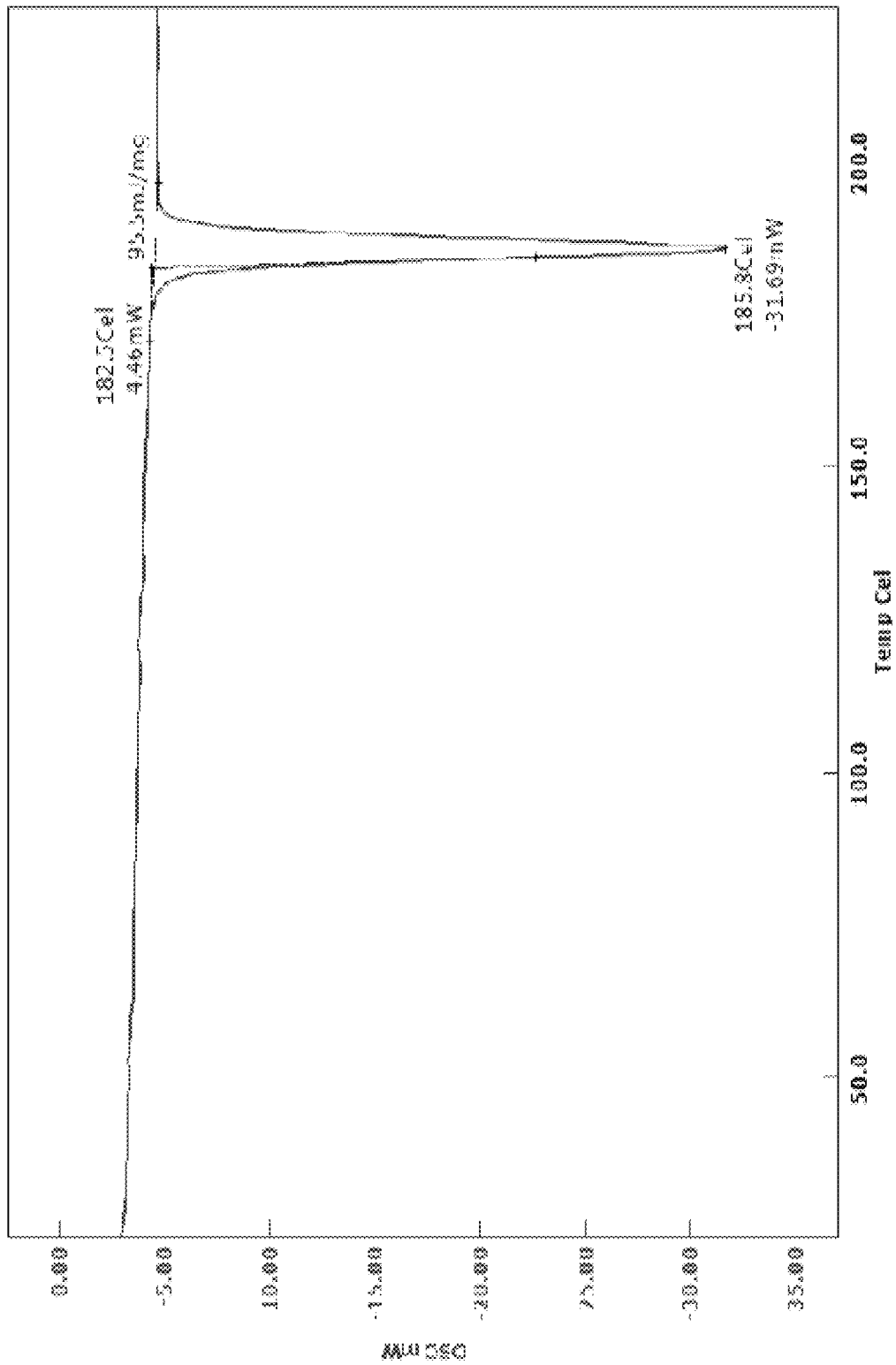
FIG. 2 is a DSC profile for the polymorphic Form-I of the anhydrous free base of Compound (A).

DSC data for polymorphic Form-I of the free base Compound (A) is shown in FIG. 2. The profile displays an endothermic transition with an onset temperature of about 182.5° C. with a melt of 185.8° C., an associated enthalpy of 95.5 mJ/mg. The DSC experiment was conducted up to 240° C.

Figure 3:
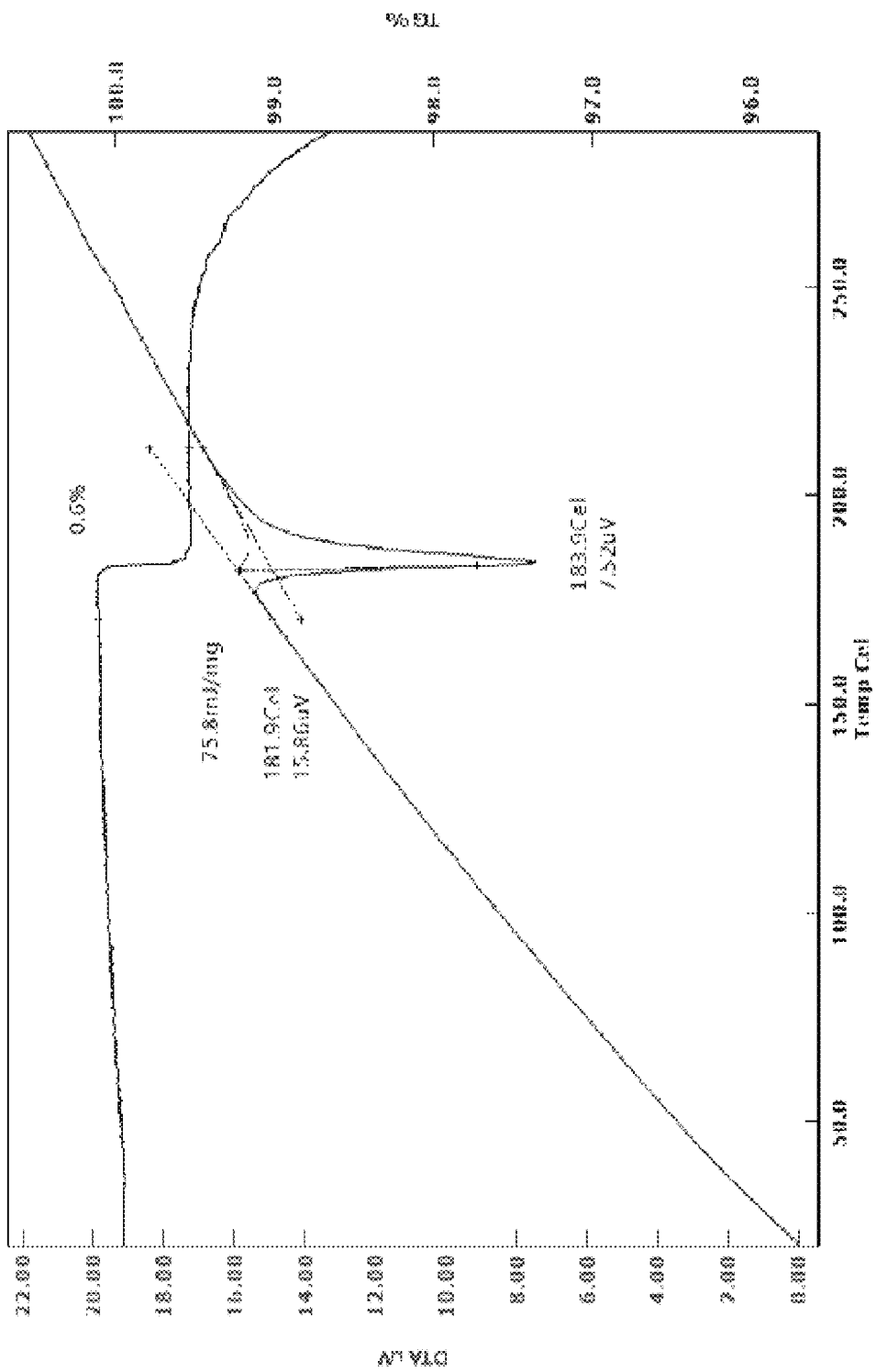
FIG. 3 is a TG/DTA profile for the polymorphic Form-I of the anhydrous free base of Compound (A).

TG/DAT data for polymorphic Form-I of the free base Compound (A) is shown in FIG. 3. The profile displays an endothermic transition with an onset temperature of about 181.9° C., which is accompanied by a mass loss of 0.6% until significant degradation occurs above ca. 250° C. The enthalpy of the sharp endotherm was measured as 75.8 mJ/mg.

Method 2: Compound (A) free base was dissolved in a solvent until solution was saturated. The solvent can be acetone, acetonitrile, chloroform, dimethylformamide, dimethylsulfoxide, ethyl acetate, isobutyl acetate, methanol, 2-methoxyethanol, 2-MeTHF, or methyl isobutyl ketone. The solution was allowed to stand at room temperature and the solvent was allowed to slowly evaporate. After crystallization had occurred, the solid was isolated and XRPD showed it to be polymorphic Form-I of Compound (A) free base.

Method 3: To approximately 200 mg of the dioxane solvate of Compound (A) free base was added water (6 mL). The mixture was slurried at room temperature for 1 week. The white suspension was collected by filtration and dried. XRPD showed it to be polymorphic Form-I of Compound (A) free base.

Example 2 Preparation of isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate succinate (Succinate Salt of Compound (A))

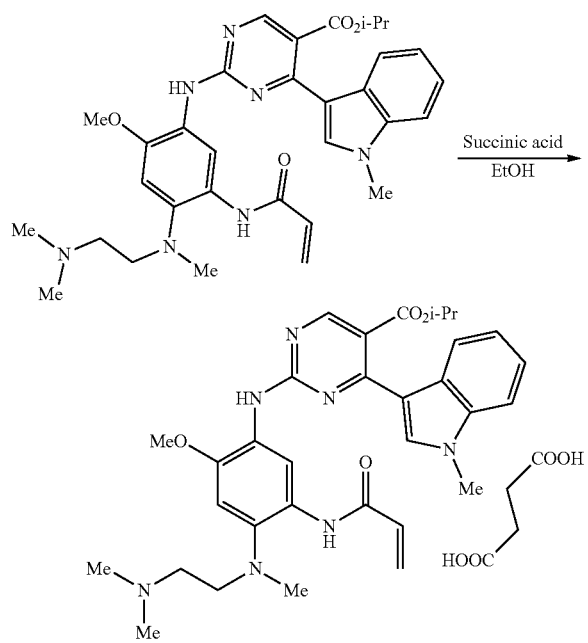

Method 1: Isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate (95 g, 162 mmol, 1.00 equiv.) was charged to a 2 L glass reactor and treated with a solution of succinic acid in ethanol (19.5 g, 165 mmol, 1.02 equiv. dissolved at 37° C. in EtOH, 200 Proof, 980 mL). Additional EtOH was used to rinse the flask and the filter (285 mL), and the rinse was added to the reaction mixture. The reaction mixture was heated to 75° C., aged for 1 h, and then cooled to 10° C. over 5 h. The product was isolated by filtration, washed with EtOH (2×90 mL), dried at 40° C. for 15 h to give 109 g of the title compound (96% yield). Purity (HPLC, a/a %, 99.64%).

$^1$H NMR (500 MHZ, DMSO-$d_6$) δ ppm 1.11 (d, J=6.36 Hz, 6H) 2.20 (s, 6H) 2.30 (br t, J=5.62 Hz, 2H) 2.72 (s, 3H) 2.88 (br t, J=5.62 Hz, 2H) 3.31 (s, 2H) 3.77-3.85 (m, 3H) 4.99 (dt, J=12.59, 6.17 Hz, 1H) 5.77 (br d, J=10.76 Hz, 1H) 6.27 (br d, J=16.63 Hz, 2H) 6.42 (dd, J=16.87, 10.03 Hz, 1H) 6.97-7.10 (m, 2H) 7.18 (t, J=7.58 Hz, 2H) 7.48 (d, J=8.31 Hz, 2H) 7.61-7.83 (m, 2H) 8.17 (br s, 1H) 8.57-8.71 (m, 2H) 8.84 (s, 1H) 10.14 (s, 1H).

Method 2: A mixture of isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (10.1 g, 17.2 mmol) and succinic acid (2.17 g, 18.4 mmol, 1.07 equiv.) in 2-methyl THF (200 mL) was temperature cycled between ambient and 40° C. at a rate of 0.1° C./min for 72 h. The slurry was stirred using a magnetic stirrer bar. After 72 h, the slurry was cooled to ambient and isolated by vacuum filtration through a sintered funnel. Filtration lasted ca. 2 minutes and the resulting solid was washed with 2-methyl THF (200 mL). The solid was dried in a vacuum oven at 40° C. for 6 h, to provide isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate succinate polymorphic Form-I (11.2 g, 15.9 mmol, 92% yield) as an off-white solid. Purity: 99.8%

$^1$H NMR (500 MHZ, DMSO-$d_6$) δ ppm 1.13 (d, J=6.23 Hz, 6H) 2.30 (s, 6H) 2.41 (s, 4H) 2.46 (br t, J=5.67 Hz, 2H) 2.72 (s, 3H) 2.96 (t, J=5.79 Hz, 2H) 3.88 (s, 3H) 5.01 (quin, J=6.27 Hz, 1H) 5.76-5.81 (m, 1H) 6.29 (dd, J=16.95, 1.89 Hz, 1H) 6.48 (dd, J=16.91, 10.13 Hz, 1H) 7.05 (s, 1H) 7.06 (d, J=7.10 Hz, 2H) 7.20 (t, J=7.67 Hz, 2H) 7.50 (d, J=8.28 Hz, 1H) 7.75 (br s, 1H) 8.18 (s, 1H) 8.65 (s, 1H) 8.67 (s, 1H) 8.82 (s, 1H) 10.05 (s, 1H).

Method 3: 2-Methyl THF (3 mL) was added to isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate (202.8 mg) to give a mobile slurry. In a separate vial, succinic acid (40.8 mg, 1.0 eq) was added to 2-methyl THF (1.0 mL). The slurry was added to the succinic acid solution over 5 minutes and the resulting mixture was temperature cycled between ambient (ca. 22° C.) and 40° C. in 4 h cycles over 48 h. The resulting solid material was isolated by vacuum filtration, washed with 2-methyl THF (3 mL) and dried under vacuum at ca. 22°C for 72 h to give isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate succinate polymorphic Form-I (177 mg, 73% yield).

XRPD data for polymorphic Form-I of the succinate salt of Compound (A) is shown in FIG. 4 and in Table 4 below.

TABLE 4

| Peak No. | Position [°2θ] | d-spacing [Å] | Rel. Intensity [%] |
|---|---|---|---|
| 1 | 8.3 | 10.6 | 89.8 |
| 2 | 9.9 | 9.0 | 100.0 |
| 3 | 10.5 | 8.4 | 6.9 |
| 4 | 10.8 | 8.2 | 7.2 |
| 5 | 11.4 | 7.7 | 20.6 |
| 6 | 11.7 | 7.5 | 64.8 |
| 7 | 12.4 | 7.2 | 5.7 |
| 8 | 14.3 | 6.2 | 42.2 |
| 9 | 14.7 | 6.0 | 5.2 |

TABLE 4-continued

| Peak No. | Position [°2θ] | d-spacing [Å] | Rel. Intensity [%] |
|---|---|---|---|
| 10 | 15.3 | 5.8 | 47.3 |
| 11 | 15.5 | 5.7 | 14.0 |
| 12 | 17.0 | 5.2 | 9.4 |
| 13 | 17.1 | 5.2 | 7.3 |
| 14 | 17.6 | 5.0 | 5.6 |
| 15 | 18.1 | 4.9 | 13.9 |
| 16 | 18.6 | 4.8 | 45.9 |
| 17 | 19.4 | 4.6 | 37.6 |
| 18 | 19.9 | 4.4 | 23.3 |
| 19 | 21.9 | 4.1 | 34.4 |
| 20 | 22.0 | 4.0 | 17.1 |
| 21 | 22.5 | 4.0 | 82.7 |
| 22 | 22.8 | 3.9 | 26.9 |
| 23 | 23.0 | 3.9 | 13.2 |
| 24 | 23.4 | 3.8 | 10.3 |
| 25 | 23.7 | 3.8 | 10.4 |
| 26 | 23.8 | 3.7 | 21.8 |
| 27 | 24.2 | 3.7 | 11.9 |
| 28 | 24.4 | 3.6 | 9.2 |
| 29 | 25.0 | 3.6 | 10.7 |
| 30 | 25.2 | 3.5 | 31.7 |
| 31 | 25.6 | 3.5 | 26.5 |
| 32 | 27.1 | 3.3 | 6.0 |
| 33 | 27.4 | 3.2 | 10.3 |
| 34 | 29.1 | 3.1 | 6.3 |
| 35 | 29.9 | 3.0 | 11.3 |
| 36 | 30.5 | 2.9 | 7.4 |
| 37 | 31.5 | 2.8 | 13.2 |
| 38 | 31.9 | 2.8 | 10.3 |
| 39 | 33.0 | 2.7 | 6.3 |
| 40 | 37.3 | 2.4 | 6.0 |

Table 5 displays the unit cell dimension of polymorphic Form-I of the succinate salt of Compound (A).

TABLE 5

| | |
|---|---|
| a/Å | 8.9138(4) |
| b/Å | 12.4546(5) |
| c/Å | 17.9647(5) |
| α/° | 79.441(3) |
| β/° | 88.061(3) |
| γ/° | 71.127(4) |
| Volume/Å$^3$ | 1854.52(13) |

Figure 5:
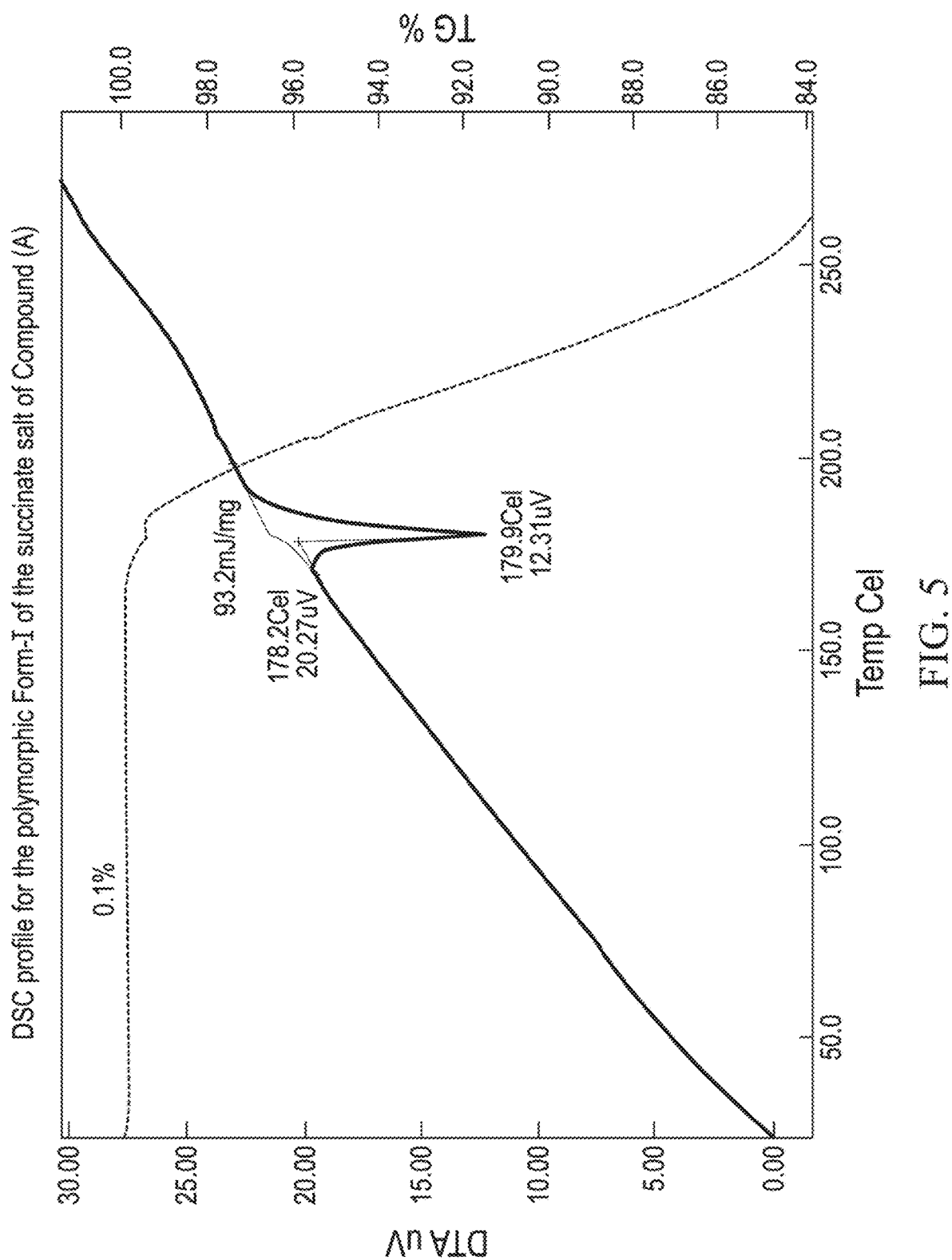
FIG. 5 is a DSC profile for the polymorphic Form-I of the succinate salt of Compound (A).

DSC profile for polymorphic Form-I of the succinate salt of Compound (A) is shown in FIG. 5. The profile displays an endothermic transition with an onset temperature of about 176.1° C. with a melt of 178.5° C., and an associated enthalpy of 99.5 mJ/mg.

Figure 6:
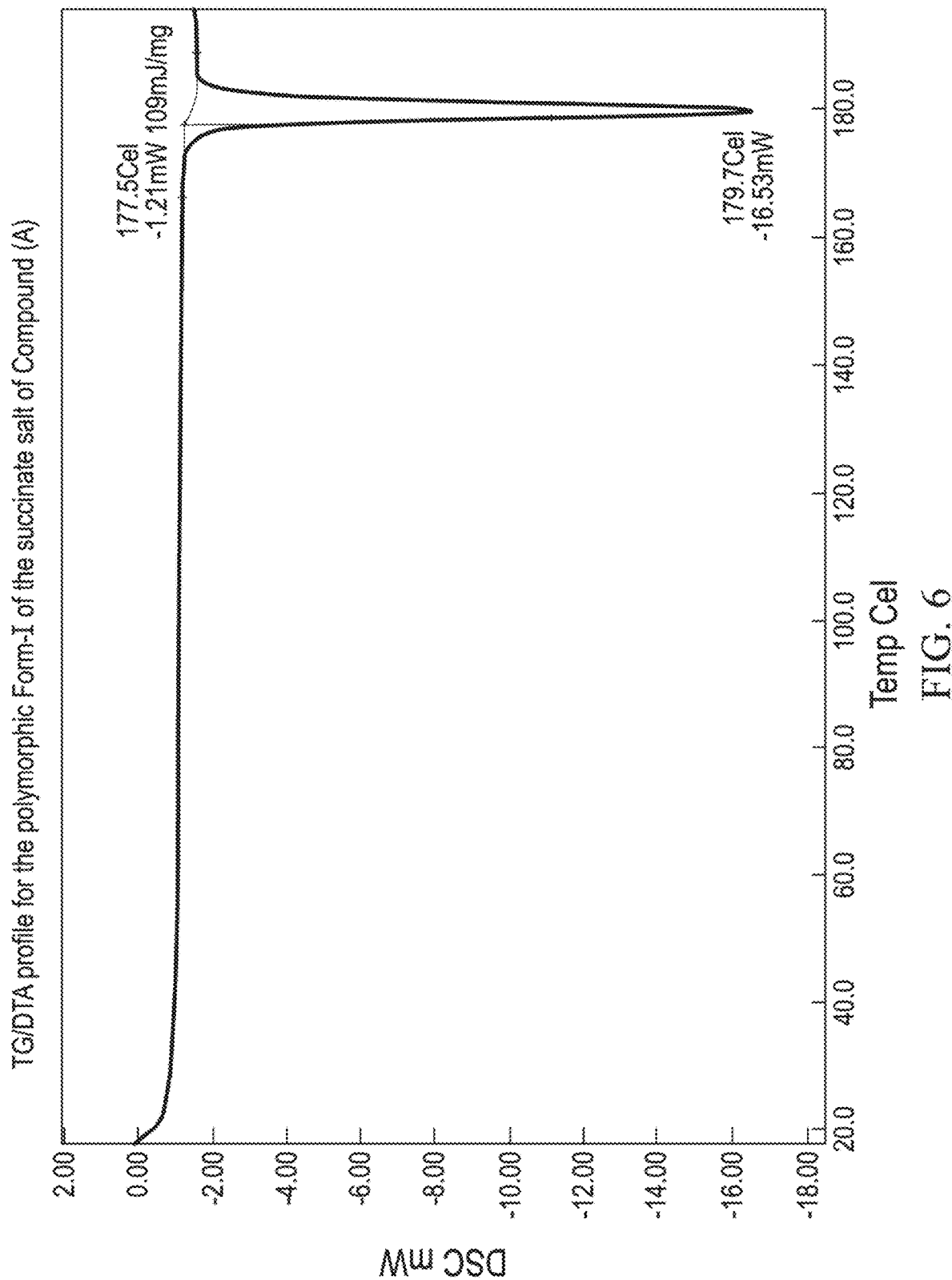
FIG. 6 is a TG/DTA profile for the polymorphic Form-I of the succinate salt of Compound (A).

TG/DAT profile for polymorphic Form-I of the succinate salt of Compound (A) succinate is shown in FIG. 6. The profile displays an endothermic transition with an onset temperature of about 176.4° C., which is accompanied by a mass loss of 0.1% up to 150±2° C. followed by a mass loss of 1.2% up to 175° C. at a temperature changing rate of 10° C. per minute from 25° C. to 300° C., and decomposition at about 176.4° C. to about 178.5° C.

Method 4: To Isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate. (400 mg) was added a solution of water saturated ethyl acetate (6 mL). To the resulting suspension was added a solution of succinic acid (89 mg) in methanol (1 mL). The mixture was warmed to 40° C.; a thick suspension was observed. Water (1 mL) was added causing the solid to dissolve. The solution was cooled to room temperature and the vial lid loosened to allow for slow evaporation of the solvents. After 18 hours a suspension was obtained which was filtered and then dried under vacuum to give 400 mg of solids, which is identified as succinate polymorphic Form-III of Compound (A).

Method 5: Isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (ca. 200 mg) was slurried in water saturated EtOAc (3 mL) at ambient temperature. To the slurry was added a succinic acid solution (41 mg in 500 µL of MeOH, 1.0 eq), causing dissolution. Water (50 µL) was added to increase the water content. The resulting solution was filtered using a 0.45 tm PTFE syringe filter and the clear solution was seeded with a small amount of pre-prepared Form III material and stored at ca. 2° C. for 72 h. The resulting solid was analyzed by XRPD to show as succinate polymorphic Form-III. The material was stored at ca. 2° C. and only isolated as appropriate.

Figure 7:
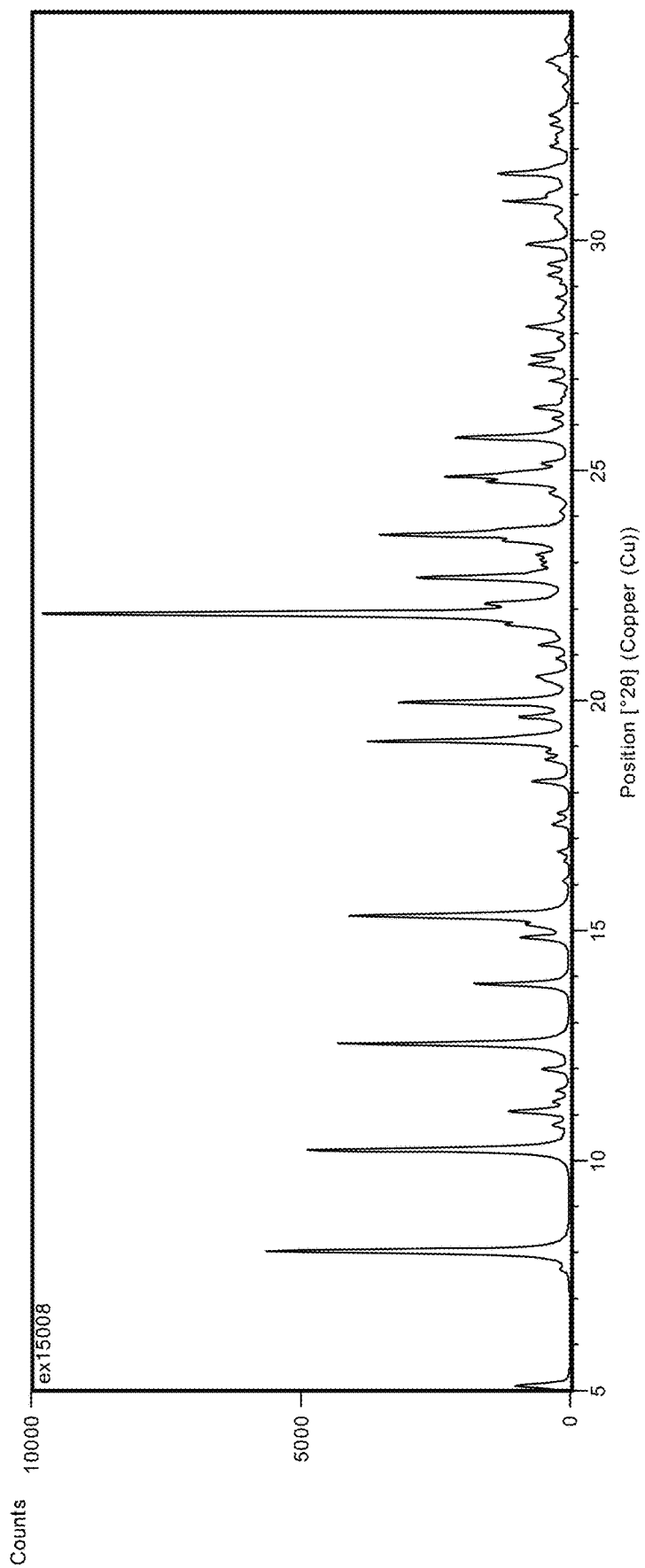
FIG. 7 is XRPD data for the polymorphic Form-III of the succinate salt of Compound (A).

XRPD data for polymorphic Form-III of the succinate salt of Compound (A) is shown in FIG. 7 and in Table 6 below.

TABLE 6

| Peak No. | Position [°2θ] | d-spacing [Å] | Rel. Intensity [%] |
|---|---|---|---|
| 1 | 5.1 | 17.3 | 10.2 |
| 2 | 8.0 | 11.0 | 56.1 |
| 3 | 10.2 | 8.6 | 49.0 |
| 4 | 11.1 | 8.0 | 11.4 |
| 5 | 12.0 | 7.4 | 5.3 |
| 6 | 12.5 | 7.1 | 43.0 |
| 7 | 13.8 | 6.4 | 17.8 |
| 8 | 14.8 | 6.0 | 9.3 |
| 9 | 15.3 | 5.8 | 40.8 |
| 10 | 18.2 | 4.9 | 7.1 |
| 11 | 19.1 | 4.6 | 37.3 |
| 12 | 19.6 | 4.5 | 9.6 |
| 13 | 20.0 | 4.4 | 32.1 |
| 14 | 20.5 | 4.3 | 6.3 |
| 15 | 21.2 | 4.2 | 5.9 |
| 16 | 21.9 | 4.1 | 100.0 |
| 17 | 22.1 | 4.0 | 15.8 |
| 18 | 22.7 | 3.9 | 28.4 |
| 19 | 23.6 | 3.8 | 35.0 |
| 20 | 24.7 | 3.6 | 13.9 |
| 21 | 24.9 | 3.6 | 23.2 |
| 22 | 25.2 | 3.5 | 5.4 |
| 23 | 25.7 | 3.5 | 21.3 |
| 24 | 26.4 | 3.4 | 6.8 |
| 25 | 27.3 | 3.3 | 7.8 |
| 26 | 27.5 | 3.2 | 7.1 |
| 27 | 28.1 | 3.2 | 8.2 |
| 28 | 29.9 | 3.0 | 8.1 |
| 29 | 30.9 | 2.9 | 12.3 |
| 30 | 31.5 | 2.8 | 13.3 |
| 31 | 36.5 | 2.5 | 5.8 |
| 32 | 37.2 | 2.4 | 5.4 |
| 33 | 39.9 | 2.3 | 5.3 |

Table 7 displays the unit cell dimension of polymorphic Form-III of succinate salt of Compound (A).

TABLE 7

| | |
|---|---|
| a/Å | 8.8701(6) |
| b/Å | 12.6948(9) |
| c/Å | 17.9192(13) |
| α/° | 75.120(6) |
| β/° | 87.650(6) |
| γ/° | 70.439(6) |
| Volume/Å$^3$ | 1835.3(2) |

Example 3 Preparation of isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate hydrobromide (Hydrobromide Salt of Compound (A))

2-Methyl THF (3 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate to give a mobile slurry. Aqueous HBr (200 µL, 1.66 M, 1.0 eq) was added dropwise with agitation to the 2-methyl THF slurry to give a red oil, followed by dissolution to a pale yellow solution. The solution was temperature cycled between ambient (ca. 22° C.) and 40° C. in 4 h cycles over 24 h. The resulting solid material was isolated by vacuum filtration, washed with 2-methyl THF (3 mL) and dried under vacuum at ca. 22° C. for 6 h to give isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate hydrobromide Form-I (209 mg, 89% yield).

Figure 8:
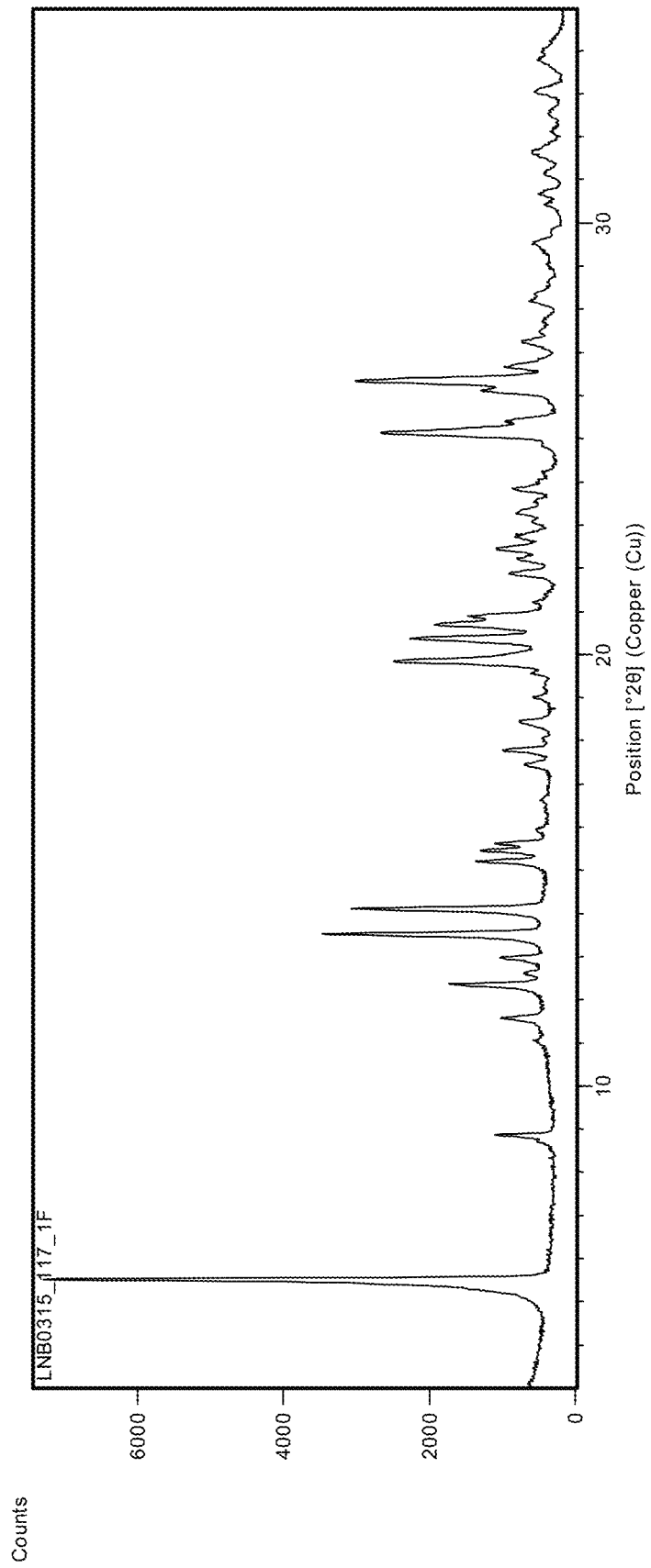
FIG. 8 is XRPD data for the polymorphic Form-I of the hydrobromide salt of Compound (A).

XRPD data for polymorphic Form-I of the hydrobromide salt of Compound (A) is shown in FIG. 8 and in Table 8 below.

TABLE 8

| Peak No. | Position [°2θ] | d-spacing [Å] | Rel. Intensity [%] |
|---|---|---|---|
| 1 | 5.5 | 16.0 | 100.0 |
| 2 | 8.9 | 10.0 | 11.5 |
| 3 | 11.6 | 7.6 | 10.0 |
| 4 | 12.4 | 7.2 | 19.4 |
| 5 | 13.0 | 6.8 | 10.2 |
| 6 | 13.5 | 6.5 | 45.1 |
| 7 | 14.1 | 6.3 | 39.4 |
| 8 | 15.2 | 5.8 | 14.8 |
| 9 | 15.5 | 5.7 | 13.8 |
| 10 | 15.6 | 5.7 | 11.1 |
| 11 | 17.4 | 5.1 | 5.2 |
| 12 | 17.8 | 5.0 | 9.7 |
| 13 | 18.4 | 4.8 | 6.2 |
| 14 | 19.8 | 4.5 | 31.4 |
| 15 | 20.4 | 4.4 | 28.3 |
| 16 | 20.7 | 4.3 | 23.2 |
| 17 | 20.9 | 4.3 | 16.0 |
| 18 | 21.9 | 4.1 | 8.6 |
| 19 | 22.2 | 4.0 | 7.1 |
| 20 | 22.4 | 4.0 | 11.2 |
| 21 | 22.7 | 3.9 | 7.5 |
| 22 | 23.3 | 3.8 | 7.2 |
| 23 | 23.8 | 3.7 | 8.4 |
| 24 | 25.1 | 3.5 | 34.4 |
| 25 | 25.4 | 3.5 | 8.7 |
| 26 | 26.1 | 3.4 | 15.1 |
| 27 | 26.3 | 3.4 | 39.8 |
| 28 | 26.7 | 3.3 | 10.0 |
| 29 | 27.2 | 3.3 | 7.1 |
| 30 | 28.2 | 3.2 | 5.6 |
| 31 | 29.5 | 3.0 | 5.2 |
| 32 | 31.6 | 2.8 | 5.9 |
| 33 | 33.1 | 2.7 | 5.3 |

$^1$H NMR (500 MHZ, DMSO-$d_6$) δ ppm 1.14 (d, J=6.23 Hz, 6H) 2.64 (s, 3H) 2.81 (s, 6H) 3.26-3.37 (m, 5H) 3.88 (d, J=1.42 Hz, 6H) 5.02 (quin, J=6.27 Hz, 1H) 5.77-5.84 (m, 1H) 6.33 (dd, J=16.98, 1.77 Hz, 1H) 6.81 (dd, J=16.91, 10.21 Hz, 1H) 7.03 (s, 1H) 7.09 (t, J=7.53 Hz, 1H) 7.21 (t, J=7.59 Hz, 1H) 7.51 (d, J=8.20 Hz, 1H) 7.74-7.91 (m, 1H) 8.09 (s, 1H) 8.56 (br s, 1H) 8.65 (s, 1H) 8.67 (s, 1H) 9.37 (br s, 1H) 9.51 (s, 1H).

Figure 9:
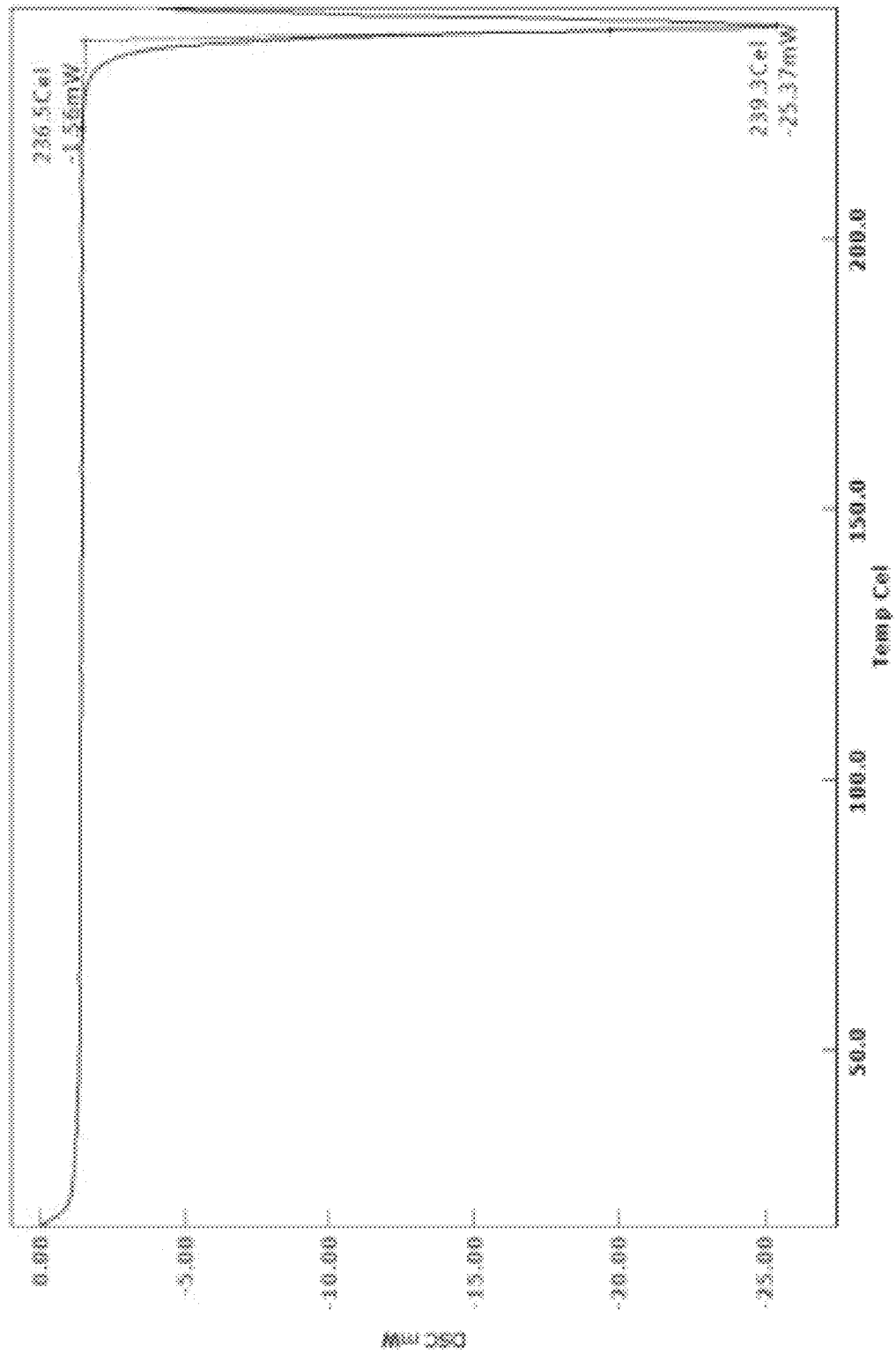
FIG. 9 is a DSC profile for the polymorphic Form-I of the hydrobromide salt of Compound (A).

DSC profile for polymorphic Form-I of the hydrobromide salt of Compound (A) is shown in FIG. 9. The profile displays a single sharp endotherm occurred at onset 236.5° C. DSC analysis was conducted up 260° C. to avoid excessive degradation of the sample.

Figure 10:
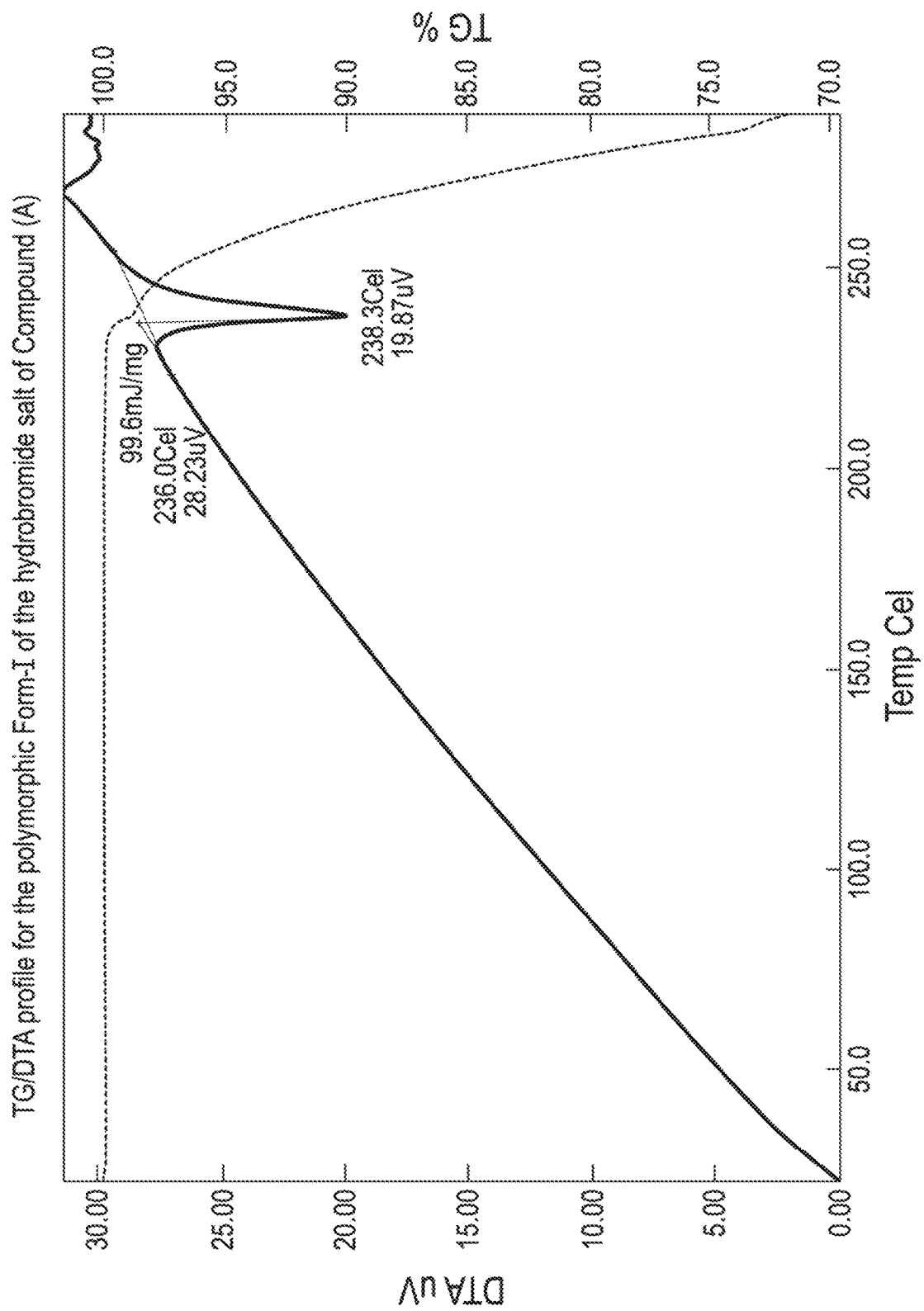
FIG. 10 is a TG/DTA profile for the polymorphic Form-I of the hydrobromide salt of Compound (A).

TG/DAT profile for polymorphic Form-I of the hydrobromide salt of Compound (A) succinate is shown in FIG. 10. The profile displays a single sharp endotherm observed at onset 236.0° C., with an associated enthalpy of 99.6 mJ/mg.

Example 4 Preparation of isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate hydrochloride (Hydrochloride Salt of Compound (A))

2-Methyl THF (3 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (202.6 mg) to give a mobile slurry. Aqueous HCl (200 TL, 1.66 M, 1.0 eq) was added dropwise with agitation to the 2-methyl THF slurry to give a pale yellow solution. The resulting solution was filtered using a PTFE syringe filter and allowed to evaporate under ambient conditions (ca. 22° C.) for 72 h, followed by vacuum drying for 24 h to give isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate hydrochloride Form-I. Recovery was assumed to be 100% due to complete evaporation of the sample.

Figure 11:
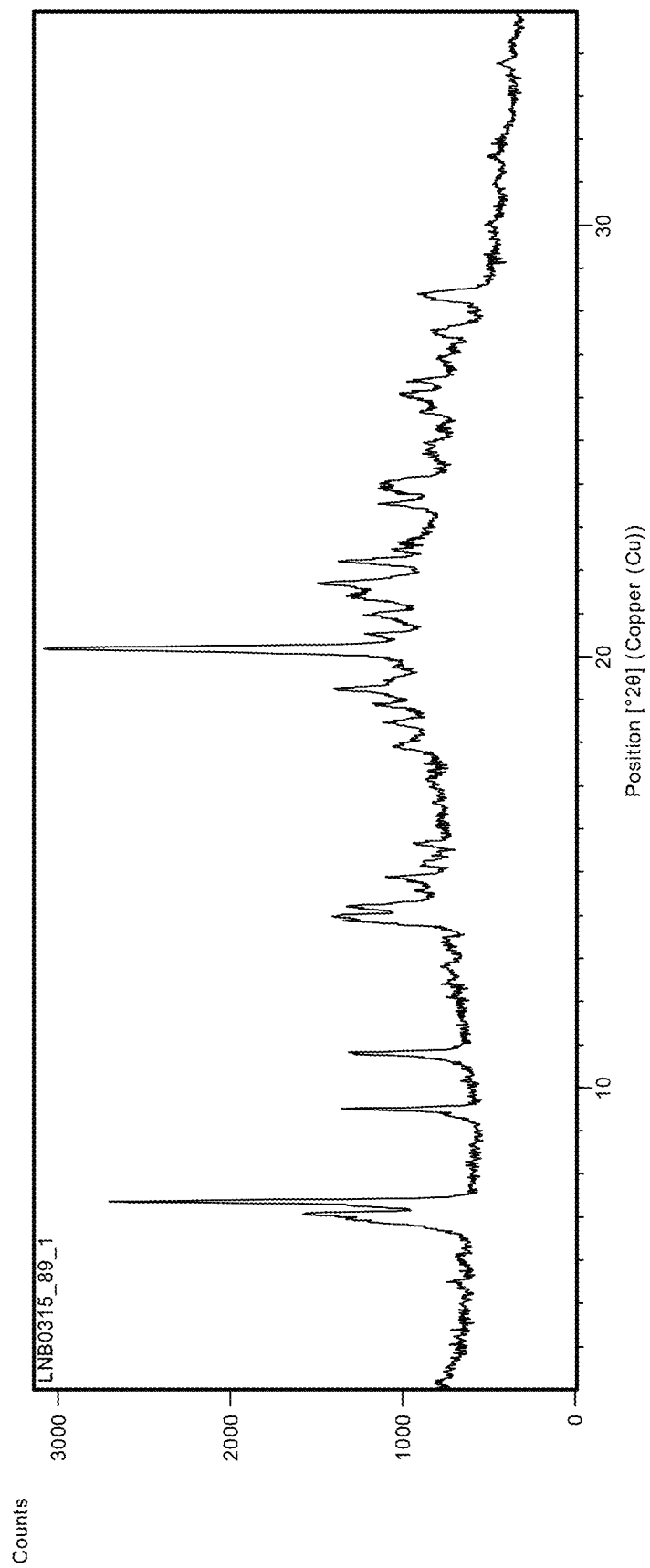
FIG. 11 is XRPD data for the polymorphic Form-I of the hydrochloride salt of Compound (A).

XRPD data for polymorphic Form-I of the hydrochloride salt of Compound (A) is shown in FIG. 11 and in Table 9 below.

TABLE 9

| Peak No. | Position [°2θ] | d-spacing [Å] | Rel. Intensity [%] |
|---|---|---|---|
| 1 | 7.1 | 12.5 | 42.4 |
| 2 | 7.4 | 12.0 | 93.4 |
| 3 | 9.5 | 9.3 | 34.7 |
| 4 | 10.8 | 8.2 | 29.4 |
| 5 | 13.9 | 6.4 | 28.1 |
| 6 | 14.2 | 6.2 | 25.6 |
| 7 | 14.9 | 6.0 | 16.9 |
| 8 | 15.2 | 5.8 | 7.2 |
| 9 | 15.7 | 5.7 | 7.5 |
| 10 | 17.9 | 4.9 | 10.4 |
| 11 | 18.5 | 4.8 | 11.5 |
| 12 | 18.9 | 4.7 | 15.4 |
| 13 | 19.2 | 4.6 | 25.2 |
| 14 | 20.2 | 4.4 | 100.0 |
| 15 | 20.5 | 4.3 | 17.8 |
| 16 | 21.0 | 4.2 | 16.1 |
| 17 | 21.4 | 4.1 | 20.7 |
| 18 | 21.7 | 4.1 | 30.6 |
| 19 | 22.2 | 4.0 | 25.3 |
| 20 | 23.5 | 3.8 | 14.9 |
| 21 | 24.0 | 3.7 | 15.0 |
| 22 | 24.8 | 3.6 | 6.1 |
| 23 | 25.7 | 3.5 | 10.0 |
| 24 | 26.1 | 3.4 | 15.8 |
| 25 | 26.4 | 3.4 | 15.4 |
| 26 | 27.5 | 3.2 | 11.4 |
| 27 | 28.4 | 3.1 | 17.2 |

$^1$H NMR: $^1$H NMR (500 MHZ, DMSO-$d_6$) δ ppm 1.14 (d, J=6.23 Hz, 6H) 2.64 (s, 3H) 2.81 (s, 6H) 3.26-3.37 (m, 5H) 3.88 (d, J=1.42 Hz, 6H) 5.02 (quin, J=6.27 Hz, 1H) 5.77-5.84 (m, 1H) 6.33 (dd, J=16.98, 1.77 Hz, 1H) 6.81 (dd, J=16.91, 10.21 Hz, 1H) 7.03 (s, 1H) 7.09 (t, J=7.53 Hz, 1H) 7.21 (t, J=7.59 Hz, 1H) 7.51 (d, J=8.20 Hz, 1H) 7.74-7.91 (m, 1H) 8.09 (s, 1H) 8.56 (br s, 1H) 8.65 (s, 1H) 8.67 (s, 1H) 9.37 (br s, 1H) 9.51 (s, 1H).

Figure 12:
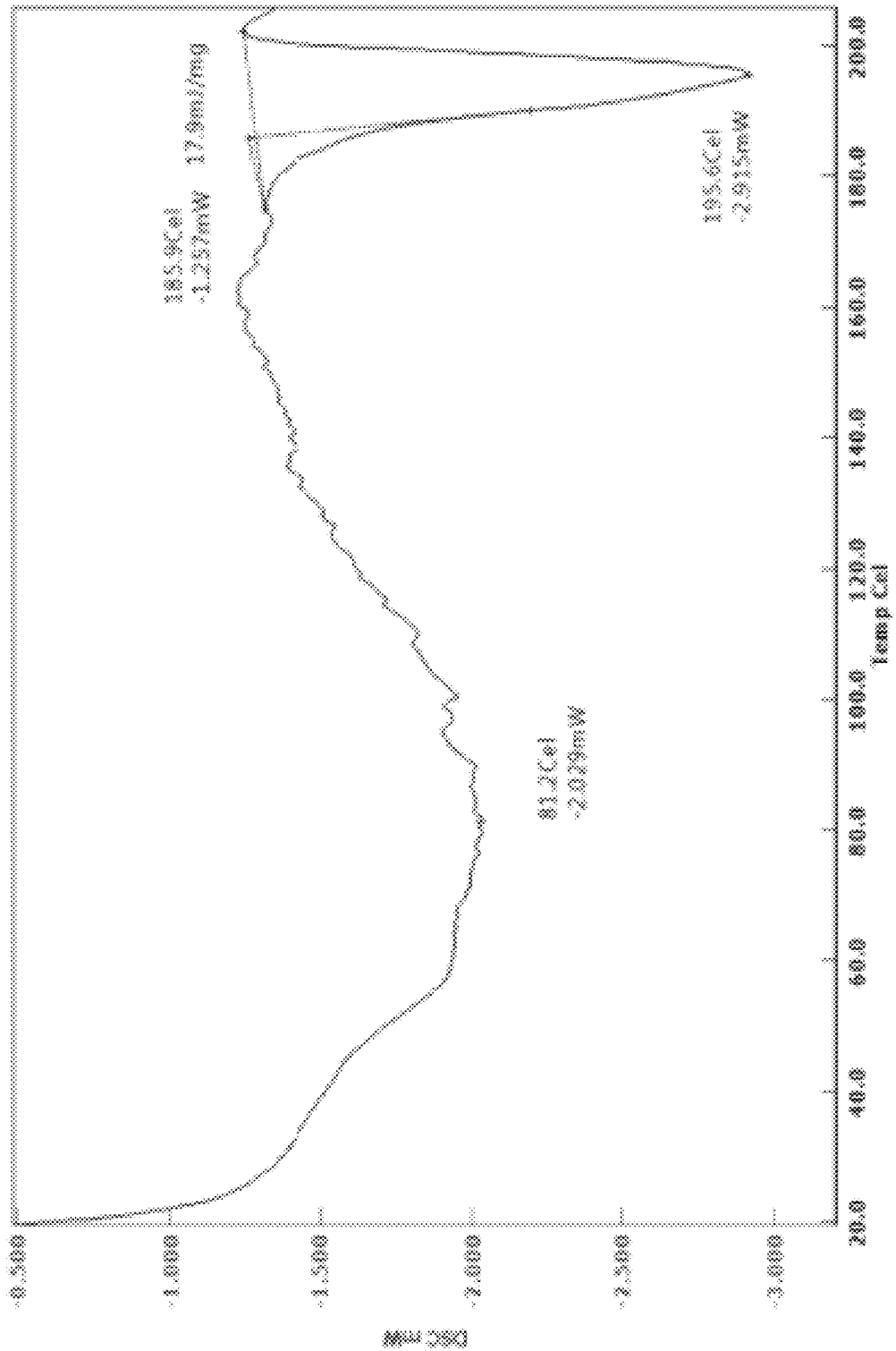
FIG. 12 is a DSC profile for the polymorphic Form-I of the hydrochloride salt of Compound (A).

DSC profile for polymorphic Form-I of the hydrochloride salt of Compound (A) is shown in FIG. 12. The profile displays a large broad endotherm observed from the onset of heating (loss of entrained solvent), followed immediately by a sharp endotherm at onset ca. 186° C.

Figure 13:
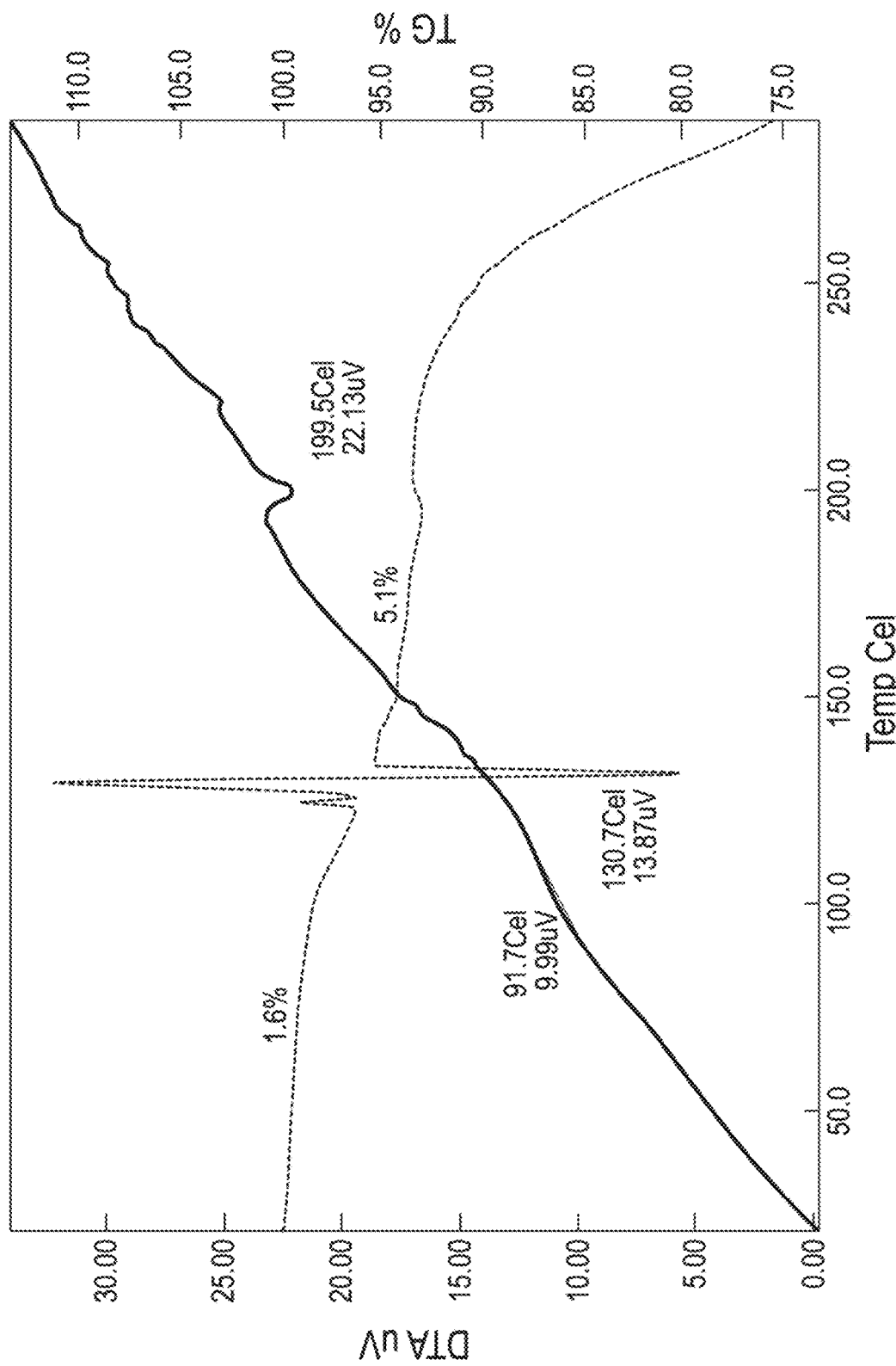
FIG. 13 is a TG/DTA profile for the polymorphic Form-I of the hydrochloride salt of Compound (A).

TG/DAT profile for polymorphic Form-I of the hydrochloride salt of Compound (A) succinate is shown in FIG. 13. The profile displays a gradual loss of ca. 1.6% mass from the onset of heating that is likely due to entrained solvent. An unusual response with a sharp increase/decrease was noted in the TGA trace between 100-150° C., which was present in repeated runs. While the exact reason for this pattern is unknown, it could potentially be due to rapid loss (bubbling) of solvent from the material. A final small endotherm with a minimum at 199.5° C. was observed before the onset of decomposition at ca. 210° C.

Example 5 Preparation of isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate sulfate (Sulfate Salt of Compound (A))

2-Methyl THF (3 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (199.2 mg) to give a mobile slurry. Aqueous $H_2SO_4$ (200 µL, 1.77 M, 1.0 eq) was added dropwise with agitation to the 2-methyl THF slurry to give a biphasic solution with a pale yellow/cloudy upper phase and deep red oily lower phase. The biphasic solution was seeded with a small amount of sulfate Form-I (ca. 1% w/w) and allowed to stand at ambient temperature (ca. 22° C.) for 1 h. After 1 h, the seed material had caused crystallization of the red oil/gum to give a pale yellow solid. The resulting solid was temperature cycled in the aqueous 2-methyl THF medium for 24 h between ambient and 40° C. in 4 h cycles. Post-temperature cycling, the material was isolated by vacuum filtration and washed with heptane (2 mL). The material was subsequently dried under vacuum at ca. 22° C. in the presence of MgSO4 for 72 h to give isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate sulfate Form-I (157 mg, 68% yield).

Figure 14:
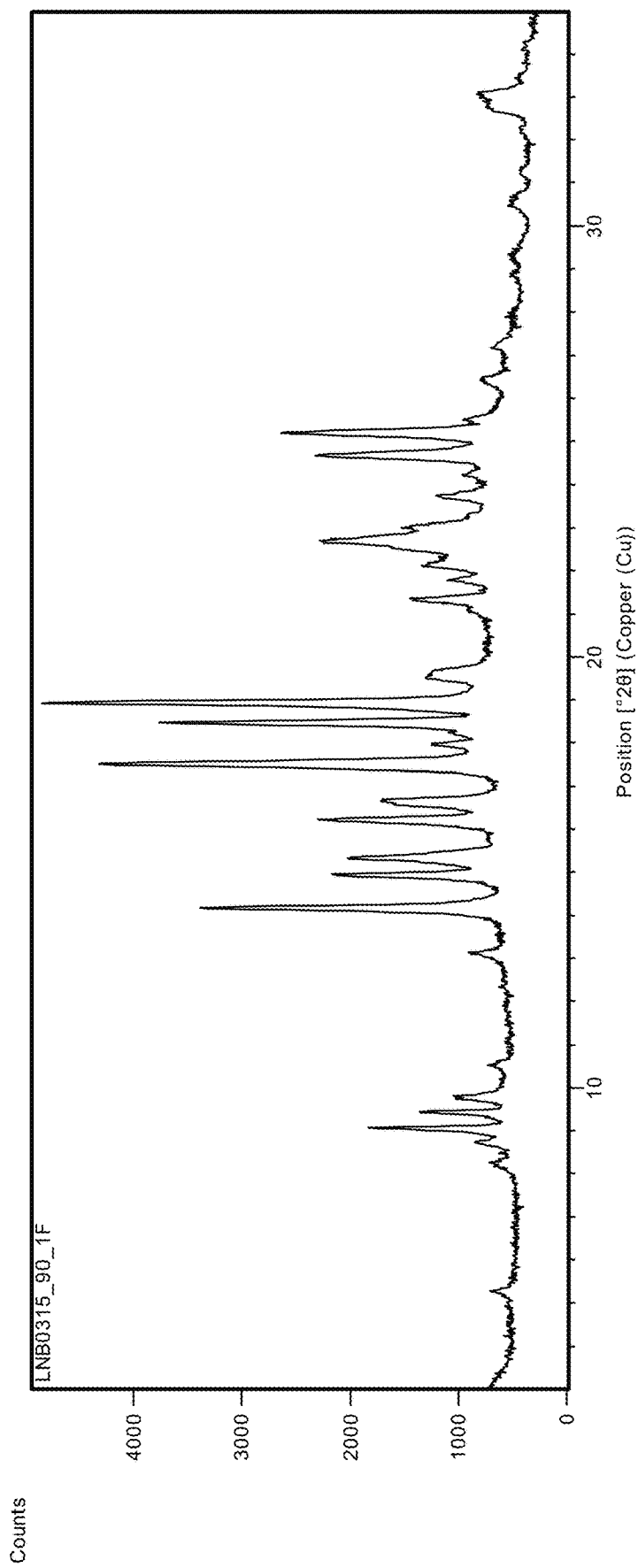
FIG. 14 is XRPD data for the polymorphic Form-I of the sulfate salt of Compound (A).

XRPD data for polymorphic Form-I of the sulfate salt of Compound (A) is shown in FIG. 14 and in Table 10 below.

TABLE 10

| Peak No. | Position [°2θ] | d-spacing [Å] | Rel. Intensity [%] |
|---|---|---|---|
| 1 | 8.7 | 10.1 | 8.3 |
| 2 | 9.1 | 9.8 | 32.3 |
| 3 | 9.4 | 9.4 | 20.9 |
| 4 | 9.8 | 9.0 | 12.0 |
| 5 | 13.1 | 6.8 | 7.4 |
| 6 | 14.2 | 6.3 | 67.2 |
| 7 | 14.9 | 5.9 | 36.5 |
| 8 | 15.3 | 5.8 | 33.9 |
| 9 | 16.2 | 5.5 | 40.1 |
| 10 | 16.7 | 5.3 | 25.7 |
| 11 | 17.5 | 5.1 | 89.0 |
| 12 | 18.0 | 4.9 | 14.6 |
| 13 | 18.5 | 4.8 | 75.2 |
| 14 | 18.9 | 4.7 | 100.0 |
| 15 | 19.6 | 4.5 | 15.0 |
| 16 | 21.3 | 4.2 | 18.9 |
| 17 | 21.8 | 4.1 | 10.8 |
| 18 | 22.1 | 4.0 | 16.3 |
| 19 | 22.7 | 3.9 | 39.9 |
| 20 | 23.0 | 3.9 | 20.9 |
| 21 | 23.7 | 3.8 | 14.4 |
| 22 | 24.2 | 3.7 | 9.2 |
| 23 | 24.7 | 3.6 | 41.9 |
| 24 | 25.2 | 3.5 | 50.1 |
| 25 | 25.5 | 3.5 | 9.9 |
| 26 | 26.4 | 3.4 | 6.5 |
| 27 | 32.7 | 2.7 | 9.3 |
| 28 | 33.1 | 2.7 | 11.6 |

$^1$H NMR (500 MHZ, DMSO-$d_6$) δ ppm 1.12-1.16 (m, 7H) 1.32 (dd, J=11.90, 8.99 Hz, 1H) 1.75-1.87 (m, 1H) 1.91-1.97 (m, 1H) 2.64 (s, 3H) 2.83 (d, J=3.78 Hz, 6H) 3.25-3.36 (m, 4H) 3.56 (td, J=7.98, 6.42 Hz, 1H) 3.88 (d, J=1.42 Hz, 6H) 5.03 (quin, J=6.25 Hz, 1H) 5.78-5.85 (m, 1H) 6.34 (dd, J=16.98, 1.77 Hz, 1H) 6.69 (dd, J=16.91, 10.21 Hz, 1H) 7.03 (s, 1H) 7.08 (t, J=7.56 Hz, 1H) 7.21 (t, J=7.67 Hz, 1H) 7.51 (d, J=8.28 Hz, 1H) 7.77-7.90 (m, 1H) 8.09 (s, 1H) 8.55 (br s, 1H) 8.66 (s, 1H) 8.68 (s, 1H) 9.21 (br s, 1H) 9.47 (s, 1H).

Figure 15A:
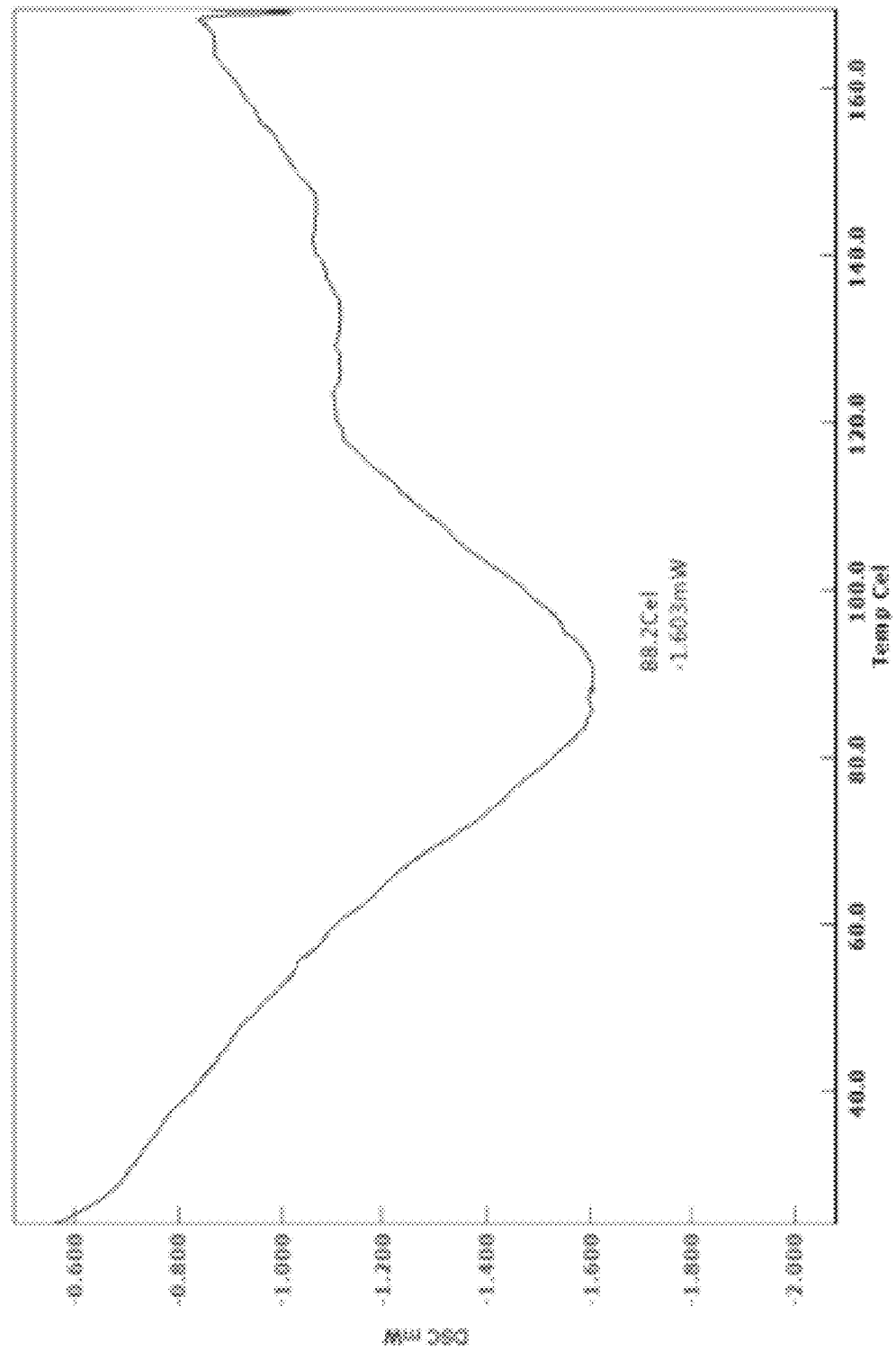
FIG. 15A is a DSC profile during a 1st heating cycle for the polymorphic Form-I of the sulfate salt of Compound (A).
Figure 15B:
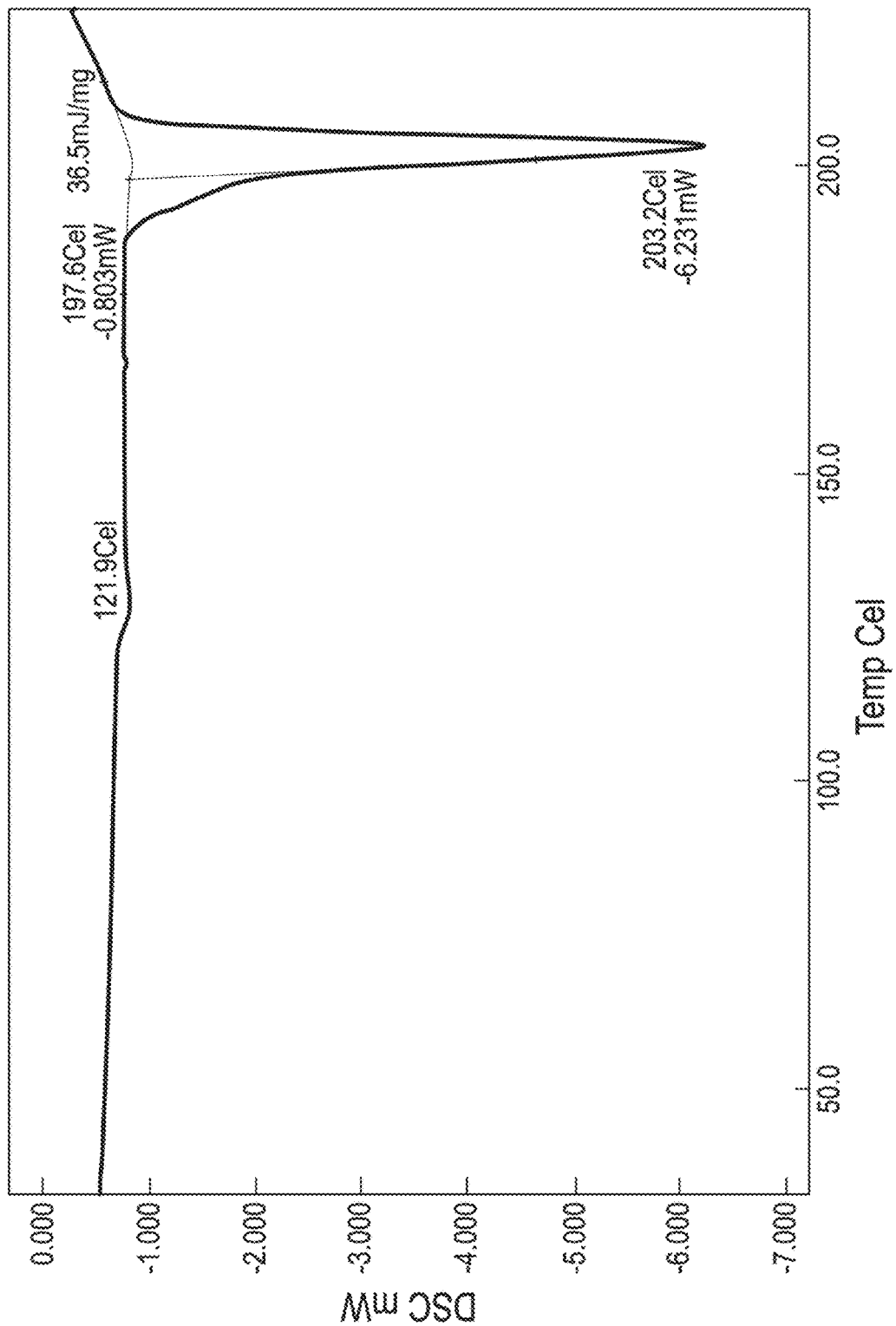
FIG. 15B is a DSC profile during a 2nd heating cycle for the polymorphic Form-I of the sulfate salt of Compound (A).

DSC profile for polymorphic Form-I of the sulfate salt of Compound (A) is shown in FIGS. 15A and 15B. The DSC method was modified to examine the nature of the sharp mass loss around 100° C. The DSC method employed involved the following temperature profile: 20° C.-180° C. 1st heating cycle); 180° C.-20° C. 1st cooling cycle); 20° C.-240° C. 2nd heating cycle); 240° C.-20° C. (2nd cooling cycle), 20° C.-240° C. 3rd heating Cycle).

In the first DSC heating cycle, a single broad endotherm was observed with a minimum at 88.2° C., likely due to the loss of entrained/bound solvent. The second heating cycle highlighted a potential glass transition at 121.9° C., followed by a large endotherm at onset 197.6° C., with an associated enthalpy of 36.5 mJ/mg.

Figure 16:
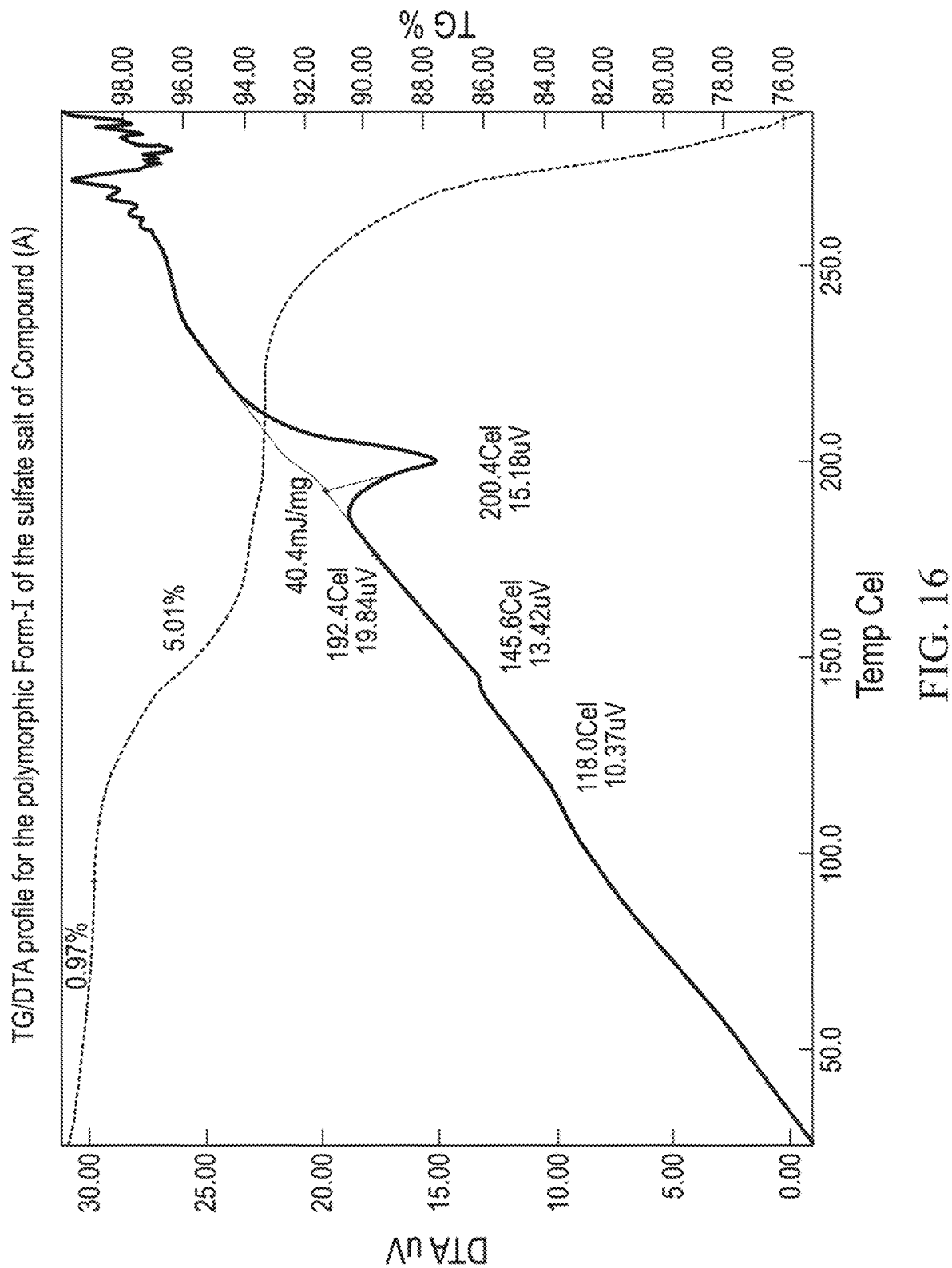
FIG. 16 is a TG/DTA profile for the polymorphic Form-I of the sulfate salt of Compound (A).

TG/DAT profile for polymorphic Form-I of the sulfate salt of Compound (A) is shown in FIG. 16. The profile displays a gradual loss of ca. 1.0% mass from the onset of heating that is likely due to entrained solvent. A subsequent sharp loss of ca. 5.0% mass was noted at onset ca. 100° C., with two associated broad endotherms (minima at 118.0° C. and 145.6° C.). A final large endotherm, likely to be melting, occurs at onset 192.4° C. with an associated enthalpy of 40.4 mJ/mg.

Example 6 Preparation of isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate tosylate (Tosylate Salt of Compound (A))

2-Methyl THF (3 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (198.8 mg) to give a mobile slurry. In a separate vial, p-TsOH·H$_2$O (67.4 mg, 1.0 eq) was dissolved in 2-methyl THF (1 mL) and the resulting solution was added dropwise to the API slurry over 5 minutes. Immediate precipitation of a red gummy solid was observed, which slowly redissolved with shaking at ambient (ca. 22° C.). The solution was temperature cycled between ambient and 40° C. in 4 h cycles over 24 h. The resulting solid was isolated by vacuum filtration and washed with heptane (2 mL). The material was subsequently dried under vacuum at ca. 22° C. in the presence of MgSO4 for 72 h to give isopropyl 2-((5-acrylamido-4-((2-(dimethylamino)ethyl) (methyl)

amino)-2-methoxyphenyl)amino)-4-(1-methyl-1H-indol-3-yl)pyrimidine-5-carboxylate tosylate Form-I (129 mg, 50% yield).

Figure 17:
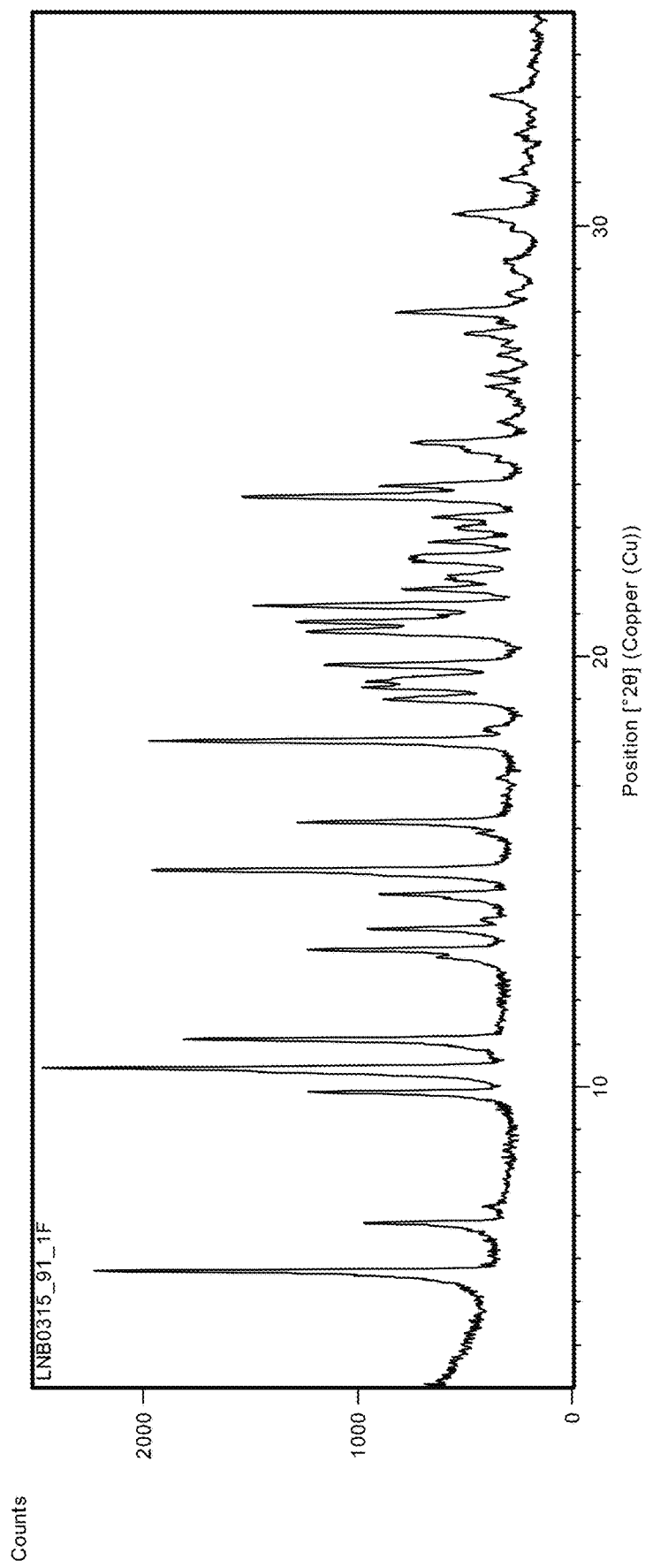
FIG. 17 is XRPD data for the polymorphic Form-I of the tosylate salt of Compound (A).

XRPD data for polymorphic Form-I of the tosylate salt of Compound (A) is shown in FIG. 17 and in Table 11 below.

TABLE 11

| Peak No. | Position [°2θ] | d-spacing [Å] | Rel. Intensity [%] |
| --- | --- | --- | --- |
| 1 | 5.7 | 15.5 | 83.5 |
| 2 | 6.8 | 13.0 | 29.0 |
| 3 | 9.9 | 9.0 | 43.2 |
| 4 | 10.4 | 8.5 | 100.0 |
| 5 | 11.1 | 8.0 | 69.6 |
| 6 | 13.2 | 6.7 | 43.5 |
| 7 | 13.7 | 6.5 | 30.6 |
| 8 | 14.5 | 6.1 | 28.3 |
| 9 | 15.0 | 5.9 | 76.4 |
| 10 | 16.1 | 5.5 | 45.7 |
| 11 | 18.0 | 4.9 | 77.8 |
| 12 | 19.0 | 4.7 | 27.1 |
| 13 | 19.3 | 4.6 | 32.6 |
| 14 | 19.4 | 4.6 | 30.9 |
| 15 | 19.8 | 4.5 | 39.1 |
| 16 | 20.6 | 4.3 | 44.7 |
| 17 | 20.8 | 4.3 | 47.0 |
| 18 | 21.2 | 4.2 | 55.9 |
| 19 | 21.6 | 4.1 | 23.4 |
| 20 | 21.8 | 4.1 | 14.0 |
| 21 | 22.3 | 4.0 | 22.2 |
| 22 | 22.3 | 4.0 | 22.6 |
| 23 | 22.7 | 3.9 | 18.0 |
| 24 | 23.0 | 3.9 | 13.4 |
| 25 | 23.2 | 3.8 | 18.4 |
| 26 | 23.7 | 3.8 | 59.3 |
| 27 | 24.0 | 3.7 | 29.1 |
| 28 | 25.0 | 3.6 | 24.0 |
| 29 | 26.3 | 3.4 | 8.9 |
| 30 | 26.5 | 3.4 | 8.8 |
| 31 | 27.0 | 3.3 | 6.5 |
| 32 | 27.5 | 3.2 | 13.7 |
| 33 | 28.0 | 3.2 | 27.4 |
| 34 | 28.4 | 3.1 | 5.5 |
| 35 | 29.1 | 3.1 | 5.1 |
| 36 | 29.9 | 3.0 | 5.1 |
| 37 | 30.3 | 3.0 | 16.2 |
| 38 | 31.1 | 2.9 | 6.7 |
| 39 | 33.0 | 2.7 | 9.4 |

$^1$H NMR (500 MHZ, CHLOROFORM-d) δ ppm 1.06 (br d, J=6.15 Hz, 6H) 1:25 (d, J=6.15 Hz, 1H) 1.64-1.95 (m, 1H) 2.00 (br dd, J=11.63, 6.27 Hz, 1H) 2.34 (s, 3H) 2.63 (s, 3H) 2.79 (s, 6H) 3.07 (br t, J=5.40 Hz, 2H) 3.20 (t, J=5.60 Hz, 2H) 3.86-3.98 (m, 6H) 5.02 (dt, J=12.45, 6.23 Hz, 1H) 5.59-5.64 (m, 1H) 6.41 (dd, J=16.79, 1.97 Hz, 1H) 6.65 (s, 1H) 6.86 (dd, J=16.75, 10.21 Hz, 1H) 7.13-7.25 (m, 4H) 7.34 (d, J=8.20 Hz, 1H) 7.49-7.67 (m, 1H) 7.76 (d, J=8.20 Hz, 2H) 7.91 (br s, 1H) 8.42-8.64 (m, 1H) 8.89 (s, 1H) 9.05 (s, 1H) 9.67 (s, 1H) 10.58-10.80 (m, 1H).

Figure 18:
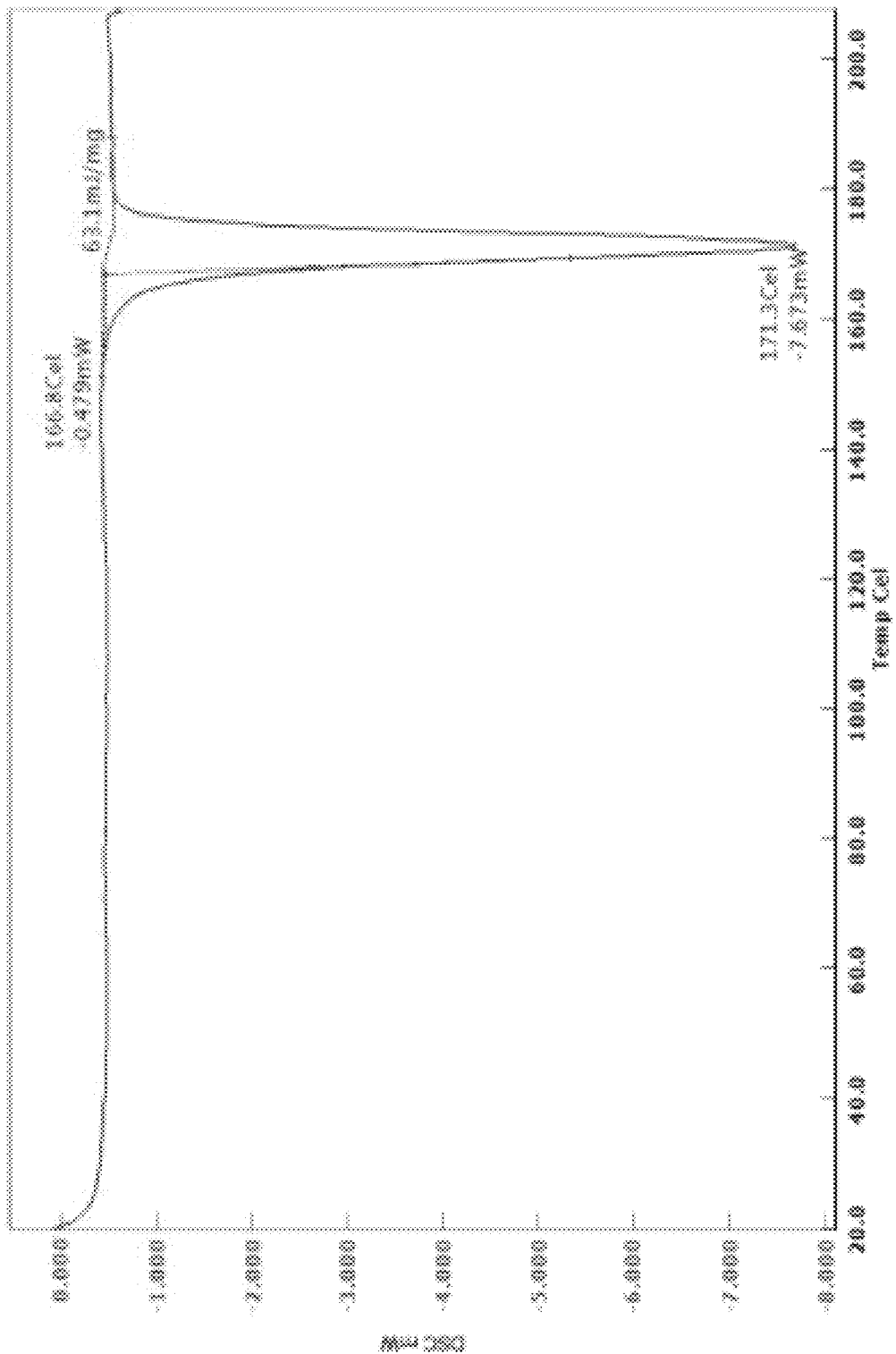
FIG. 18 is a DSC profile for the polymorphic Form-I of the tosylate salt of Compound (A).

DSC profile for polymorphic Form-I of the tosylate salt of Compound (A) is shown in FIG. 18. The profile displays a single sharp endotherm at onset 166.8° C., with an associated enthalpy of 63.1 mJ/mg.

Figure 19:
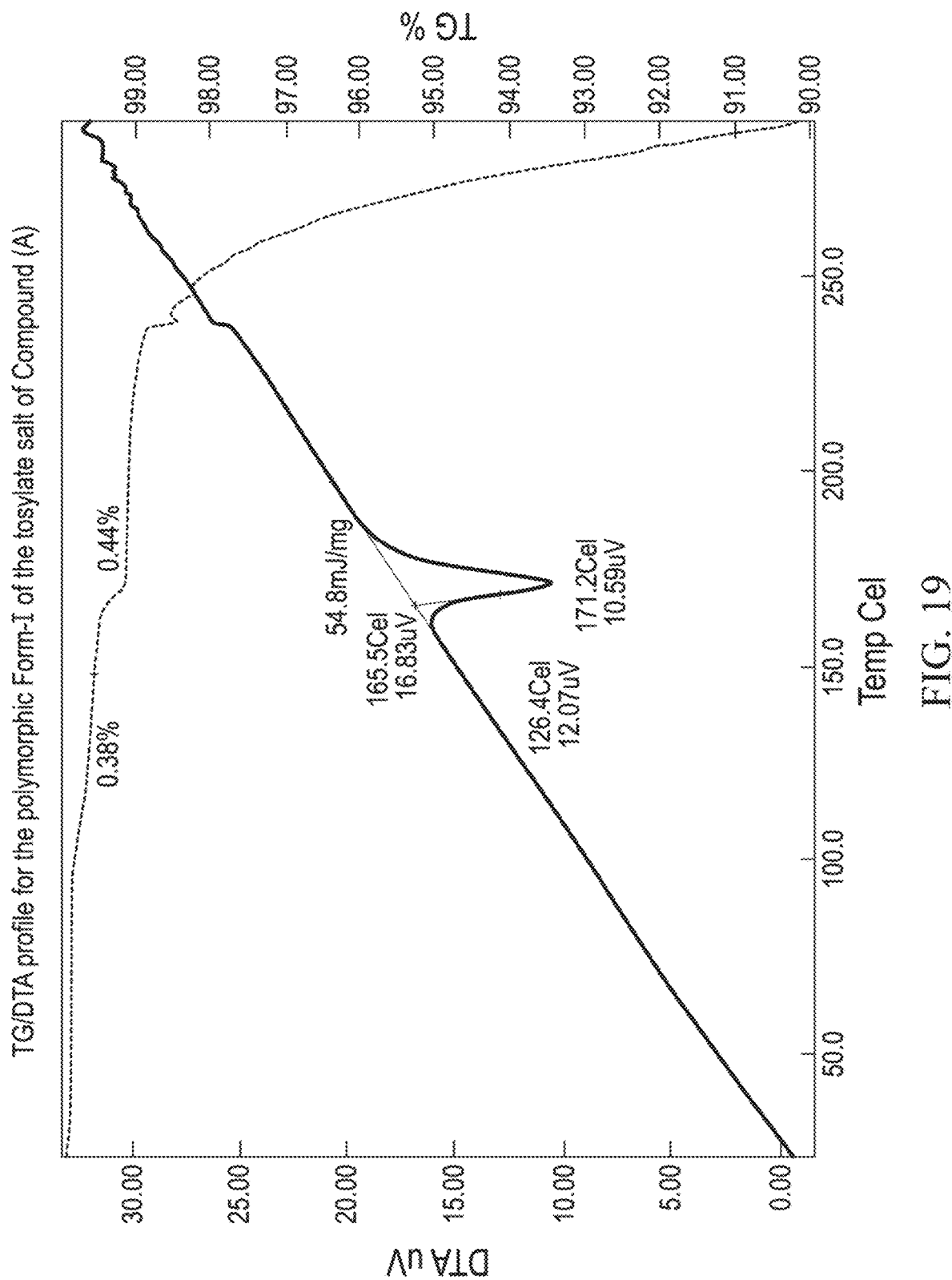
FIG. 19 is a TG/DTA profile for the polymorphic Form-I of the tosylate salt of Compound (A).

TG/DAT profile for polymorphic Form-I of the tosylate salt of Compound (A) is shown in FIG. 19. The profile displays a gradual loss of ca. 0.4% mass from ca. 100° C. that is associated with a very shallow endotherm with a minimum at 126.4° C. A subsequent sharper loss of ca. 0.4% mass was observed, with an associated broad endotherm (melt) at onset 165.5° C. and a related enthalpy of 54.8 mJ/mg.

Example 7 Preparation of isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate mesylate (Mesylate Salt of Compound (A))

Anisole (3 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (200.4 mg) to give a mobile slurry. In a separate vial, a stock solution of MsOH (1.71 M in anisole) was prepared, of which 200 μL (1.0 eq) was added to the API slurry over 5 minutes. Immediate precipitation of a red gummy solid was observed, which slowly redissolved with shaking at ambient (ca. 22° C.). The solution was temperature cycled between ambient and 40° C. in 4 h cycles over 96 h. The resulting solid was isolated by vacuum filtration and dried under vacuum at ca. 22° C. in the presence of MgSO4 for 24 h to give isopropyl 2-((5-acrylamido-4-((2-(dimethylamino)ethyl) (methyl)amino)-2-methoxyphenyl) amino)-4-(1-methyl-1H-indol-3-yl)pyrimidine-5-carboxylate mesylate Form-III (176 mg, 75% yield).

Figure 20:
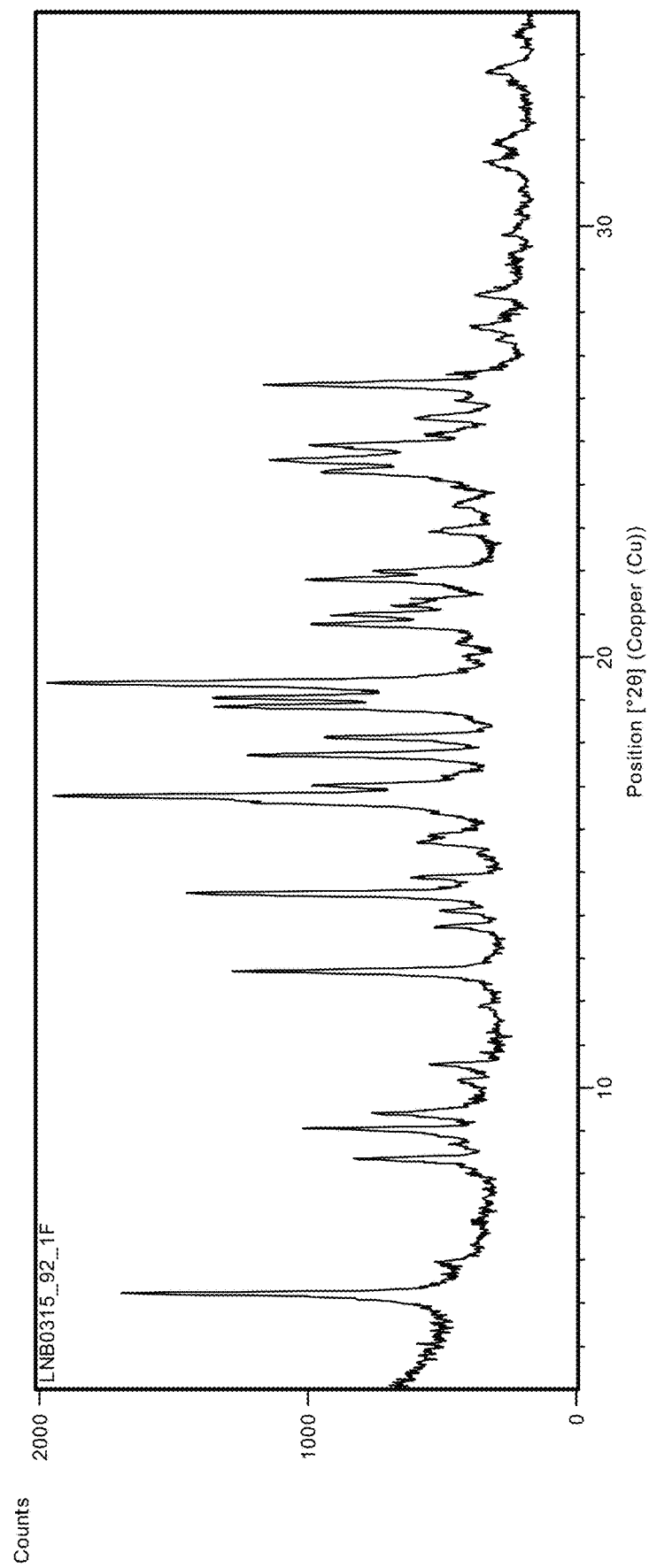
FIG. 20 is XRPD data for the polymorphic Form-III of the mesylate salt of Compound (A).

XRPD data for polymorphic Form-III of the mesylate salt of Compound (A) is shown in FIG. 20 and in Table 12 below.

TABLE 12

| Peak No. | Position [°2θ] | d-spacing [Å] | Rel. Intensity [%] |
| --- | --- | --- | --- |
| 1 | 5.2 | 16.9 | 74.2 |
| 2 | 5.9 | 14.9 | 7.4 |
| 3 | 8.3 | 10.6 | 31.0 |
| 4 | 8.7 | 10.2 | 10.2 |
| 5 | 9.1 | 9.8 | 42.9 |
| 6 | 9.4 | 9.4 | 27.5 |
| 7 | 10.2 | 8.7 | 7.9 |
| 8 | 10.5 | 8.4 | 15.5 |
| 9 | 12.7 | 7.0 | 58.6 |
| 10 | 13.7 | 6.4 | 13.7 |
| 11 | 14.1 | 6.3 | 12.2 |
| 12 | 14.5 | 6.1 | 68.6 |
| 13 | 14.9 | 6.0 | 18.8 |
| 14 | 15.7 | 5.6 | 16.7 |
| 15 | 16.8 | 5.3 | 97.0 |
| 16 | 17.0 | 5.2 | 40.5 |
| 17 | 17.7 | 5.0 | 54.6 |
| 18 | 18.1 | 4.9 | 37.6 |
| 19 | 18.8 | 4.7 | 61.8 |
| 20 | 19.1 | 4.7 | 62.3 |
| 21 | 19.4 | 4.6 | 100.0 |
| 22 | 20.8 | 4.3 | 41.6 |
| 23 | 21.0 | 4.2 | 34.5 |
| 24 | 21.8 | 4.1 | 43.4 |
| 25 | 22.0 | 4.0 | 27.6 |
| 26 | 22.9 | 3.9 | 15.0 |
| 27 | 23.5 | 3.8 | 10.9 |
| 28 | 24.3 | 3.7 | 41.2 |
| 29 | 24.6 | 3.6 | 53.1 |
| 30 | 24.9 | 3.6 | 43.5 |
| 31 | 25.2 | 3.5 | 18.5 |
| 32 | 25.5 | 3.5 | 21.4 |
| 33 | 26.0 | 3.4 | 13.2 |
| 34 | 26.3 | 3.4 | 55.9 |
| 35 | 27.6 | 3.2 | 9.1 |
| 36 | 28.4 | 3.1 | 10.1 |
| 37 | 31.5 | 2.8 | 8.4 |
| 38 | 31.9 | 2.8 | 6.9 |
| 39 | 33.6 | 2.7 | 8.3 |

$^1$H NMR (500 MHZ, CHLOROFORM-d) δ ppm 1.06 (br d, J=6.07 Hz, 6H) 2.77 (s, 3H) 2.85-2.89 (m, 9H) 3.13 (br s, 2H) 3.31 (br t, J=5.56 Hz, 2H) 3.83 (s, 2H) 3.89-3.95 (m, 6H) 5.03 (dt, J=12.45, 6.15 Hz, 1H) 5.78-5.83 (m, 1H) 6.53 (dd, J=16.79, 1.89 Hz, 1H) 6.71 (s, 1H) 6.91-7.05 (m, 3H)

7.16 (t, J=7.56 Hz, 1H) 7.22-7.37 (m, 4H) 7.60 (br s, 1H) 8.49-8.70 (m, 1H) 8.88 (br s, 1H) 9.08 (br s, 1H) 9.73 (br s, 1H) 11.09-11.27 (m, 1H).

Figure 21:
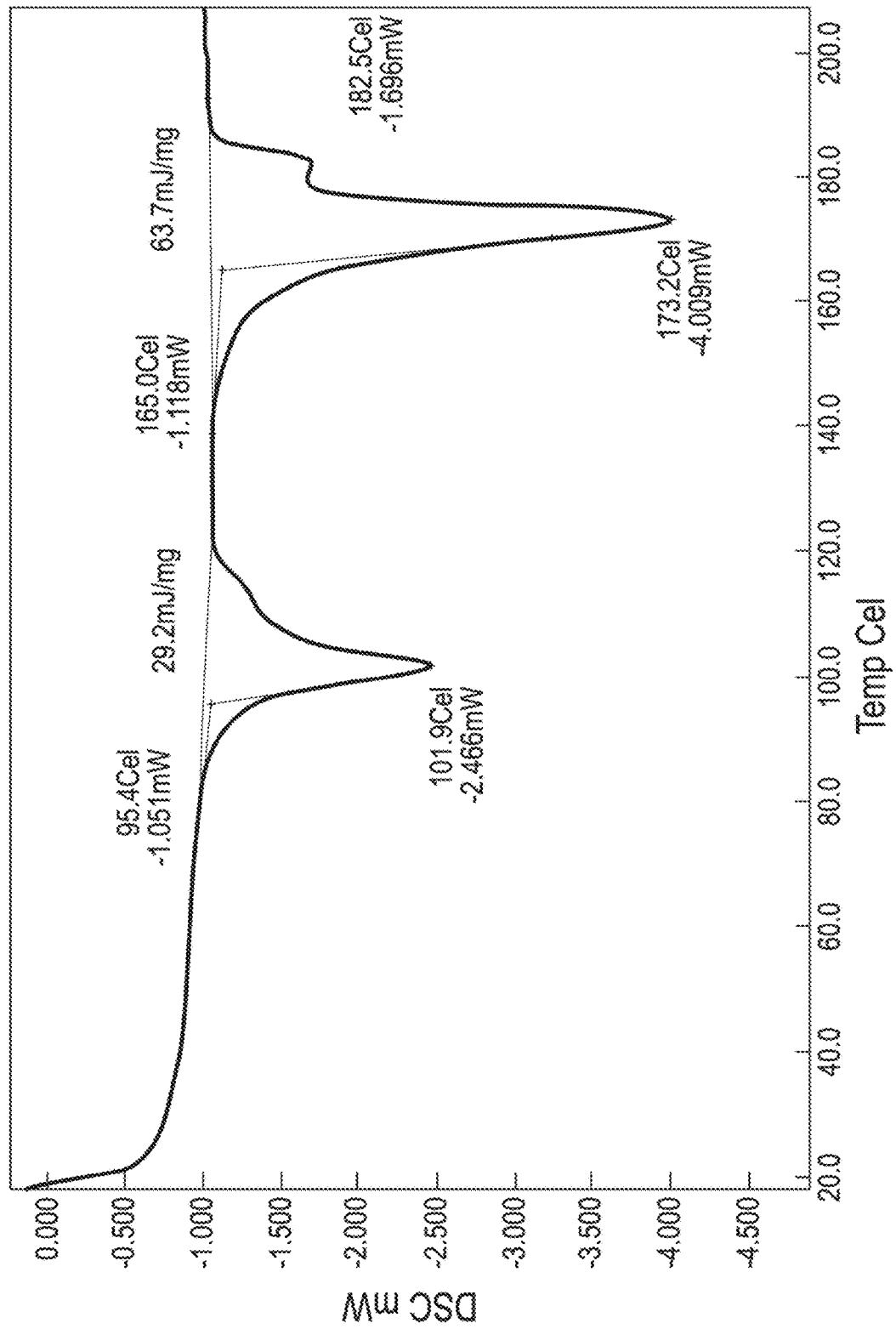
FIG. 21 is a DSC profile for the polymorphic Form-III of the mesylate salt of Compound (A).

DSC profile for polymorphic Form-III of the mesylate salt of Compound (A) is shown in FIG. 21. The profile displays an initial broad endotherm at onset 95.4° C., followed by a larger endotherm at onset 165.0° C.

Figure 22:
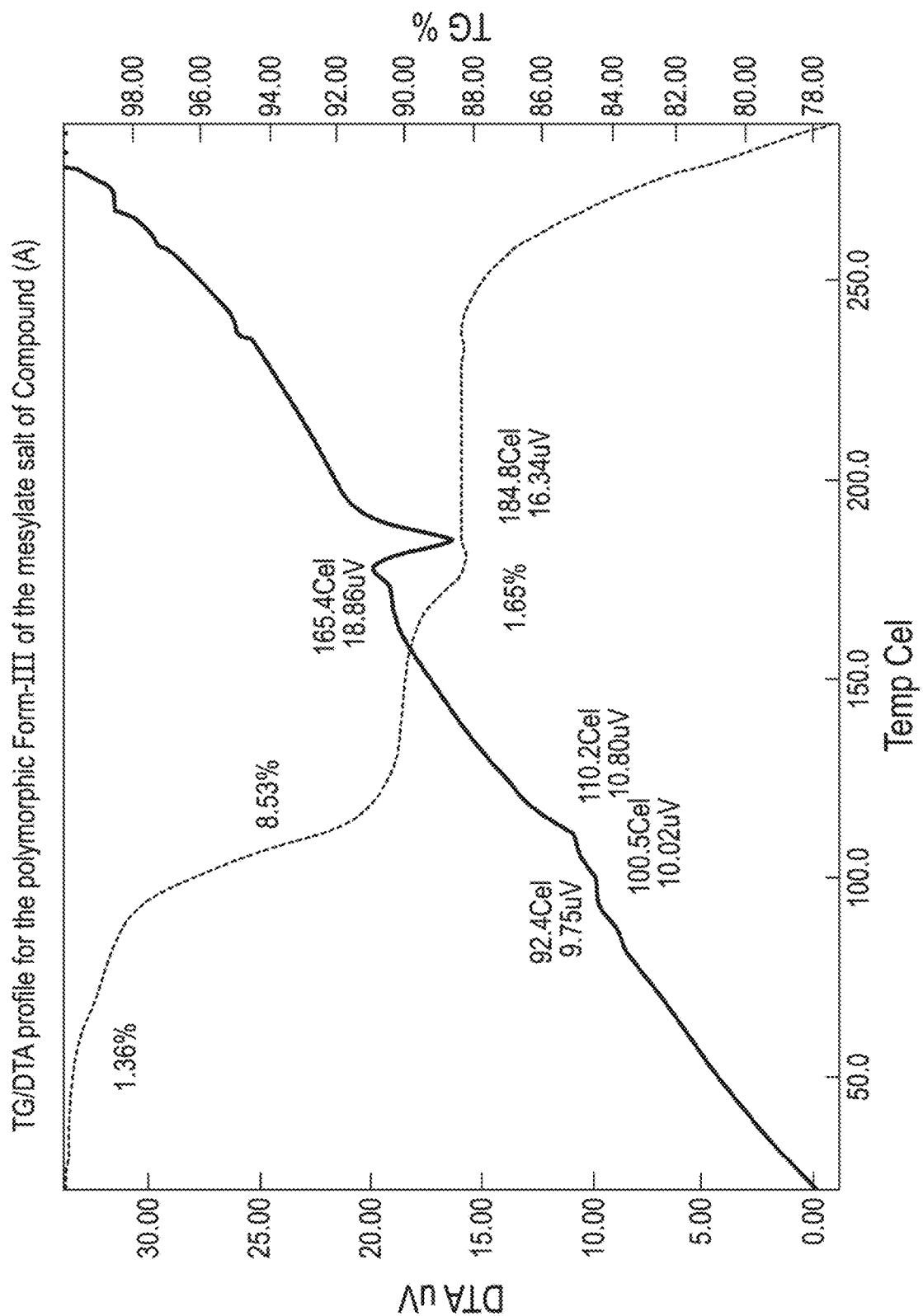
FIG. 22 is a TG/DTA profile for the polymorphic Form-III of the mesylate salt of Compound (A).

TG/DAT profile for polymorphic Form-III of the mesylate salt of Compound (A) is shown in FIG. 22. The profile displays a gradual loss of ca. 1.4% mass from the onset of heating, which is likely due to entrained solvent. A subsequent sharper loss of ca. 8.5% mass was observed, with an associated broad endotherm at onset 92.4° C. It should be noted that 0.5 equivalents of anisole would equate to a mass loss of 7.4%. A small endotherm follows (onset 165.4° C.), followed by a sharper endotherm (minimum at 184.8° C.) with an associated mass loss of ca. 1.65%.

Example 8 Preparation of isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate oxalate (Oxalate Salt of Compound (A))

2-Methyl THF (2.4 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (160.9 mg) to give a mobile slurry. In a separate vial, oxalic acid (25.2 mg, 1.0 eq) was dissolved in 2-methyl THF (0.8 mL) and the resulting solution was added dropwise to the API slurry over 5 minutes. Immediate precipitation of a yellow gummy solid was observed. The mixture was temperature cycled between ambient (ca. 22)° C. and 40° C. in 4 h cycles over 24 h. The resulting solid material was isolated by vacuum filtration and washed with heptane (2 mL). The material was subsequently dried under vacuum at ca. 22° C. in the presence of MgSO4 for 72 h to give isopropyl 2-(5-acrylamido-4-((2-(dimethylamino) ethyl) (methyl)amino)-2-methoxyphenyl)amino)-4-(1-methyl-1H-indol-3-yl)pyrimidine-5-carboxylate oxalate Form-III (146 mg, 79% yield).

Figure 23:
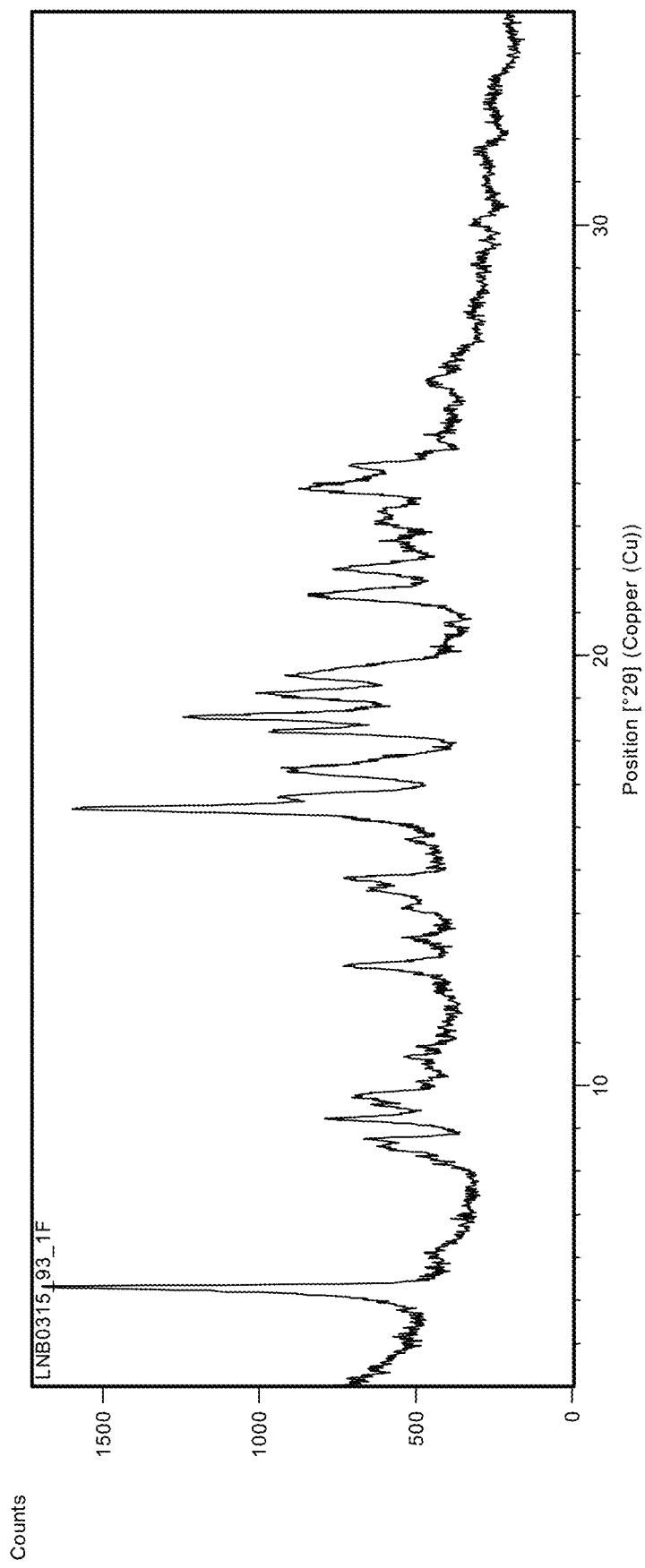
FIG. 23 is XRPD data for the polymorphic Form-III of the oxalate salt of Compound (A).

XRPD data for polymorphic Form-III of the oxalate salt of Compound (A) is shown in FIG. 23 and in Table 13 below.

TABLE 13

| Peak No. | Position [°2θ] | d-spacing [Å] | Rel. Intensity [%] |
|---|---|---|---|
| 1 | 5.3 | 16.6 | 100.0 |
| 2 | 8.2 | 10.8 | 9.7 |
| 3 | 8.3 | 10.6 | 11.5 |
| 4 | 8.6 | 10.3 | 22.4 |
| 5 | 8.7 | 10.1 | 26.8 |
| 6 | 9.2 | 9.6 | 34.5 |
| 7 | 9.5 | 9.3 | 22.0 |
| 8 | 9.7 | 9.1 | 27.5 |
| 9 | 10.1 | 8.8 | 11.2 |
| 10 | 10.4 | 8.5 | 9.1 |
| 11 | 10.7 | 8.3 | 14.5 |
| 12 | 12.8 | 6.9 | 28.5 |
| 13 | 13.4 | 6.6 | 14.1 |
| 14 | 14.1 | 6.3 | 13.9 |
| 15 | 14.6 | 6.1 | 21.8 |
| 16 | 14.8 | 6.0 | 27.7 |
| 17 | 15.7 | 5.6 | 12.1 |
| 18 | 16.4 | 5.4 | 96.5 |
| 19 | 16.7 | 5.3 | 44.8 |
| 20 | 17.3 | 5.1 | 41.5 |
| 21 | 18.2 | 4.9 | 46.8 |
| 22 | 18.6 | 4.8 | 69.0 |

TABLE 13-continued

| Peak No. | Position [°2θ] | d-spacing [Å] | Rel. Intensity [%] |
|---|---|---|---|
| 23 | 19.1 | 4.6 | 48.7 |
| 24 | 19.5 | 4.5 | 41.4 |
| 25 | 21.4 | 4.2 | 36.4 |
| 26 | 22.0 | 4.0 | 32.5 |
| 27 | 22.6 | 3.9 | 16.7 |
| 28 | 23.1 | 3.9 | 21.5 |
| 29 | 23.3 | 3.8 | 22.8 |
| 30 | 23.9 | 3.7 | 41.9 |
| 31 | 24.4 | 3.6 | 30.4 |
| 32 | 26.4 | 3.4 | 12.5 |
| 33 | 30.1 | 3.0 | 5.0 |

$^1$H NMR (500 MHZ, CHLOROFORM-d) δ ppm 0.86-0.96 (m, 4H) 1.05 (br d, J=5.91 Hz, 6H) 1.23-1.36 (m, 7H) 2.25-2.49 (m, 4H) 2.65 (s, 4H) 2.82 (s, 6H) 3.16 (br t, J=5.87 Hz, 2H) 3.31 (t, J=5.95 Hz, 2H) 3.91 (s, 3H) 3.94 (s, 3H) 4.98-5.06 (m, 1H) 5.83 (br d, J=11.03 Hz, 1H) 6.53 (dd, J=16.75, 1.62 Hz, 1H) 6.72 (s, 1H) 6.98-7.09 (m, 1H) 7.16 (t, J=7.52 Hz, 1H) 7.21-7.28 (m, 1H) 7.35 (d, J=8.20 Hz, 1H) 7.91 (s, 1H) 8.91 (s, 1H) 8.99 (br s, 1H) 9.83 (s, 1H).

Figure 24:
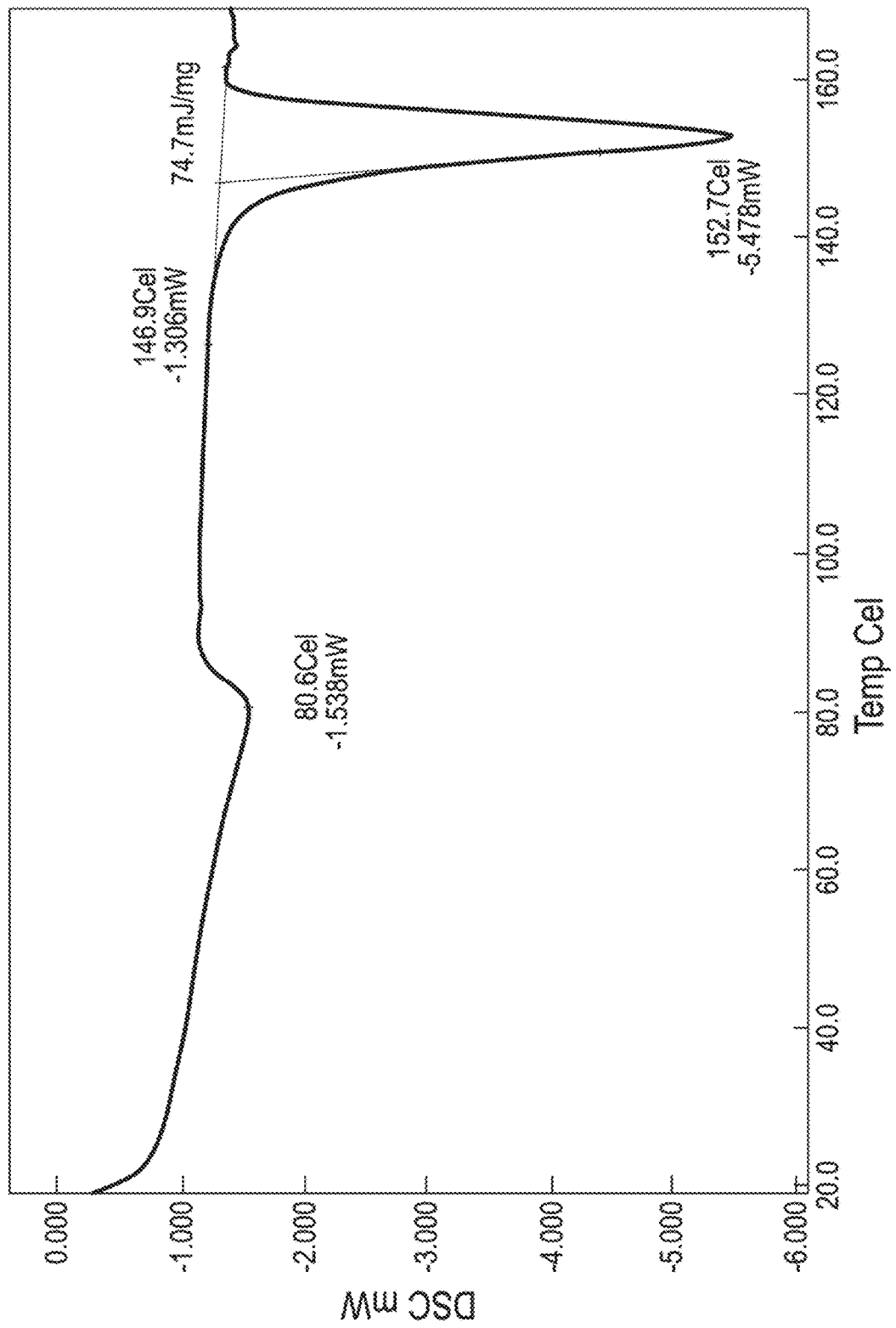
FIG. 24 is a DSC profile for the polymorphic Form-III of the oxalate salt of Compound (A).

DSC profile for polymorphic Form-III of the oxalate salt of Compound (A) is shown in FIG. 24. The profile displays an initial broad endotherm from the onset of heating, with a minimum at 80.6° C. A subsequent large endotherm occurs at onset 146.9° C., with an associated enthalpy of 74.7 mJ/mg. DSC analysis was conducted up to 180° C. to avoid excessive degradation of the sample.

Figure 25:
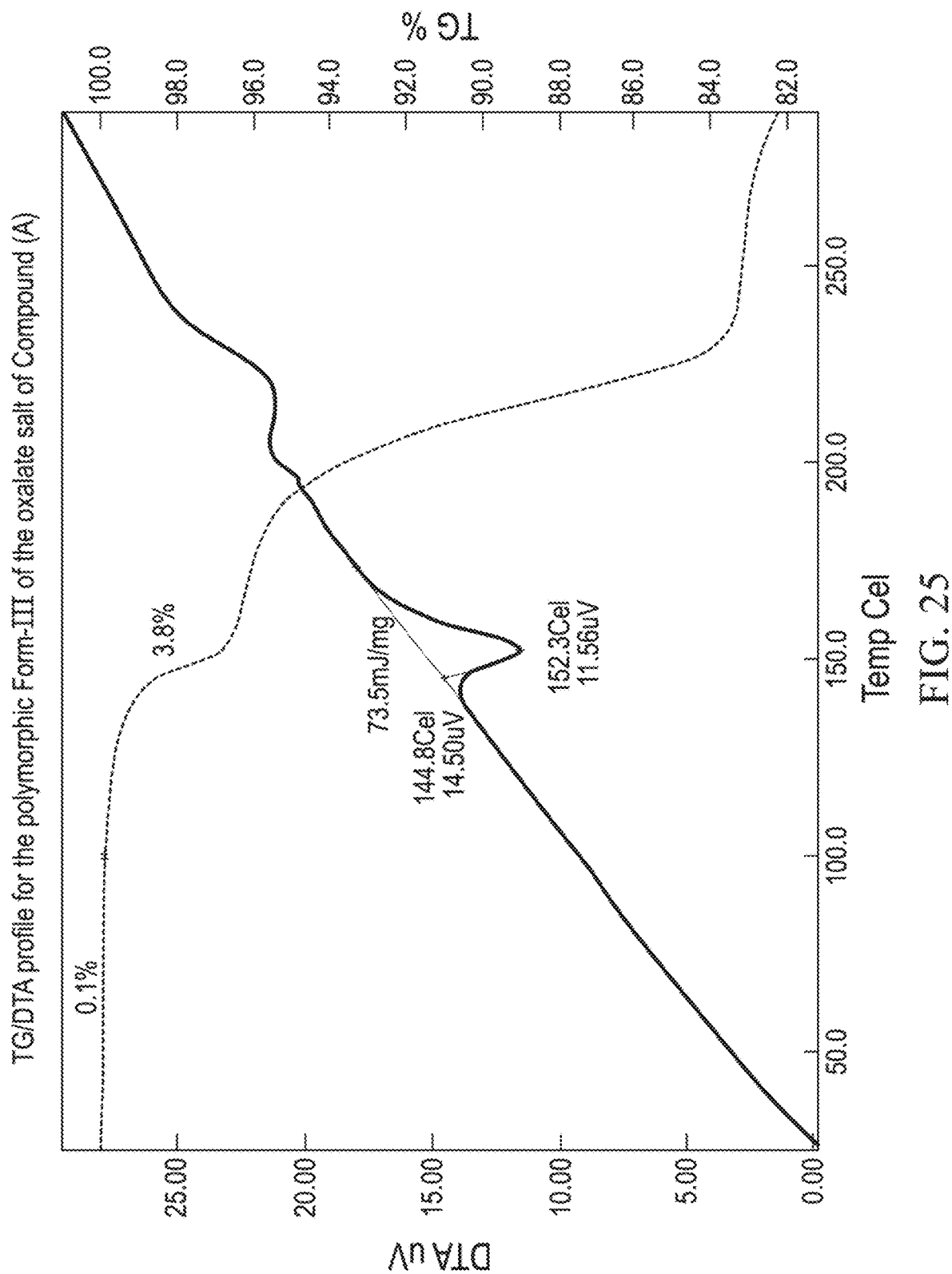
FIG. 25 is a TG/DTA profile for the polymorphic Form-III of the oxalate salt of Compound (A).

TG/DAT profile for polymorphic Form-III of the oxalate salt of Compound (A) is shown in FIG. 25. The profile displays a sharp mass loss of 3.8% observed with an associated large endotherm, occurring at onset 144.8° C., with an associated enthalpy of 73.5 mJ/mg.

Example 9 Preparation of isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate fumarate (Fumarate Salt of Compound (A))

Method 1: 2-Methyl THF (3 mL) was added to isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate (208.0 mg) to give a mobile slurry. In a separate vial, fumaric acid (40.0 mg, 1.0 eq) was added to 2-methyl THF (1.0 mL). The API slurry was added to the fumaric acid slurry over 5 minutes and the resulting mixture was temperature cycled between ambient (ca. 22° C.) and 40° C. in 4 h cycles over 24 h. The resulting solid material was isolated by vacuum filtration, washed with 2-methyl THF (3 mL) and dried under vacuum at ca. 22° C. for 24 h to give isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate fumarate Form-II (233 mg, 94% yield).

Figure 26:
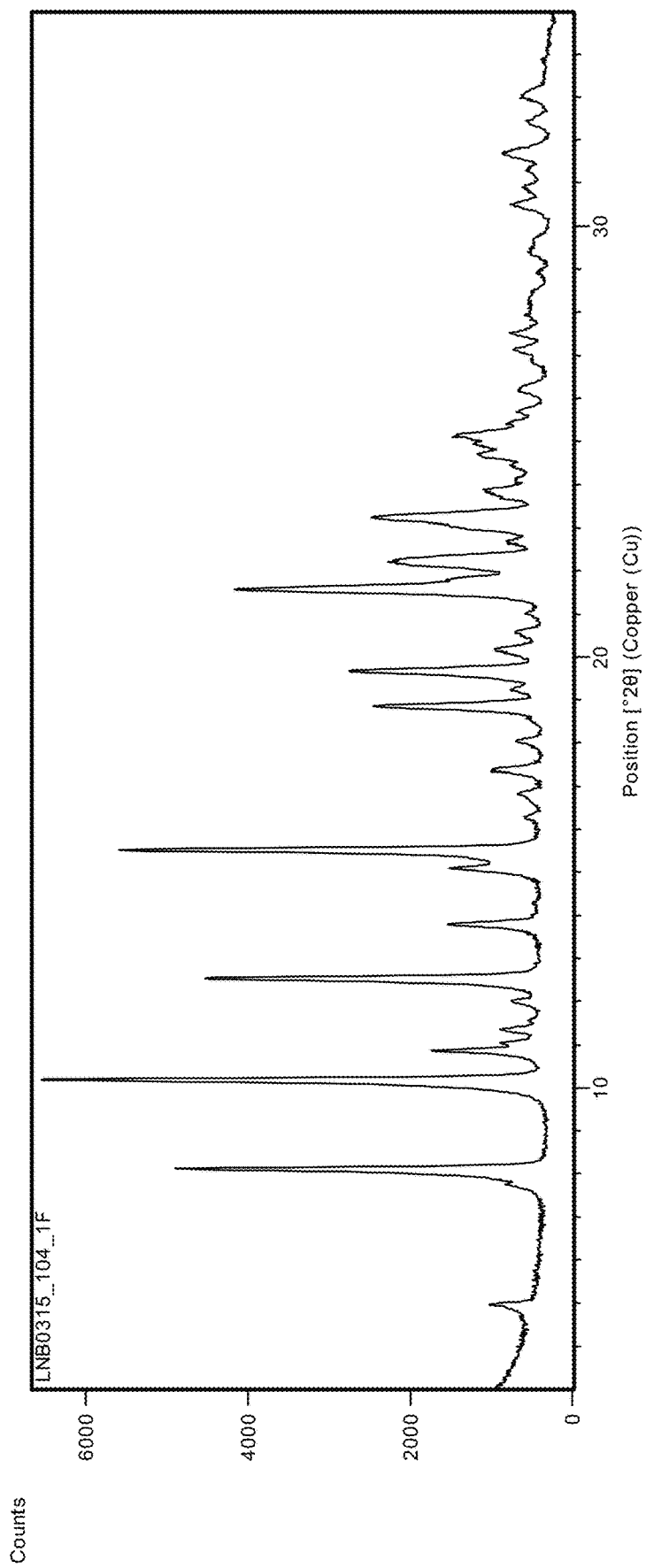
FIG. 26 is XRPD data for the polymorphic Form-II of the fumarate salt of Compound (A).

XRPD data for polymorphic Form-II of the fumarate salt of Compound (A) is shown in FIG. 26 and in Table 14 below. In certain embodiments, polymorphic Form-II of the fumarate salt of Compound (A) has an X-ray powder diffraction pattern expressed, in terms of 2-theta, at approximately 8.1±0.20, 10.2±0.20, 12.5±0.20, 15.5±0.20, and 21.6±0.20 degrees.

In another embodiment, polymorphic Form-II of the fumarate salt of Compound (A) has an X-ray powder diffraction pattern expressed, in terms of 2-theta, at approximately 8.1±0.20, 10.2±0.20, 12.5±0.20, 15.5±0.20, 18.9±0.20, 19.7±0.20, 21.6±0.20, and 15.5±0.20, degrees.

In another embodiment, polymorphic Form-II of the fumarate salt of Compound (A) has an X-ray powder diffraction pattern expressed, in terms of 2-theta, at approximately 8.1 0.20, 10.2±0.20, 10.9±0.20, 12.5±0.20, 13.8±0.20, 15.1±0.20, 15.5±0.20, 18.9±0.20, 19.7±0.20, 21.6±0.20, 22.2±0.20, 23.2±0.20, and 24.7±0.20, degrees.

TABLE 14

| Peak No. | Position [°2θ] | d-spacing [Å] | Rel. Intensity [%] |
|---|---|---|---|
| 1 | 5.0 | 17.8 | 8.2 |
| 2 | 8.1 | 10.9 | 72.9 |
| 3 | 10.2 | 8.7 | 100.0 |
| 4 | 10.9 | 8.1 | 21.9 |
| 5 | 11.0 | 8.0 | 8.4 |
| 6 | 11.4 | 7.8 | 8.3 |
| 7 | 12.0 | 7.4 | 6.0 |
| 8 | 12.5 | 7.1 | 66.6 |
| 9 | 13.8 | 6.4 | 18.1 |
| 10 | 15.1 | 5.9 | 17.8 |
| 11 | 15.5 | 5.7 | 83.5 |
| 12 | 17.4 | 5.1 | 9.2 |
| 13 | 18.9 | 4.7 | 32.4 |
| 14 | 19.2 | 4.6 | 5.3 |
| 15 | 19.7 | 4.5 | 37.4 |
| 16 | 20.2 | 4.4 | 8.6 |
| 17 | 21.6 | 4.1 | 59.4 |
| 18 | 22.2 | 4.0 | 28.7 |
| 19 | 22.7 | 3.9 | 6.4 |
| 20 | 23.2 | 3.8 | 33.0 |
| 21 | 23.9 | 3.7 | 11.1 |
| 22 | 24.7 | 3.6 | 12.5 |
| 23 | 25.1 | 3.5 | 17.2 |
| 24 | 25.7 | 3.5 | 5.1 |
| 25 | 27.1 | 3.3 | 6.1 |
| 26 | 27.5 | 3.2 | 6.8 |
| 27 | 30.5 | 2.9 | 7.3 |
| 28 | 31.7 | 2.8 | 9.4 |
| 29 | 33.0 | 2.7 | 5.9 |

$^1$H NMR (500 MHz, DMSO-d$_6$) δ ppm 1.11-1.16 (m, 6H) 2.44 (s, 6H) 2.65-2.73 (m, 5H) 3.06 (br t, J=5.79 Hz, 2H) 3.81-3.87 (m, 3H) 5.01 (quin, J=6.25 Hz, 1H) 5.74-5.79 (m, 1H) 6.29 (dd, J=16.95, 1.89 Hz, 1H) 6.58-6.67 (m, 3H) 7.02-7.07 (m, 2H) 7.20 (t, J=7.64 Hz, 1H) 7.49 (d, J=8.28 Hz, 1H) 7.76 (br s, 1H) 8.17 (s, 1H) 8.66 (s, 1H) 8.67 (s, 1H) 8.82 (s, 1H) 9.93 (s, 1H).

Figure 27:
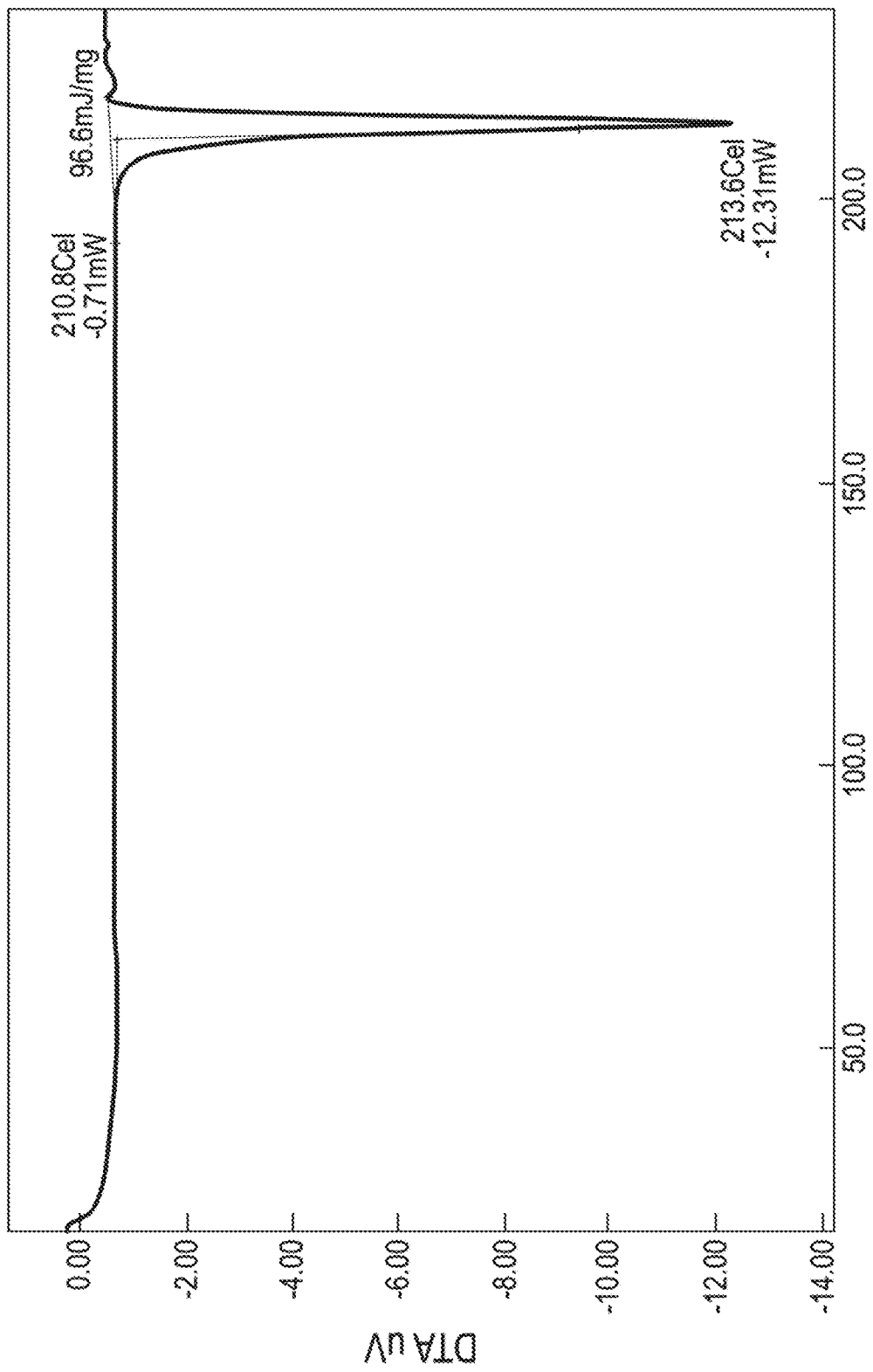
FIG. 27 is a DSC profile for the polymorphic Form-II of the fumarate salt of Compound (A).

DSC profile for polymorphic Form-II of the fumarate salt of Compound (A) is shown in FIG. 27. The profile displays a single large endotherm at onset 210.8° C., with an associated enthalpy of 96.6 mJ/mg. DSC analysis was conducted up to 250° C. to avoid excessive degradation of the sample.

Figure 28:
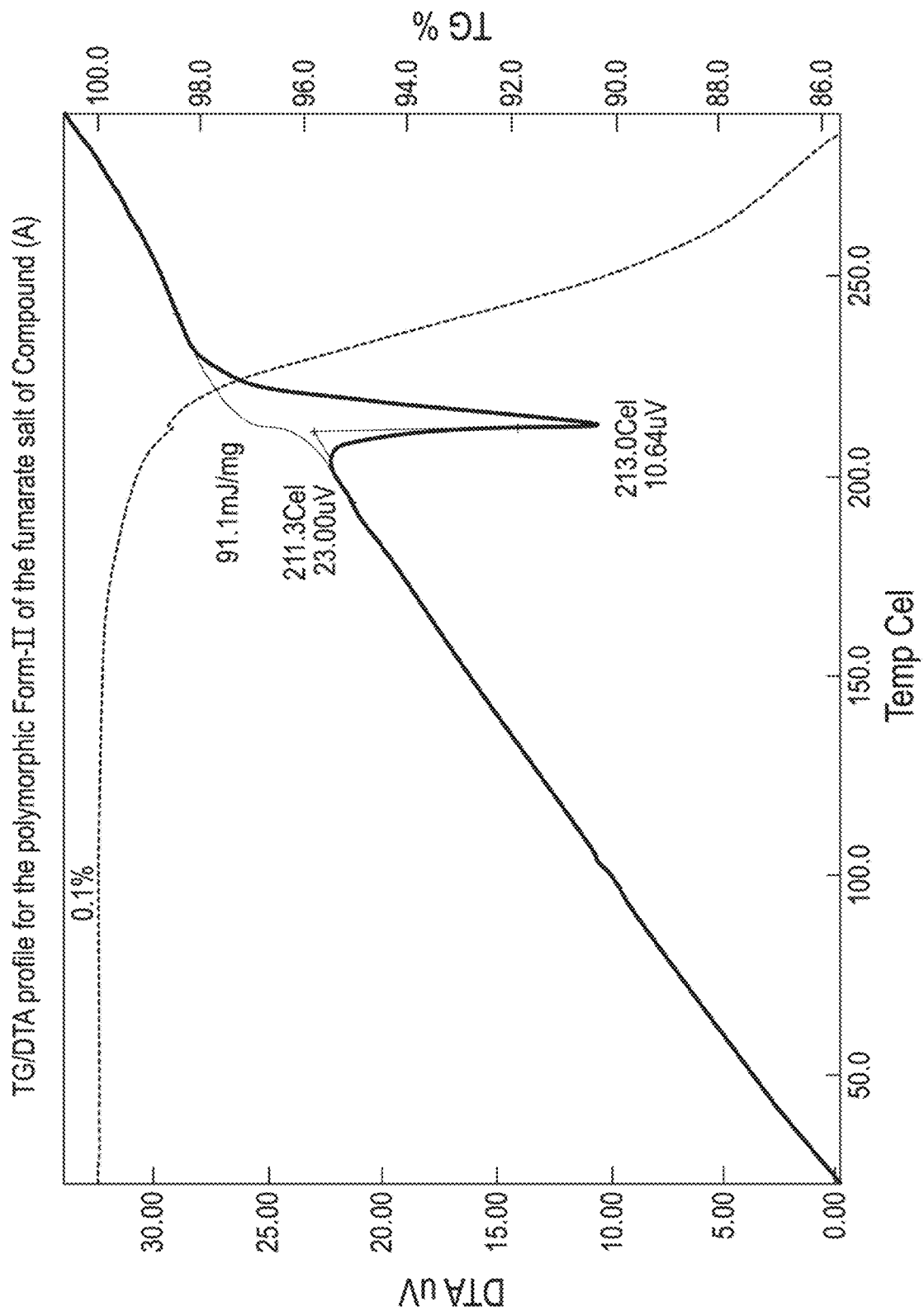
FIG. 28 is a TG/DTA profile for the polymorphic Form-II of the fumarate salt of Compound (A).

TG/DAT profile for polymorphic Form-II of the fumarate salt of Compound (A) is shown in FIG. 28. The profile displays no signs of mass loss noted until the onset of degradation above 200° C. A single sharp endotherm occurs at onset 211.3° C. with an associated enthalpy of 91.1 mJ/mg.

Method 2: Anisole was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate to give a mobile slurry. In a separate vial, fumaric acid was added to anisole. The API slurry was added to the fumaric acid solution over 5 minutes and the resulting mixture was temperature cycled between ambient (ca. 22° C.) and 40° C. in 4 h cycles over 24 h. The resulting solid material was isolated by vacuum filtration, washed with anisole and dried under vacuum to give isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate fumarate Form-I (233 mg, 94% yield).

Figure 29:
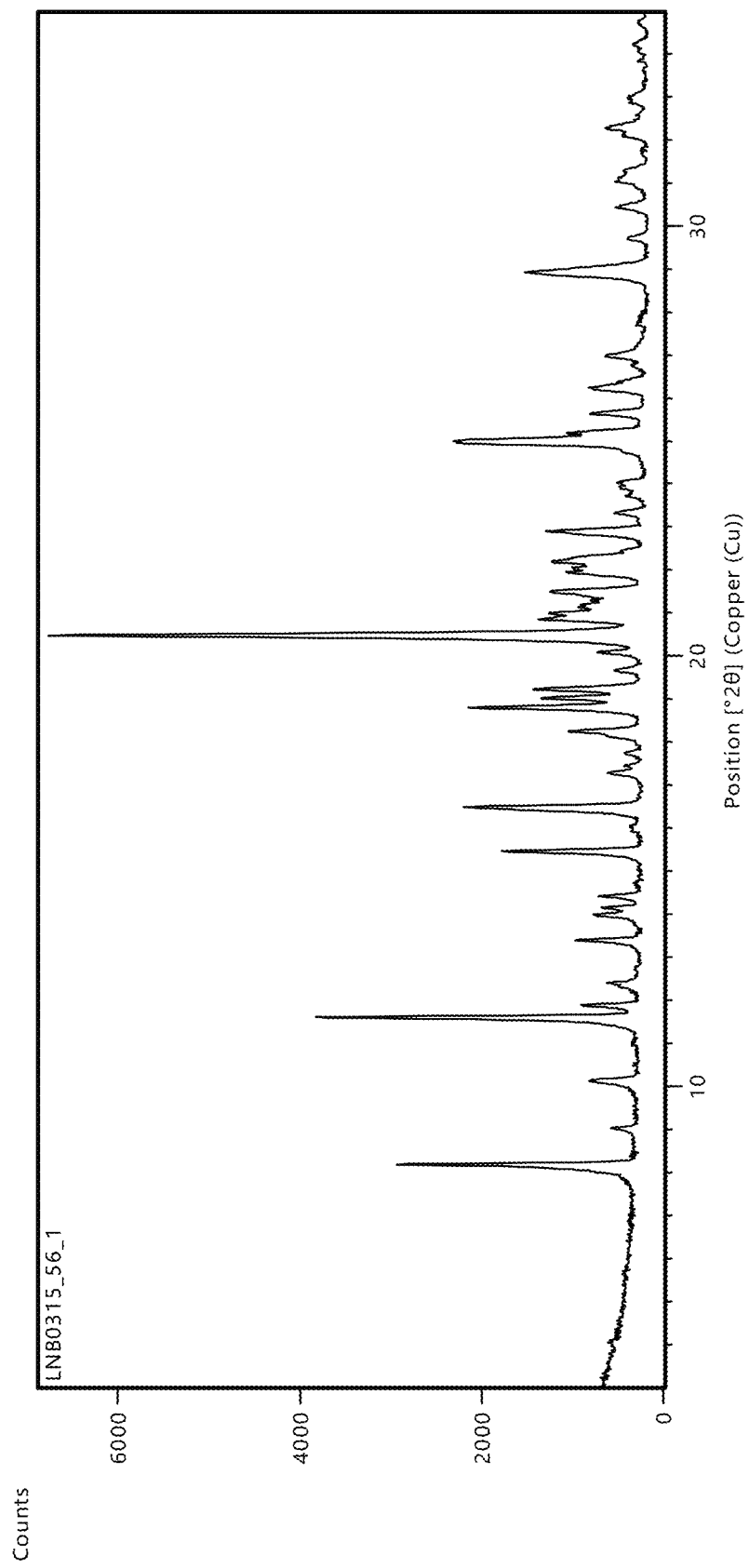
FIG. 29 is XRPD data for the polymorphic Form-I of the fumarate salt of Compound (A).

XRPD data for polymorphic Form-II of the fumarate salt of Compound (A) is shown in FIG. 29 and in Table 15 below.

TABLE 15

| Peak No. | Position [°2θ] | d-spacing [Å] | Rel. Intensity [%] |
|---|---|---|---|
| 1 | 8.2 | 10.8 | 39.6 |
| 2 | 10.2 | 8.7 | 7.4 |
| 3 | 11.6 | 7.6 | 54.2 |
| 4 | 11.9 | 7.4 | 9.5 |
| 5 | 12.4 | 7.1 | 5.2 |
| 6 | 13.4 | 6.6 | 10.6 |
| 7 | 14.0 | 6.3 | 7.8 |
| 8 | 14.2 | 6.3 | 6.0 |
| 9 | 14.4 | 6.1 | 6.8 |
| 10 | 15.5 | 5.7 | 22.9 |
| 11 | 16.4 | 5.4 | 19.2 |
| 12 | 16.5 | 5.4 | 28.6 |
| 13 | 18.2 | 4.9 | 12.2 |
| 14 | 18.8 | 4.7 | 28.5 |
| 15 | 19.0 | 4.7 | 17.0 |
| 16 | 19.2 | 4.6 | 18.4 |
| 17 | 20.1 | 4.4 | 7.5 |
| 18 | 20.5 | 4.3 | 100.0 |
| 19 | 20.9 | 4.3 | 17.4 |
| 20 | 21.0 | 4.2 | 15.6 |
| 21 | 21.1 | 4.2 | 8.2 |
| 22 | 21.5 | 4.1 | 15.0 |
| 23 | 21.9 | 4.1 | 12.3 |
| 24 | 22.0 | 4.0 | 10.1 |
| 25 | 22.2 | 4.0 | 15.3 |
| 26 | 22.3 | 4.0 | 9.6 |
| 27 | 22.9 | 3.9 | 16.3 |
| 28 | 23.3 | 3.8 | 5.0 |
| 29 | 24.9 | 3.6. | 29.2 |
| 30 | 25.0 | 3.6 | 30.76 |
| 31 | 25.2 | 3.5 | 12.79 |
| 32 | 25.6 | 3.5 | 9.41 |
| 33 | 26.2 | 3.4 | 9.16 |
| 34 | 27.0 | 3.3 | 6.75 |
| 35 | 28.8 | 3.1 | 14.18 |
| 36 | 28.9 | 3.1 | 20.4 |
| 37 | 30.4 | 2.9 | 5.28 |
| 38 | 32.3 | 2.8 | 6.76 |

Example 10 Preparation of isopropyl 2-((5-acrylamido-4-((2-(dimethylamino)ethyl) (methyl) amino)-2-methoxyphenyl)amino)-4-(1-methyl-1H-indol-3-yl)pyrimidine-5-carboxylate hippurate (the Hippurate Salt of Compound (A))

2-Methyl THF (3 mL) was added to isopropyl 2-((5-acrylamido-4-((2-(dimethylamino)ethyl) (methyl)amino)-2-methoxyphenyl)amino)-4-(1-methyl-1H-indol-3-yl)pyrimidine-5-carboxylate (210.4 mg) to give a mobile slurry. In a separate vial, hippuric acid (66.6 mg, 1.07 eq) was added to 2-methyl THF (1.0 mL). The API slurry was added to the hippuric acid slurry over 5 minutes and the resulting mixture was temperature cycled between ambient (ca. 22)° C. and 40° C. in 4 h cycles over 24 h. The resulting solid material was isolated by vacuum filtration, washed with 2-methyl THF (3 mL) and dried under vacuum at ca. 22° C. for 4 days to give isopropyl 2-((5-acrylamido-4-((2-(dimethylamino) ethyl) (methyl)amino)-2-methoxyphenyl)amino)-4-(1-methyl-1H-indol-3-yl)pyrimidine-5-carboxylate hippurate Form-I (196 mg, 71% yield).

Figure 30:
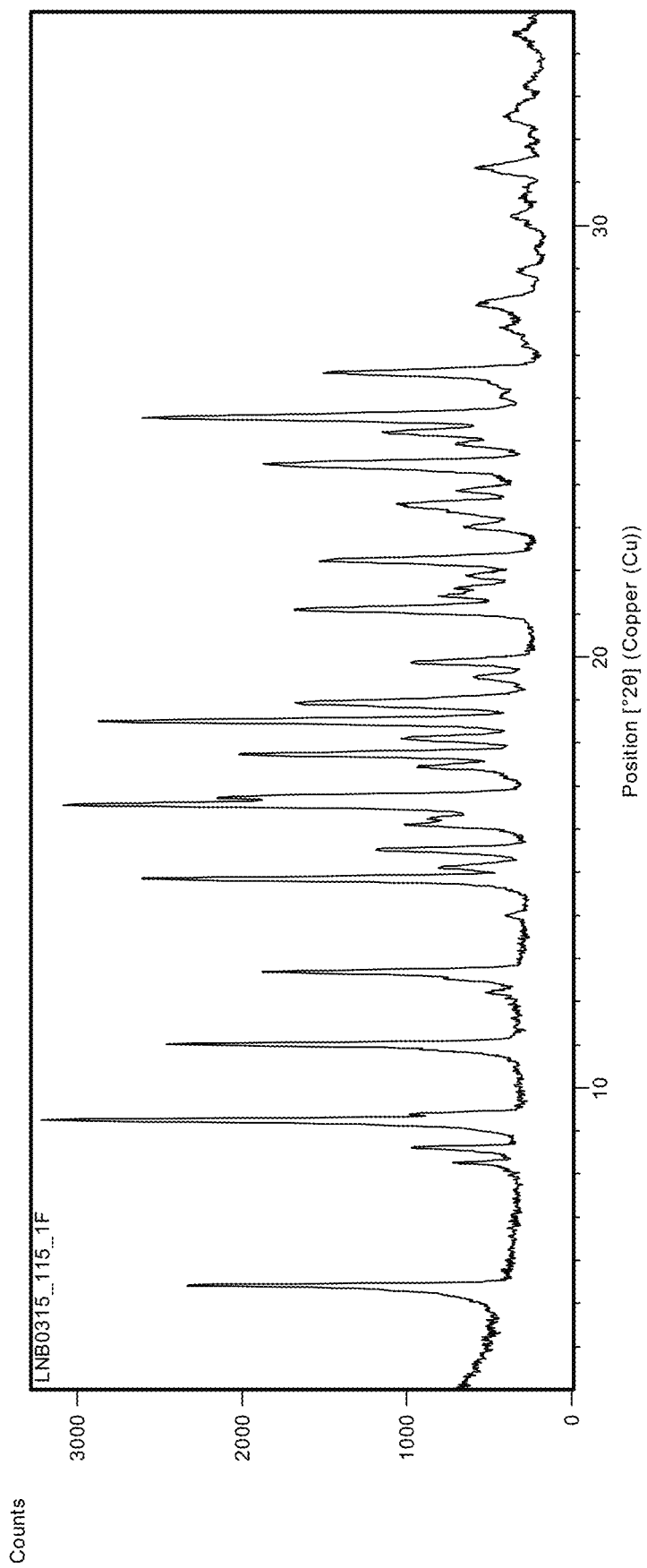
FIG. 30 is XRPD data for the polymorphic Form-I of the hippurate salt of Compound (A).

XRPD data for polymorphic Form-I of the hippurate salt of Compound (A) is shown in FIG. 30 and in Table 16 below.

TABLE 16

| Peak No. | Position [°2θ] | d-spacing [Å] | Rel. Intensity [%] |
|---|---|---|---|
| 1 | 5.4 | 16.3 | 66.0 |
| 2 | 8.3 | 10.7 | 13.4 |
| 3 | 8.6 | 10.3 | 22.4 |
| 4 | 9.3 | 9.6 | 100.0 |
| 5 | 9.4 | 9.4 | 23.1 |
| 6 | 11.0 | 8.0 | 73.5 |
| 7 | 12.2 | 7.2 | 7.2 |
| 8 | 12.7 | 7.0 | 54.3 |
| 9 | 14.9 | 6.0 | 79.5 |
| 10 | 15.1 | 5.9 | 18.0 |
| 11 | 15.5 | 5.7 | 31.2 |
| 12 | 16.1 | 5.5 | 24.4 |
| 13 | 16.6 | 5.4 | 96.1 |
| 14 | 16.7 | 5.3 | 64.0 |
| 15 | 17.5 | 5.1 | 23.0 |
| 16 | 17.7 | 5.0 | 59.9 |
| 17 | 18.1 | 4.9 | 25.9 |
| 18 | 18.5 | 4.8 | 89.5 |
| 19 | 18.9 | 4.7 | 47.7 |
| 20 | 19.5 | 4.5 | 12.0 |
| 21 | 19.9 | 4.5 | 25.2 |
| 22 | 21.1 | 4.2 | 49.6 |
| 23 | 21.4 | 4.1 | 18.8 |
| 24 | 21.9 | 4.1 | 13.7 |
| 25 | 22.2 | 4.0 | 43.1 |
| 26 | 23.0 | 3.9 | 14.0 |
| 27 | 23.5 | 3.8 | 27.8 |
| 28 | 23.9 | 3.7 | 16.1 |
| 29 | 24.5 | 3.6 | 56.5 |
| 30 | 24.9 | 3.6 | 16.5 |
| 31 | 25.2 | 3.5 | 30.9 |
| 32 | 25.5 | 3.5 | 81.5 |
| 33 | 26.0 | 3.4 | 7.7 |
| 34 | 26.6 | 3.4 | 44.2 |
| 35 | 27.7 | 3.2 | 6.4 |
| 36 | 28.2 | 3.2 | 12.4 |
| 37 | 30.2 | 3.0 | 6.3 |
| 38 | 31.3 | 2.9 | 13.3 |
| 39 | 32.5 | 2.8 | 7.3 |
| 40 | 32.8 | 2.7 | 5.2 |
| 41 | 34.4 | 2.6 | 5.3 |

$^1$H NMR (500 MHZ, DMSO-d$_6$) δ ppm 1.13 (d, J=6.31 Hz, 6H) 2.30 (s, 6H) 2.43-2.50 (m, 2H) 2.69-2.73 (m, 3H) 2.96 (t, J=5.75 Hz, 2H) 3.73 (s, 1H) 3.87-3.93 (m, 5H) 5.01 (quin, J=6.27 Hz, 1H) 5.75-5.80 (m, 1H) 6.29 (dd, J=16.98, 1.93 Hz, 1H) 6.50 (dd, J=16.91, 10.13 Hz, 1H) 7.02-7.08 (m, 2H) 7.20 (t, J=7.73 Hz, 1H) 7.47-7.57 (m, 4H) 7.75 (br s, 1H) 7.88 (d, J=7.42 Hz, 2H) 8.18 (s, 1H) 8.65 (s, 1H) 8.67 (s, 1H) 8.76 (t, J=5.79 Hz, 1H) 8.83 (s, 1H) 10.07 (s, 1H).

Figure 31:
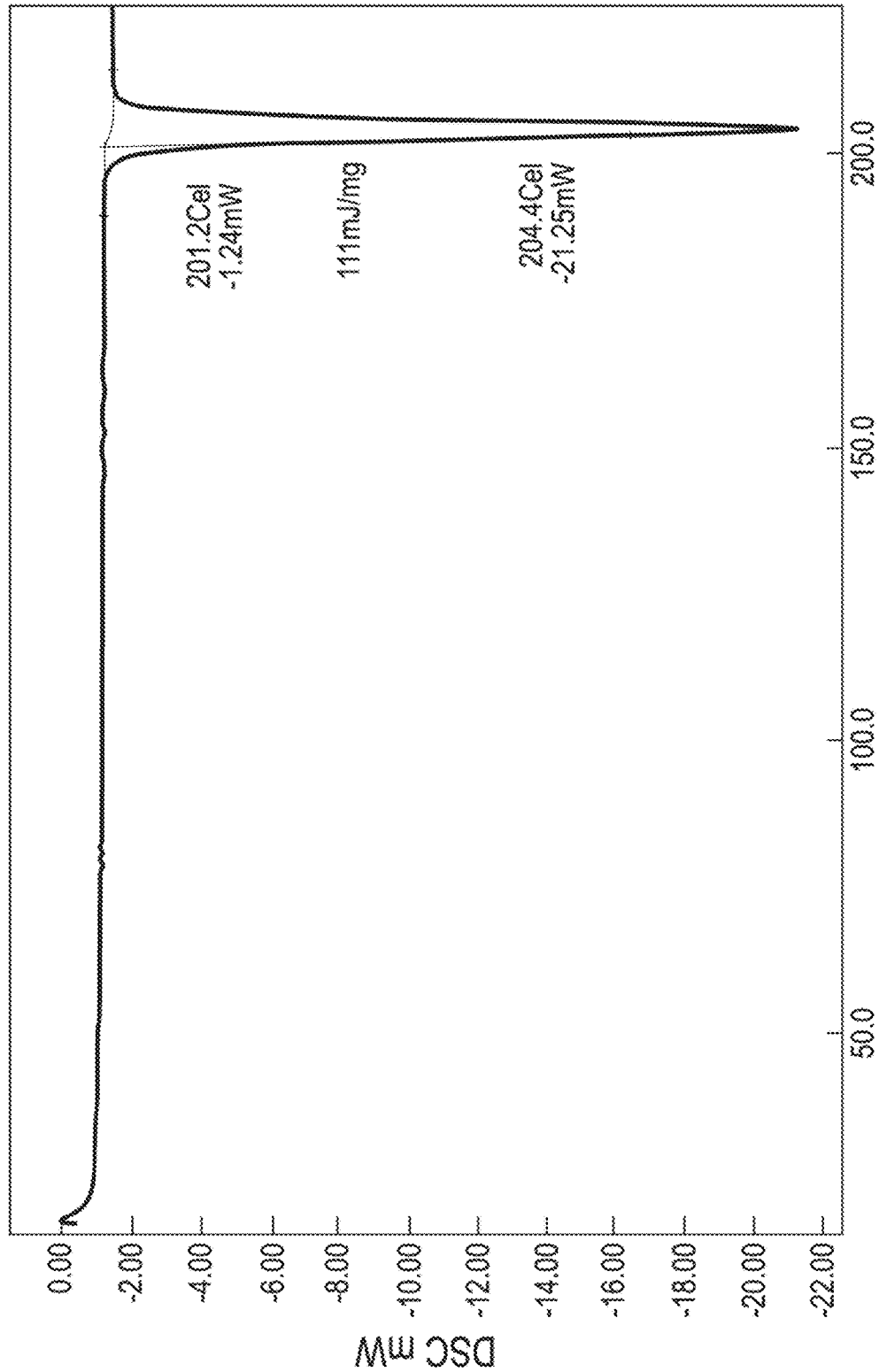
FIG. 31 is a DSC profile for the polymorphic Form-I of the hippurate salt of Compound (A).

DSC profile for polymorphic Form-I of the hippurate salt of Compound (A) is shown in FIG. 31. The profile displays a single large endotherm at onset 201.2° C., with an associated enthalpy of 111 mJ/mg. DSC analysis was conducted up to 240° C. to avoid excessive degradation of the sample.

Figure 32:
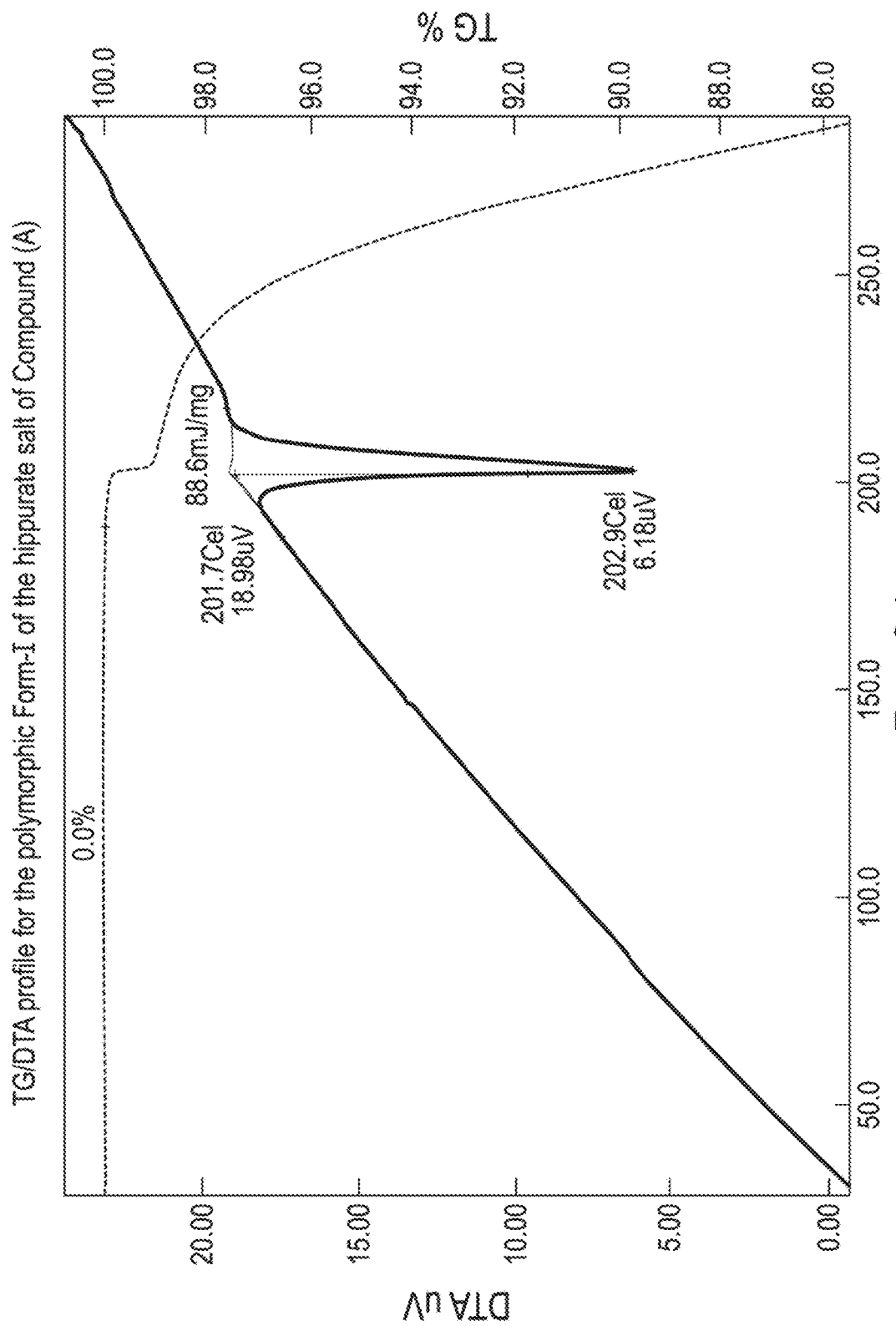
FIG. 32 is a TG/DTA profile for the polymorphic Form-I of the hippurate salt of Compound (A).

TG/DAT profile for polymorphic Form-I of the hippurate salt of Compound (A) is shown in FIG. 32. The profile displays no signs of mass loss noted until the onset of degradation at ca. 200° C. A single sharp endotherm occurs at onset 201.7° C. with an associated enthalpy of 88.6 mJ/mg.

Example 11 Property Analysis for the Samples

1. Vapour Sorption Analysis (GVS, Hygroscopicity)

Approximately 10 mg of the sample was placed into a mesh vapor sorption balance pan and loaded into an IGAS-orp Moisture Sorption Analyzer balance by Hiden Analytical. The sample was subjected to a ramping profile from 40 to 90% relative humidity (RH) at 10% increments to 90% RH, maintaining the sample at each step until a stable weight had been achieved (98% step completion). After completion of the sorption cycle, the sample was dried using the same procedure (initially from 90% RH to 0% RH and finally taken back to the starting point of 40% RH). The sorption/desorption profiles were then repeated to give a double-cycle plot. The weight changes during the sorption/desorption cycles were plotted, allowing for the hygroscopic nature of the sample to be determined. Table 17 shows certain properties of several salts of Compound (A) and the free base of Compound (A).

TABLE 17

| Salts | XRPD Form | DSC (Melting) | GVS* (Hygroscopicity) | Chemical Stability |
|---|---|---|---|---|
| Sulfate | I | 197.6° C. | 11% | Degradation |
| Mesylate | III | 165.0° C. | Drying Form conversion | Stable |
| Oxalate | III | 146.9° C. | 2.0% | Stable |
| HCl | I | 185.9° C. | 10.% | Degradation |
| Succinate | I | 177.5° C. | 1.3% | Stable |
| Tosylate | I | 166.8° C. | 1.4% | Stable |
| Hippurate | I | 201.7° C. | 0.2% | Stable |
| HBr | I | 236.0° C. | 0.6% | Stable |
| Fumarate | II | 210.8° C. | 2.0% | Stable |
| Free Base | I | 182.5° C. | 0.3% | Stable |

*GVS percentage refers to the % uptake at 90% RH.

2. Stability Stress Testing

Approximately 5 mg of the appropriate samples were placed into 2 mL clear glass vials and the vials were all stored open under the conditions of ambient light, 40° C./75% RH, and 80° C. for 7 days, respectively. The ambient light sample was left open on the bench at room temperature. The 80° C. sample was placed open into an 80° C. oven. The samples were analyzed by XRPD and HPLC for purity under each stress condition as shown in Table 18.

TABLE 18

| Salts | XRPD Form | Input purity | Ambient light | 40° C./75% RH | 80° C. | XRPD |
|---|---|---|---|---|---|---|
| Sulfate | I | 98.3 | 98.6 | 96.2 | 94.9 | No change at ambient light; small changes observed in other 2 conditions |
| Mesylate | III | 99.7 | 99.6 | 99.6 | 99.6 | No change at ambient light; Converted to Form IV at 40° C./75% RH and 80° C. |
| Oxalate | III | 99.7 | 99.6 | 99.6 | 99.6 | No change at ambient light; minor changes observed in other 2 conditions |
| HCl | I | 99.0 | 95.1 | 74.5 | 91.3 | No change at ambient light; changes observed in other 2 conditions |

TABLE 18-continued

| Salts | XRPD Form | Input purity | Ambient light | 40° C./ 75% RH | 80° C. | XRPD |
|---|---|---|---|---|---|---|
| Succinate | I | 99.7 | 99.6 | 99.6 | 99.6 | No change under all storage conditions |
| Tosylate | I | 99.7 | 99.5 | 99.4 | 99.4 | No change under all storage conditions |
| Hippurate | I | 99.7 | 99.6 | 99.6 | 99.6 | No change under all storage conditions |
| HBr | I | 99.7 | 99.6 | 99.6 | 99.5 | No change under all storage conditions |
| Fumarate | II | 99.7 | 99.5 | 99.5 | 99.5 | No change under all storage conditions |
| Free Base | I | 99.7 | 99.5 | 99.5 | 99.5 | No change under all storage conditions |

3. Thermodynamic Aqueous Solubility Studies

De-ionized water (500 μL, pH 6.97) was added to ca. 30 mg of the appropriate samples and the slurry was shaken at ambient temperature for 24 h. The resulting solid material was isolated by centrifugation and analyzed by XRPD, while the filtrate was analyzed by HPLC for concentration determination. The pH of the resulting filtrate was also determined.

Table 19 provides solubility of Compound (A) in the forms of salts and free base, respectively.

TABLE 19

| Salts | Solubility in Water (mg/ml) | pH at Saturation |
|---|---|---|
| Sulfate | >240 | 2.19 |
| Mesylate | >70 | 2.90 |
| Oxalate | 6.8 | 3.00 |
| HCl | 5.8 | 6.47 |
| Succinate | 1.9 | 5.00 |
| Tosylate | 0.4 | 6.38 |
| Hippurate | 0.1 | 5.61 |
| HBr | 0.1 | 6.30 |
| Fumarate | 0.1 | 3.98 |
| Free Base | <<10 μg/mL | 7.81 |

Example 12 Phase ½ First Results

Compound (A) is an investigational tyrosine kinase inhibitor with potent, selective preclinical activity against activating EGFR and HER2 mutations, including exon 20 insertions. A phase ½ first-in-human, open-label, multi-center study of Compound (A) was conducted and first results were obtained. Patients with advanced NSCLC refractory to standard therapy received daily oral doses (5-120 mg) of Compound (A) in the dose-escalation phase. Compound (A) was provided as polymorphic Form-I of the succinate salt of Compound (A). Compound (A) was formulated as a drug-in-capsule with no excipients and administered orally. Preliminary antitumor activity (by RECIST v1.1), safety and pharmacokinetics are reported for patients receiving at least one dose.

Results: During the initial period, 34 patients (median age, 60 y; female, 65%; ≥2 prior anticancer therapies, 88%; see Table 20) were treated and 10 remained on Compound (A) at data cutoff. $AUC_{0-24,ss}$ increased in a dose-proportional manner over the dose range with effective $t_{1/2}$ of ~16 (range 6-26) h. The most common treatment-emergent adverse events (TEAEs; ≥20% of patients) were diarrhea (47%), nausea (26%), and fatigue (21%). Grade≥3 TEAEs in ≥2 patients (excluding disease progression): dyspnea pneumonitis (n=2 each, 6%). Two dose limiting toxicities, both pneumonitis, were reported (80 mg, grade 3; 120 mg, grade 5). Of 14 evaluable patients, 3 had partial response (PR) (80 mg, n=2, both confirmed; 120 mg single PR awaiting confirmation), 6 had stable disease (SD) (40 mg, n=3; 80 mg, n=2; 120 mg, n=1), and 5 had progressive disease (PD) as best response (40 mg, n=3; 80 mg, n=1; 120 mg, n=1). All patients with PR or SD had EGFR exon 20 insertions.

TABLE 20

| | Baseline characteristics | | | | | | |
|---|---|---|---|---|---|---|---|
| | 5 mg (n = 4) | 10 mg (n = 5) | 20 mg (n = 5) | 40 mg (n = 6) | 80 mg (n = 7) | 120 mg (n = 7) | Total (n = 34) |
| Mutation type,[a] % | | | | | | | |
| Common EGFR mutations (exon 19 deletion/L8585R) | 25 | 20 | 0 | 0 | 0 | 0 | 6 |
| EGFR-T790M + | 0 | 0 | 0 | 0 | 14 | 0 | 3 |
| EGFR exon 20 insertion | 50 | 40 | 60 | 83 | 71 | 57 | 62 |
| HER2 | 0 | 20 | 40 | 17 | 14 | 29 | 21 |

[a] One pt (20 mg) had both EGFR and HER2 mutations; 1 pt (80 mg) had EGFR exon 20 insertion + T790M.

Example 13: Phase ½ Study/Dose Escalation Study

As part of the same phase ½ study as described in Example 12, a dose escalation study was performed. 52 patients were enrolled as of 30 Jan. 2018. The following numbers of patients were treated at each of the 7 dose levels evaluated in the dose escalation: 5 mg QD (n=4), 10 mg QD (n=5), 20 mg QD (n=5), 40 mg QD (n=6), 80 mg QD (n=7), 120 mg QD (n=11), 160 mg QD (n=6), 180 mg QD (n=4) and 40 mg BID (n=4). 160 mg (QD) was identified as the maximum tolerated dose (MTD). Based on the efficacy, safety, and PK data, 160 mg QD was tentatively identified as the recommended phase 2 dose (RP2D) pending further evaluation of multicycle safety/tolerability and clinical activity at 160 mg and 120 mg QD doses in the ongoing expansion phase to inform final selection of the RP2D. The rationale for selecting 160 mg QD was based on the following considerations: (1) EGFR exon 20 insertions include heterogeneous variants in EGFR exon 20 region, and 160 mg QD will likely achieve sufficient exposure to inhibit most of the EGFR exon 20 insertion mutations, if not all; and (2) with likely higher CNS exposure, the 160 mg QD dose may also exhibit activity against brain metastases. In order to optimize systemic activity and control CNS disease, there is a strong rationale to use the highest safe dose of Compound (A).

Expansion Phase

The dose escalation phase was continued to an expansion phase. At the data cut date 38.4% of patients (20 of 52) remained on study treatment. The primary reasons for discontinuation are documented progressive disease (PD) per RECIST version 1.1 (26.9%) and adverse event (AE) (15.4%).

Among 52 patients, 46 (88.5%) patients experienced at least one TEAE; 41 (78.8%) patients experienced at least 1 treatment-related adverse event (TRAE); 20 (38.5%) patients experienced at least 1 treatment-emergent serious adverse event (SAE); and 5 (9.6%) patients experienced at least 1 treatment-related SAE. Grade 3 TEAEs occurred in 51.9% (27 of 52) of patients overall.

Disease stabilization started to be reported at the 40 mg QD cohort. Disease assessments for patients who had at least one disease assessment following treatment with Compound (A) are shown in Table 21. All patients who responded have EGFR exon 20 insertion mutations and had previously been treated with platinum-based chemotherapy, EGFR TKIs, or PD-1 inhibitors.

TABLE 21

Disease assessments

| Cohort | SD | PR | CR |
|---|---|---|---|
| 40 mg QD | 3 patients | — | — |
| 80 mg QD | 2 patients | 2 patients | — |
| 120 mg QD | 2 patients | — | 1 patient |
| 160 mg QD | 1 patient | 2 patients [a] | — |

Abbrevitions: CR, compite response; PR, partial response; QD, once daily; SD, stable disease.
[a] unconfirmed.

In the 40 mg QD cohort, 3 patients were reported to have stable disease (SD). In the 80 mg QD and above cohort, a total of 5 patients were reported to have an objective response (2 confirmed partial response [PR] at 80 mg QD, 1 confirmed complete response at 120 mg QD, and 2 PR awaiting confirmation at 160 mg QD at the time of data cutoff), and 6 additional patients had SD including 1 at 180 mg QD.

Example 14: Expansion and Extension Phases

A total of 101 patients in the trial have been exposed to the succinate salt of Compound (A). All patients in the trial are previously treated and received at least 1 prior systemic anticancer regimen. A total of 99 (98.0%) patients experienced at least 1 treatment-emergent adverse event (TEAE), 59 (58.4%) experienced at least 1 Grade≥3 TEAE, 92 (91.1%) experienced at least 1 treatment-related adverse event (TRAE), 30 (29.7%) experienced at least 1 Grade≥3 TRAE, 36 (35.6%) experienced at least 1 treatment-emergent serious adverse event (SAE), 11 (10.9%) experienced at least 1 treatment-related SAE, and 19 (18.8%) experienced any TEAE leading to treatment discontinuation. Of the 46 patients treated at 160 mg QD dose (escalation and expansion cohorts 1-4), 45 (97.8%) experienced at least 1 TEAE, 26 (56.5%) experienced at least 1 Grade≥3 TEAE, 43 (93.5%) experienced at least 1 TRAE, 19 (41.3%) experienced at least 1 Grade≥3 TRAE, 9 (19.6%) experienced at least 1 SAE, 6 (13.0%) experienced at least 1 treatment-related SAE, and 5 (10.9%) experienced any TEAE leading to treatment discontinuation. Twenty-eight patients in escalation and expansion cohort 1 had been treated at 160 mg QD, all of them had EGFR exon 20 insertion mutations. Of 28 patients, 26 patients had or were due for at least one post-baseline disease assessment and were included in the efficacy analysis. The overall response rate (ORR) (best response) and disease control rate (DCR) were 53.8% (95% CI: 33.37%, 73.41%) and 88.5% (95% CI: 69.85%, 97.55%), respectively, including 7 confirmed partial response (PR), 6 unconfirmed PR awaiting confirmation, and 10 stable disease (SD). The response (PR, CR) to Compound (A) was observed in patients regardless of prior treatment therapies including EGFR TKIs and immuno-oncology agents.

Figure 35:
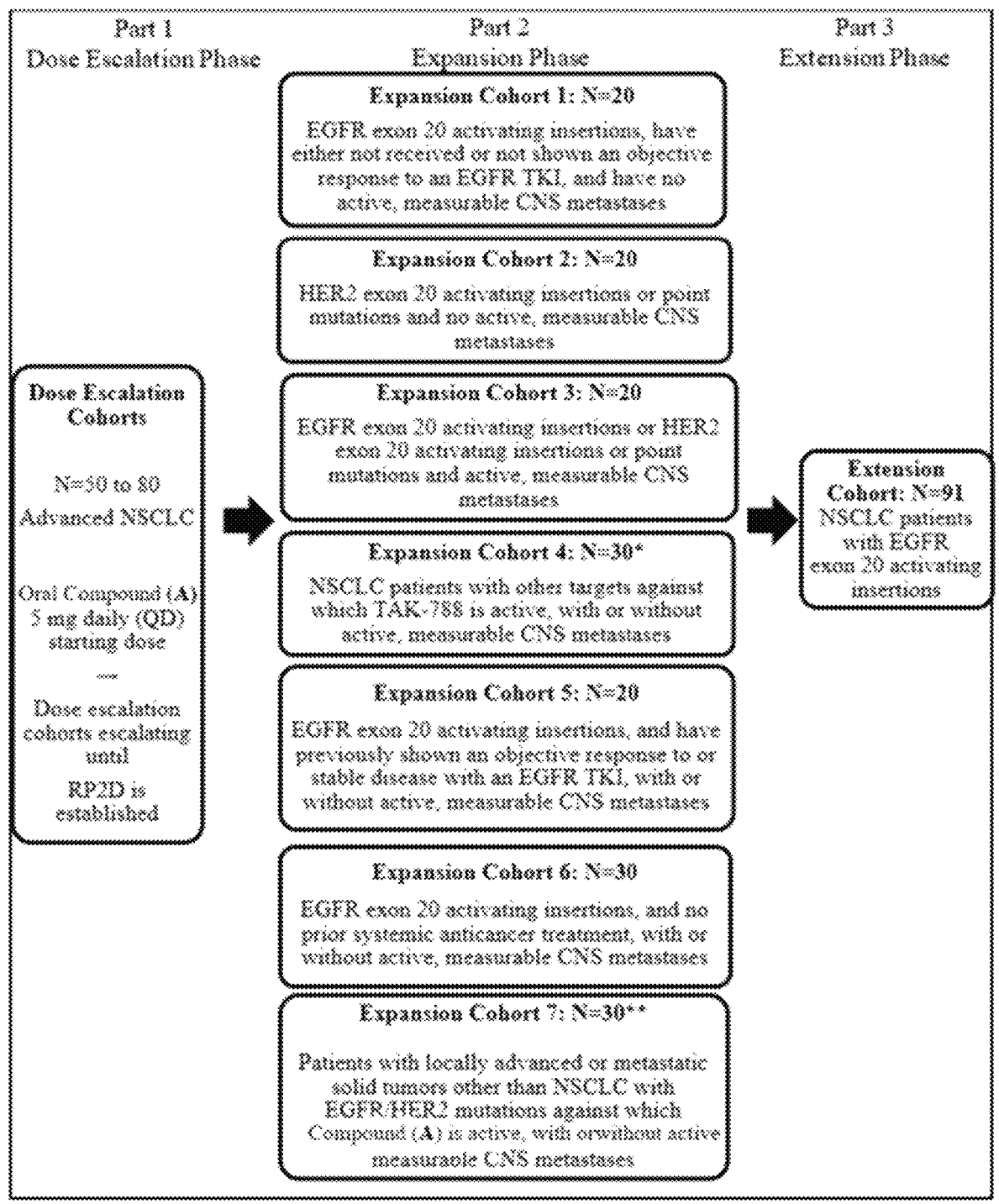
FIG. 35 is phase ½ trial design.

This study is a randomized, double-blind, placebo-controlled single rising dose study (Part 1), followed by an open-label, crossover evaluation of the effects of a low-fat meal on the pharmacokinetics (PK) of Compound (A) (Part 2), and a crossover evaluation of the relative bioavailability of Compound (A) drug-in-capsule (DiC) (test) versus DiC (reference) in healthy subjects (Part 3). Compound (A) was safe and well tolerated in healthy subjects up to a single oral dose of 160 mg. No SAEs were reported in healthy subjects. FIG. 35 shows phase ½ trial design.

Example 15: Clinical Pharmacology and Pharmacokinetics

The dose escalation portion of the study in Examples 13 and 14 was completed with a maximum tolerated dose determined at 160 mg QD in NSCLC patients with EGFR or HER20 exon 20 mutations or other EGFR uncommon mutations. The phase 2 portion of the study was initiated to expand the study in two 160 mg QD cohorts (EGFR exon 20 mutant NSCLC patients with or without brain metastases) and continue to enroll more patients in the 120 mg cohort.

Figure 33:
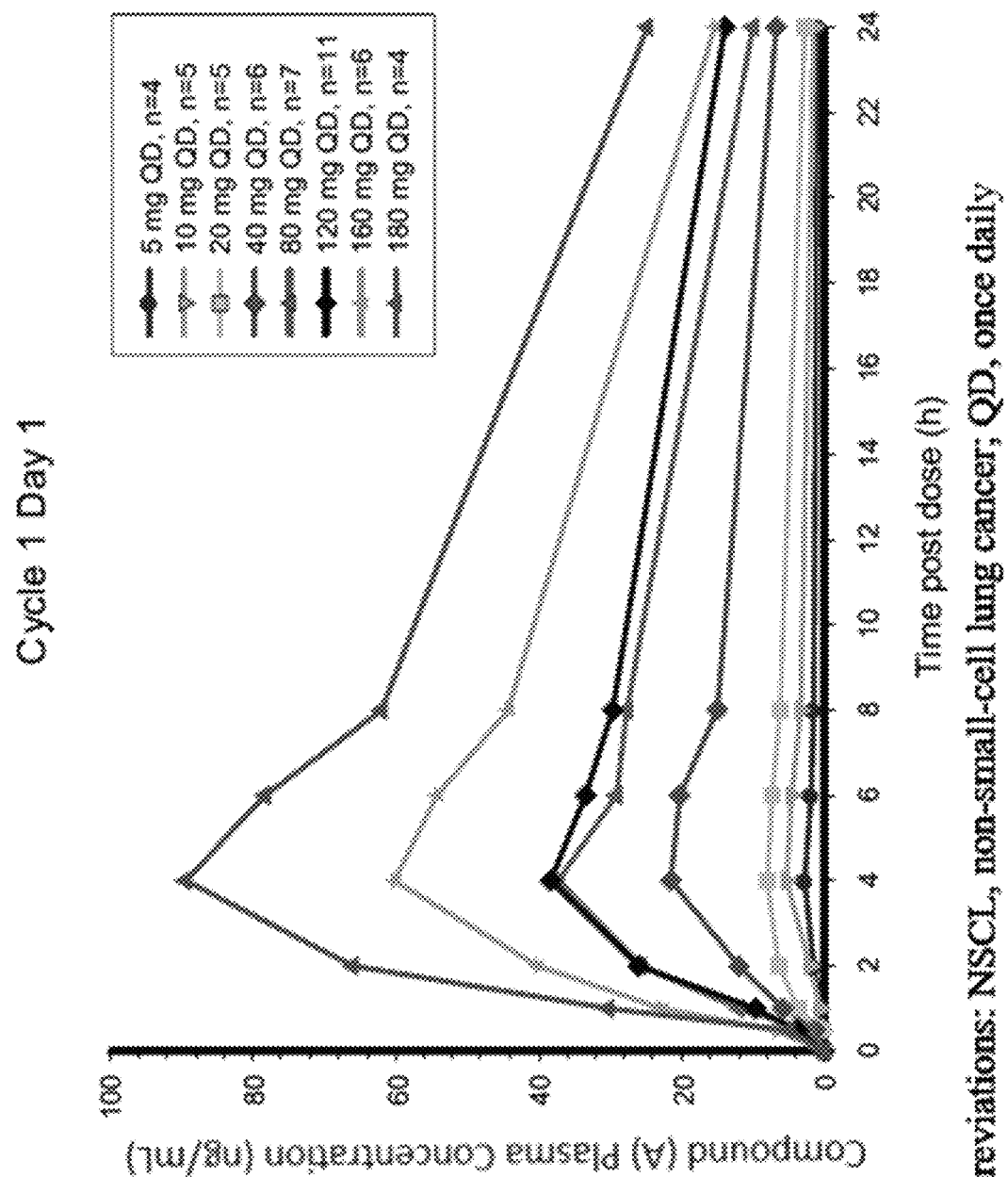
FIG. 33 is mean plasma concentration-time profiles of Compound (A) following oral administration of Compound (A) once per day in NSCLC patients.
Figure 34:
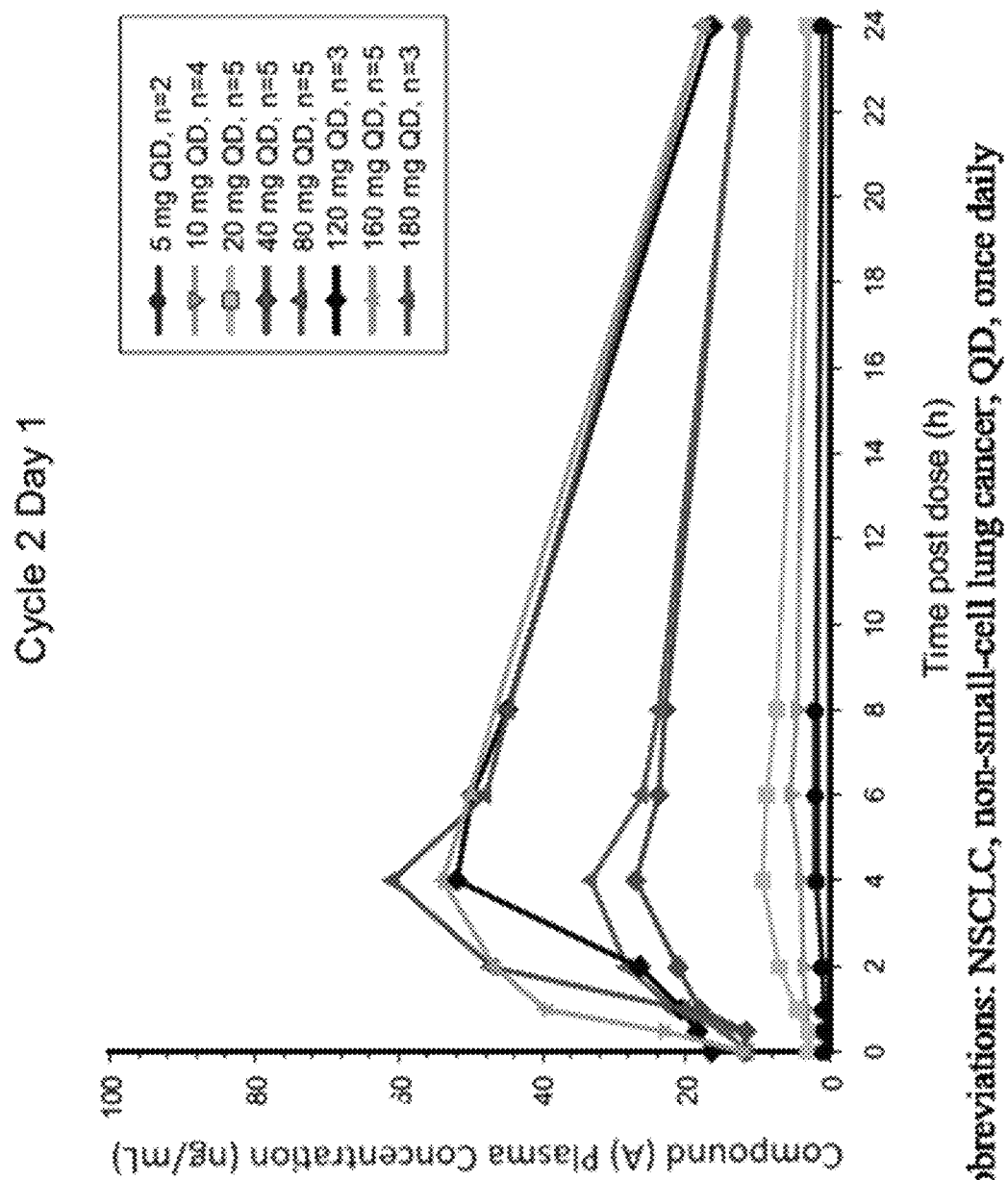
FIG. 34 is mean plasma concentration-time profiles of Compound (A) following oral administration of Compound (A) once per day in NSCLC patients.

Clinical PK data includes data from the dose escalation portion of the study. Compound (A) has been administered orally once per day in 28-day treatment cycles at dose levels of 5, 10, 20, 40, 80, 120, 160 and 180 mg. As mentioned above, Compound (A) was provided as polymorphic Form-I of the succinate salt of Compound (A). Compound (A) was formulated as a drug-in-capsule with no excipients and administered orally. The dosage identified in milligrams (mg) is based on the weight of the freebase of Compound (A). FIGS. 33, 34 show the mean plasma concentration-time profiles of Compound (A) following oral administration of Compound (A) once per day in NSCLC patients.

FIGS. 33 and 34: Mean plasma concentration-time profiles of Compound (A) following oral administration of Compound (A) once per day in NSCLC patients Compound (A) is administered orally on an empty stomach once per day continuously. Compound (A) was absorbed into system circulation following oral administration and the $C_{max}$ of Compound (A) was observed 4 to 6 hours post daily dose. Compound (A) $AUC_{24}$ on Cycle 2 Day 1 following multiple dose administration increased in an approximately dose-proportional manner over the dose range of 5 to 180 mg QD. Oral administration of Compound (A) QD resulted in approximately 1.5-fold accumulation in $AUC_{24}$. The geometric mean (range) of effective half-life based on accumulation was approximately 15 hours (6-27 hours). Accumulation of Compound (A), the peak/trough ratio of Compound (A), and the molar metabolite/parent $C_{av}$ ratios of the two active metabolites of Compound (A) were independent of Compound (A) dose in the range 5 to 180 mg QD, suggesting no obvious trend of time-dependent inhibition (TDI) or auto-induction.

We claim:

1. A succinate salt of Compound (A) in a crystalline form

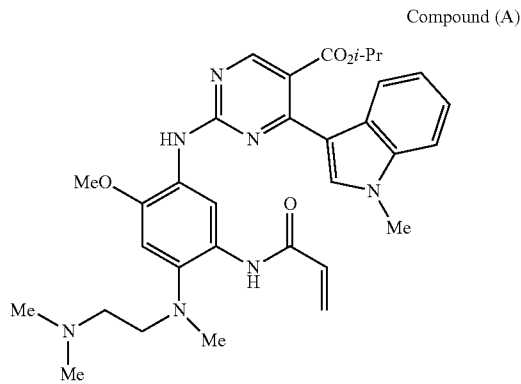

Compound (A)

wherein the crystalline form comprises an X-ray powder diffraction pattern expressed, in terms of 2-theta, at 8.3±0.20, 9.9±0.20, 11.7±0.20, and 22.5±0.20 degrees.

2. The succinate salt of Compound (A) of claim 1, which is mono-succinate.

3. The succinate salt of Compound (A) of claim 1, which is anhydrous mono-succinate.

4. The succinate salt of Compound (A) of claim 1 in a substantially crystalline form.

5. The succinate salt of Compound (A) of claim 4, wherein at least 98% by weight of the succinate salt of Compound (A) is in the crystalline form.

6. The succinate salt of Compound (A) of claim 4, wherein the crystalline form comprises an X-ray powder diffraction pattern expressed, in terms of 2-theta, at approximately 8.3±0.20, 9.9±0.20, 11.7±0.20, 14.3±0.20, 15.3±0.20, 18.6±0.20, 19.4±0.20, 21.9±0.20, 22.5±0.20, and 25.2±0.20 degrees.

7. The succinate salt of Compound (A) of claim 4, wherein the crystalline form comprises an X-ray powder diffraction pattern expressed, in terms of 2-theta, at approximately 8.3±0.20, 9.9±0.20, 11.4=0.20, 11.7±0.20, 14.3=0.20, 15.3=0.20, 18.6±0.20, 19.4=0.20, 19.9±0.20, 21.9±0.20, 22.5±0.20, 23.8=0.20, 25.2±0.20, and 25.6±0.20 degrees.

8. The succinate salt of Compound (A) of claim 4, wherein the crystalline form comprises an X-ray powder diffraction pattern expressed, in terms of 2-theta, at approximately

| Peak No. | Pos. [°2θ] |
| --- | --- |
| 1 | 8.3 |
| 2 | 9.9 |
| 3 | 10.5 |
| 4 | 10.8 |
| 5 | 11.4 |
| 6 | 11.7 |
| 7 | 12.4 |
| 8 | 14.3 |
| 9 | 14.7 |
| 10 | 15.3 |
| 11 | 15.5 |
| 12 | 17.0 |
| 13 | 17.1 |
| 14 | 17.6 |
| 15 | 18.1 |
| 16 | 18.6 |
| 17 | 19.4 |
| 18 | 19.9 |
| 19 | 21.9 |
| 20 | 22.0 |
| 21 | 22.5 |
| 22 | 22.8 |
| 23 | 23.0 |
| 24 | 23.4 |
| 25 | 23.7 |
| 26 | 23.8 |
| 27 | 24.2 |
| 28 | 24.4 |
| 29 | 25.0 |
| 30 | 25.2 |
| 31 | 25.6 |
| 32 | 27.1 |
| 33 | 27.4 |
| 34 | 29.1 |
| 35 | 29.9 |
| 36 | 30.5 |
| 37 | 31.5 |
| 38 | 31.9 |
| 39 | 33.0. |

9. The succinate salt of Compound (A) of claim 4, wherein the crystalline form is polymorphic Form-I having an X-ray powder diffraction pattern substantially as shown in FIG. 4.

10. A pharmaceutical composition comprising succinate salt of Compound (A) of claim 1 and optionally a pharmaceutically acceptable carrier Compound (A)

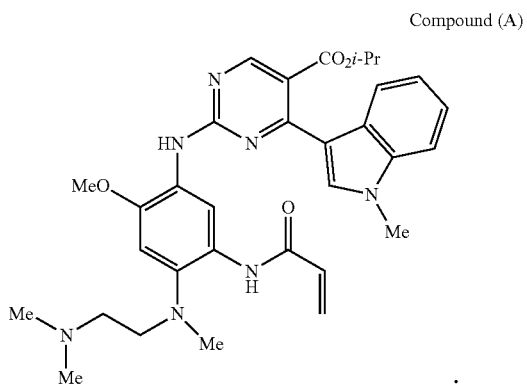

Int-b

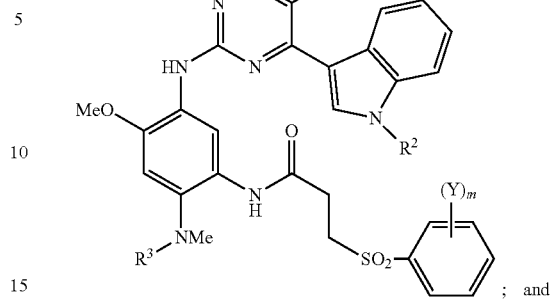
; and

11. A process for preparing a compound of formula (I)

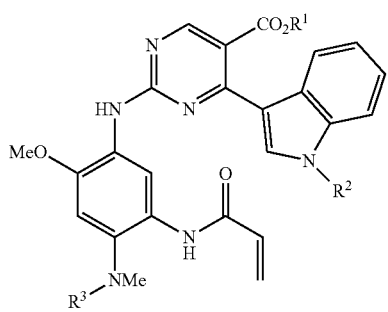
(I)

comprising:
(i) mixing a compound of formula (I-a) with a compound of formula (K)

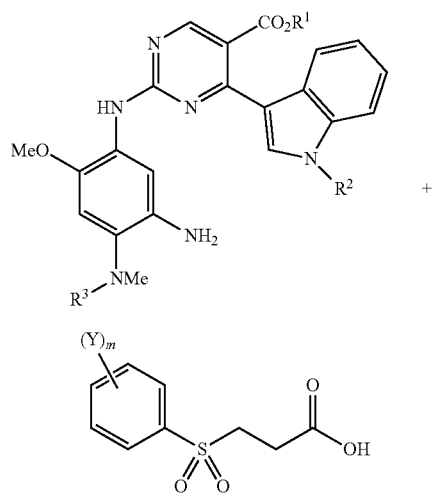

wherein
$R^1$ is alkyl;
$R^2$ is H or alkyl;
$R^3$ is alkyl substituted with an amino or heterocycloalkyl;
Y is $CH_3$, Cl, Br, F, or $OCH_3$; and m is 0, 1, 2, 3, 4, or 5;
(ii) adding a coupling reagent to the mixture of step (i) to form a compound of formula (Int-b);

(iii) treating the compound of formula (Int-b) with a base to generate a compound of formula (I).

12. The process of claim 11, wherein:
$R^1$ is isopropyl;
$R^2$ is H or methyl;
$R^3$ is ethyl substituted with $NR^4R^5$; wherein $R^4$ and $R^5$ are independently H or methyl; or
$R^3$ is methyl substituted with pyrrolidin-2-yl or 1-methylpyrrolidin-2-yl; and m is 0.

13. The process of claim 11, wherein:
$R^1$ is isopropyl;
$R^2$ is methyl;
$R^3$ is $-CH_2CH_2NR^4R^5$; wherein $R^4$ and $R^5$ are methyl; and m is 0.

14. The process of claim 11, wherein:
$R^1$ is isopropyl;
$R^2$ is methyl;
$R^3$ is ethyl substituted with $NR^4R^5$; wherein $R^4$ is H; $R^5$ is methyl; and m is 0.

15. The process of claim 11, wherein step (i) is conducted in the presence of a solvent at a temperature of between about −10° C. to about 50° C.

16. The process of claim 15, wherein step (i) is conducted in the presence of a solvent at a temperature of between about 2° C. to about 10° C.

17. The process of claim 15, wherein the solvent is selected from anhydrous dichloromethane, tetrahydrofuran (THF), 2-methyl tetrahydrofuran (2-MeTHF), isopropyl acetate (IPAc), cyclopentyl methyl ether (CPME), and dioxane.

18. The process of claim 11, wherein the mixture of step (i) is treated with a base.

19. The process of claim 11, wherein the coupling reagent is selected from propylphosphonic anhydride (T3P), thionyl chloride ($SOCl_2$), N,N'-diisopropyl carbodiimide (DIC), carbonyldiimidazole (CDI), phosgene (COCl2) and 1-Ethyl-3-(3-dimethylaminopropyl)carbodiimide (EDC).

20. The process of claim 19, wherein the coupling reagent is a solution comprising 50% w/w propylphosphonic anhydride and a solvent selected from tetrahydrofuran (THF) or 2-methyltetrahydrofuran (2-MeTHF), isopropyl acetate (IPAc), cyclopentyl methyl ether (CPME), and dioxane.

21. The process of claim 19, wherein the coupling reagent is added at a temperature of between about −10° C. to about 10° C.

22. The process of claim 11, wherein the base in step (iii) is selected from NaOH, DBU, KOt-Bu, NaOt-Bu, LiOt-Bu, DBN, KOH, and LiOH.

23. The process of claim 22, wherein step (iii) is conducted in the presence of a solvent at a temperature of between about 40° C. to about 90° C.

24. The process of claim 11, wherein the process is for preparing Compound (A)

Compound (A)

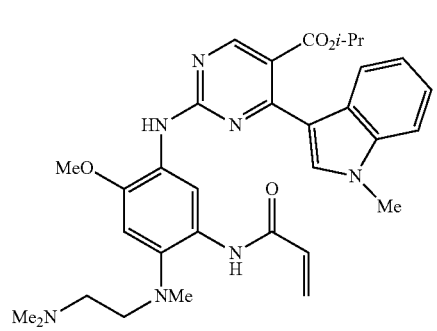

comprising:

(i) mixing a compound of formula (Int-4) with a compound of formula (K)

Int-4

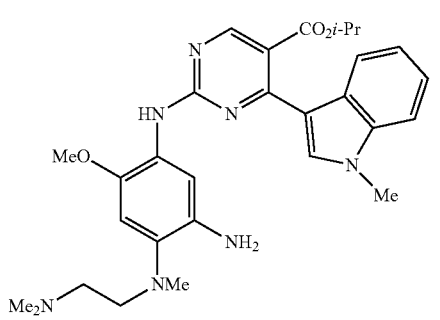

+

K

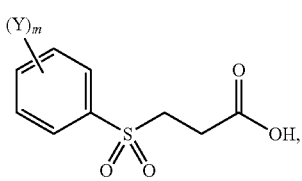

(ii) adding coupling reagent to the mixture of step (i) to form a compound of formula (Int-5);

Int-5

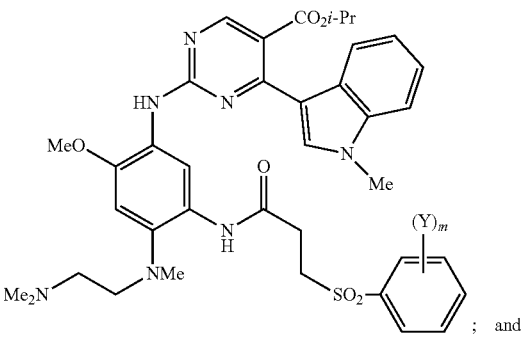

; and (iii) treating the compound of formula (Int-5) with a base to generate Compound (A);

wherein Y is $CH_3$, Cl, Br, F, or $OCH_3$; and m is 0, 1, 2, 3, 4, or 5.

25. The succinate salt of Compound (A) claim 1, wherein the crystalline form has a DSC profile characterized by an endothermic transition with an onset temperature at about 176.1±3° C.

26. The succinate salt of Compound (A) of claim 1, wherein the crystalline form has a DSC profile characterized by an endothermic transition at temperature of from about 175.1° C. to about 181.0° C.

27. The succinate salt of Compound (A) of claim 1, wherein the crystalline form has a TG/DTA profile substantially as shown in FIG. 6.

28. The succinate salt of Compound (A) of claim 1, wherein the crystalline form has a TG/DTA profile that displays an endothermic transition with an onset temperature of about 176.4° C., which is accompanied by a mass loss of 0.1% up to 150±2° C. followed by a mass loss of 1.2% up to 175° C. at a temperature changing rate of 10° C. per minute from 25° C. to 300° C., and decomposition at about 176.4° C. to about 178.5° C.

29. The succinate salt of Compound (A) of claim 1, wherein the crystalline form has a DSC profile that displays an endothermic transition with an onset temperature of about 176.1° C. with a melt of 178.5° C., and an associated enthalpy of 99.5 mJ/mg.

30. The succinate salt of Compound (A) of claim 1, wherein the unit cell dimensions are:

| | |
|---|---|
| a/Å | 8.9138(4) |
| b/Å | 12.4546(5) |
| c/Å | 17.9647(5) |
| α/° | 79.441(3) |
| β/° | 88.061(3) |
| γ/° | 71.127(4) |
| Volume/Å³ | 1854.52(13). |

* * * * *